(12) United States Patent
Hepperle et al.

(10) Patent No.: US 8,101,604 B2
(45) Date of Patent: Jan. 24, 2012

(54) ALPHA CARBOLINES AND USES THEREOF

(75) Inventors: Michael E. Hepperle, San Diego, CA (US); Julie Fields Liu, Lexington, MA (US); R. Scott Rowland, Swampscott, MA (US); Dilrukshi Vitharana, Somerville, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/859,312

(22) Filed: Aug. 19, 2010

(65) Prior Publication Data

US 2010/0311715 A1    Dec. 9, 2010

Related U.S. Application Data

(63) Continuation of application No. 11/706,760, filed on Feb. 15, 2007, now Pat. No. 7,812,018.

(60) Provisional application No. 60/774,091, filed on Feb. 16, 2006.

(51) Int. Cl.
*A61K 31/437*    (2006.01)

(52) U.S. Cl. .................................. 514/232.8

(58) Field of Classification Search ............. 514/232.8
See application file for complete search history.

(56) References Cited

FOREIGN PATENT DOCUMENTS

WO    WO 2004/054505 A2    7/2004

OTHER PUBLICATIONS

Golovko, T.V., et al., "New Synthesis of Beta-(2-alkoxyindolyl-3) Acrylic Acid Derivatives," *Khimiko-Farmatsevticheskii Zhurnal*, Moscow, Russia, vol. 28, No. 5, (1994), pp. 48-50.

Golovko, T.V., et al., "A New Approach to the Synthesis of Functionally-Substituted Pyrido[2, 3-d]indoles", *Mendeleev Communications, Institute of Physics Publishing*, Bristol, GB, vol. 6, (1995), pp. 226-227.

Frederiksen, H., et al., "Identification of Metabolites in Urine and Feces from Rats dosed with the Heterocyclic Amine, 2-amino-3-methyl-9H-pyrido[2, 3-b]Indole (MeAalphaC)," *Drug Metabolism and Disposition*, vol. 32, No. 6, (Jun. 1, 2004), pp. 661-665.

Isakovich, I.P., et al., "Synthesis of Condensed Indole Derivatives Based on 1-(2, 6-dichlorophenyl)-3-[(dimethylamino)methylene]-2-indolinone," *Khimiko-Farmatsevticheskii Zhurnal*, vol. 30, No. 9, (1996), pp. 35-39.

International Search Report filed in International Application No. PCT/US2007/003989, which corresponds to U.S. Appl. No. 11/706,760, filed Feb. 15, 2007.

*Primary Examiner* — Taofiq A Solola

(57) ABSTRACT

This invention provides alpha-carboline compounds of formula I:

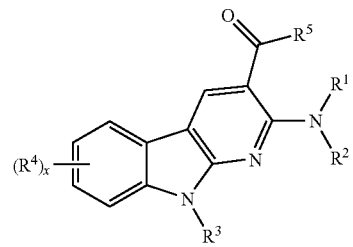

wherein $R^1$, $R^2$, $R^3$, $R^4$, $R^5$, and x are as described in the specification. The compounds are useful for treating inflammatory diseases and cancer.

5 Claims, No Drawings

ALPHA CARBOLINES AND USES THEREOF

PRIORITY INFORMATION

The present application is a continuation of U.S. patent application Ser. No. 11/706,760, filed Feb. 15, 2007 (pending), which claims the benefit of U.S. Provisional Application Ser. No. 60/774,091, filed Feb. 16, 2006 (abandoned). The entire contents of each of the above-referenced patent applications are incorporated herein by this reference.

BACKGROUND OF THE INVENTION

The transcription (nuclear) factor NF-κB is a member of the Rel protein family, and is typically a heterodimer composed of p50 and p65 subunits. NF-κB is constitutively present in the cytosol, and is inactivated by its association with one of the IκB family of inhibitors. Palombella et al., WO 95/25533, teaches that the ubiquitin-proteasome pathway plays an essential role in the regulation of NF-κB activity, being responsible for the processing of p105 to p50 and the degradation of the inhibitor protein IκB-α. Chen et al., Cell 84:853 (1996), teaches that prior to degradation, IκB-α undergoes selective phosphorylation at serine residues 32 and 36 by the multisubunit IκB kinase complex (IKK). IκB-α is phosphorylated by IKK, which has two catalytic subunits, IKK-1 (IκB kinase α or IKK-α) and IKK-2 (IκB kinase β or IKK-β). Once phosphorylated, IκB is targeted for ubiquitination and degradation by the 26S proteasome, allowing translocation of NF-κB into the nucleus, where it binds to specific DNA sequences in the promoters of target genes and stimulates their transcription. Inhibitors of IKK can block the phosphorylation of IκB and its further downstream effects, particularly those associated with NF-κB transcription factors.

The protein products of genes under the regulatory control of NF-κB include cytokines, chemokines, cell adhesion molecules, and proteins mediating cellular growth and control. Importantly, many of these proinflammatory proteins also are able to act, either in an autocrine or paracrine fashion, to further stimulate NF-κB activation. In addition, NF-κB plays a role in the growth of normal and malignant cells. Furthermore, NF-κB is a heterodimeric transcription factor which can activate a large number of genes which code, inter alia, for proinflammatory cytokines such as IL-1, IL-2, TNFα or IL-6. NF-κB is present in the cytosol of cells, building a complex with its naturally occurring inhibitor IκB. The stimulation of cells, for example by cytokines, leads to the phosphorylation and subsequent proteolytic degradation of IκB. This proteolytic degradation leads to the activation of NF-κB, which subsequently migrates into the nucleus of the cell and activates a large number of proinflammatory genes.

It would be beneficial to provide novel IKK inhibitors that possess good therapeutic properties, especially for the treatment of cancer, inflammatory diseases and immune-related diseases.

DETAILED DESCRIPTION OF THE INVENTION

1. General Description f Compounds of the Invention

This invention provides compounds that are inhibitors of IKK-2, and accordingly are useful for the treatment of cancer, inflammatory diseases, and immune-related diseases. The compounds of this invention are represented by formula I:

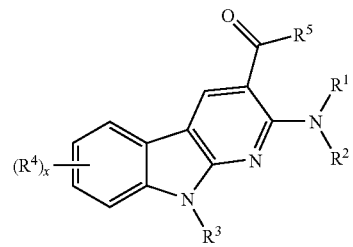

or a pharmaceutically acceptable salt thereof wherein,
$R^1$ is hydrogen, $C_1$-$C_4$ aliphatic, —C(O)N($R^{1a}$)$_2$, —C(O)$R^{1b}$, or —(CH$_2$)$_n$$R^{1c}$,
wherein each occurrence of $R^{1a}$ is independently hydrogen, C(O)O$R^{1d}$, or an optionally substituted group selected from $C_1$-$C_6$ aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of $R^{1a}$ are taken together with a nitrogen atom to which they are bound to form an optionally substituted 3-7-membered heterocyclyl ring;
$R^{1b}$ is an optionally substituted group selected from $C_1$-$C_6$ aliphatic or phenyl;
$R^{1c}$ is —N($R^{1a}$)$_2$, or an optionally substituted phenyl or pyridyl group;
$R^{1d}$ is $C_1$-$C_6$ aliphatic; and
n is 1, 2, or 3;
$R^2$ is hydrogen or $C_1$-$C_4$ aliphatic;
$R^3$ is —H, -$T_1$-$R^{3d}$, —$V_1$—$R^{3a}$, —$V_1$-$T_1$-$R^{3d}$, or —$R^{3e}$, wherein
$V_1$ is —C(O)—, —S(O)$_2$—, —C(O)N$R^{3a}$—, or —S(O)$_2$N$R^{3a}$—;
$T_1$ is a $C_1$-$C_6$ alkylene chain optionally substituted with one or more independent occurrences of —$R^{3b}$, wherein the alkylene chain optionally is interrupted by —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')S(O)$_2$N (R')—, —OC(O)—, or —C(O)N(R')—O— or wherein $T_1$ or a portion thereof optionally forms part of an optionally substituted 3-7 membered cycloaliphatic or heterocyclyl ring;
each occurrence of $R^{3a}$ is independently hydrogen or an optionally substituted group selected from $C_1$-$C_6$ aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of $R^{3a}$ are taken together with a nitrogen atom to which they are bound to form an optionally substituted 3-7-membered heterocyclyl ring;
each occurrence of $R^{3b}$ is independently halogen, —CN, —NO$_2$, —$R^{3c}$, —N($R^{3a}$)$_2$, —O$R^{3a}$, —S$R^{3c}$, —S(O)$_2$$R^{3c}$, —C(O)$R^{3a}$, —C(O)O$R^{3a}$, —C(O)N($R^{3a}$)$_2$, —S(O)$_2$N($R^{3a}$)$_2$, —OC(O)N($R^{3a}$)$_2$, —N(R')C(O)$R^{3a}$, —N(R')SO$_2$$R^{3c}$, —N(R')C(O)O$R^{3a}$, —N(R')C(O)N($R^{3a}$)$_2$, —N(R')SO$_2$N ($R^{3a}$)$_2$, —N$R^{3a}$(C=N$R^{3a}$)N($R^{3a}$)$_2$, =N$R^{3a}$, =N—N($R^{3a}$)$_2$, =N—O$R^{3a}$, =N—NHC(O)$R^{3a}$, =N—NHCO$_2$$R^{3a}$, =N—NHSO$_2$$R^{3a}$, or two occurrences of $R^{3a}$ or $R^{3c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur;

each occurrence of $R^{3c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3e}$ is independently an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur and each R' is independently hydrogen or optionally substituted $C_{1-6}$aliphatic;

x is 0-4;

each occurrence of $R^4$ is independently —$R^{4a}$, -$T_2$-$R^{4d}$, or —$V_2$-$T_2$-$R^{4d}$, wherein:

each occurrence of $R^{4a}$ is independently halogen, —CN, —NO$_2$, —$R^{4c}$, —N($R^{4b}$)$_2$, —OR$^{4b}$, —SR$^{4c}$, —S(O)$_2$R$^{4c}$, —C(O)R$^{4b}$, —C(O)OR$^{4b}$, —C(O)N(R$^{4b}$)$_2$, —S(O)$_2$N(R$^{4b}$)$_2$, —OC(O)N(R$^{4b}$)$_2$, —N(R')C(O)R$^{4b}$, —N(R')SO$_2$R$^{4c}$, —N(R')C(O)OR$^{4b}$, —N(R')C(O)N(R$^{4b}$)$_2$, or —N(R')SO$_2$N(R$^{4b}$)$_2$, or two occurrences of $R^{4b}$ or $R^{4c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur, or two occurrences of $R^{4b}$, taken together with a nitrogen atom to which they are bound, form an optionally substituted 3-7-membered heterocyclyl ring having 0-3 additional heteroatoms selected from nitrogen, oxygen, or sulfur;

each occurrence of $R^{4b}$ is independently hydrogen or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4c}$ is independently an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $V_2$ is independently —C(R')=C(R')—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O—; and each occurrence of $T_2$ is independently a $C_1$-$C_6$alkylene chain optionally substituted with $R^{4a}$, wherein the alkylene chain optionally is interrupted by —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O— or wherein $T_2$ or a portion thereof optionally forms part of an optionally substituted 3-7 membered cycloaliphatic or heterocyclyl ring, and $R^5$ is —NR$^6$R$^7$ or —OH, wherein:

$R^6$ and $R^7$ are each independently hydrogen or $C_1$-$C_4$aliphatic;

provided that the compound of formula I is other than:
a) 2-amino-9-ethyl-9H-Pyrido[2,3-b]indole-3-carboxamide;
b) 2-amino-1H-Pyrido[2,3-b]indole-3-carboxamide, or the monohydrochloride thereof,
c) 2-amino-1H-Pyrido[2,3-b]indole-3-carboxylic acid; or
d) 2-amino-9-(2,6-dichlorophenyl)-9H-Pyrido[2,3-b]indole-3-carboxamide.

In other embodiments, the compounds of this invention are represented by formula I-A:

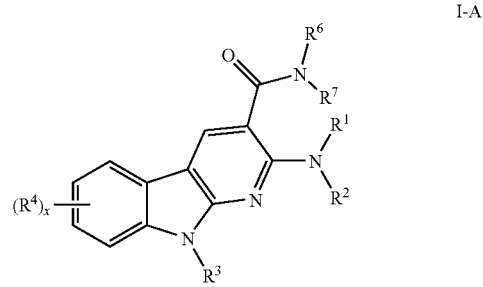

or a pharmaceutically acceptable salt thereof wherein, $R^1$ is hydrogen, $C_1$-$C_4$aliphatic, or —C(O)N(R$^{1a}$)$_2$;

wherein each occurrence of $R^{1a}$ is independently hydrogen or $C_1$-$C_4$aliphatic;

$R^2$ is hydrogen or $C_1$-$C_4$aliphatic;

$R^3$ is —H, -$T_1$-$R^{3d}$, —$V_1$—$R^{3a}$, —$V_1$-$T_1$-$R^{3d}$, or —$R^{3e}$, wherein $V_1$ is —C(O)—, —S(O)$_2$—, —C(O)NR$^{3a}$—, or —S(O)$_2$NR$^{3a}$—;

$T_1$ is a $C_1$-$C_6$alkylene chain optionally substituted with one or more independent occurrences of —$R^{3b}$, wherein the alkylene chain optionally is interrupted by —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')S(O)$_2$N(R')—, —OC(O)—, or —C(O)N(R')—O— or wherein $T_1$ or a portion thereof optionally forms part of an optionally substituted 3-7 membered cycloaliphatic or heterocyclyl ring;

each occurrence of $R^{3a}$ is independently hydrogen or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of $R^{3a}$ are taken together with a nitrogen atom to which they are bound to form an optionally substituted 3-7-membered heterocyclyl ring;

each occurrence of $R^{3b}$ is independently halogen, —CN, —$NO_2$, —$R^{3e}$, —$N(R^{3a})_2$, —$OR^{3a}$, —$S(O)_2R^{3e}$, —C(O)$R^{3a}$, —C(O)$OR^{3a}$, —C(O)N($R^{3a})_2$, —$S(O)_2N(R^{3a})_2$, —OC(O)N($R^{3a})_2$, —N(R')C(O)$R^{3a}$, —N(R')$SO_2R^{3e}$, —N(R')C(O)$OR^{3a}$, —N(R')C(O)N($R^{3a})_2$, or —N(R')$SO_2N(R^{3a})_2$, or two occurrences of $R^{3a}$ or $R^{3c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur;

each occurrence of $R^{3c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3e}$ is independently an optionally substituted group selected from 3-10-membered cycloaliphatic, or 3-10-membered heterocyclyl having 1-5 heteroatoms independently selected from nitrogen, oxygen, or sulfur; and each R' is independently hydrogen or optionally substituted $C_{1-6}$aliphatic;

x is 0-4;

each occurrence of $R^4$ is independently —$R^{4a}$, -$T_2$-$R^{4d}$, or —$V_2$-$T_2$-$R^{4d}$, wherein:

each occurrence of $R^{4a}$ is independently halogen, —CN, —$NO_2$, —$R^{4c}$, —$N(R^{4b})_2$, —$OR^{4b}$, —$SR^{4c}$, —$S(O)_2R^{4c}$, —C(O)$R^{4b}$, —C(O)$OR^{4b}$, —C(O)N($R^{4b})_2$, —$S(O)_2N(R^{4b})_2$, —OC(O)N($R^{4b})_2$, —N(R')C(O)$R^{4b}$, —N(R')$SO_2R^{4c}$, —N(R')C(O)$OR^{4b}$, —N(R')C(O)N($R^{4b})_2$, or —N(R')$SO_2N(R^{4b})_2$, or two occurrences of $R^{4b}$ or $R^{4c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur, or two occurrences of $R^{4b}$, taken together with a nitrogen atom to which they are bound, form an optionally substituted 3-7-membered heterocyclyl ring having 0-3 additional heteroatoms selected from nitrogen, oxygen, or sulfur;

each occurrence of $R^{4b}$ is independently hydrogen or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4c}$ is independently an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $V_2$ is independently —C(R')═C(R')—, —C≡C—, —N(R')—, —O—, —S—, —$S(O)_2$—, —C(O)—, —C(O)O—, —C(O)N(R')—, —$S(O)_2N(R')$—, —OC(O)N(R')—, —N(R')C(O)—, —N(R')$SO_2$—, —N(R')C(O)O—, —NR'C(O)N(R')—, —N(R')$SO_2N(R')$—, —OC(O)—, or —C(O)N(R')—O—; and each occurrence of $T_2$ is independently a $C_1$-$C_6$alkylene chain optionally substituted with $R^{4a}$, wherein the alkylene chain optionally is interrupted by —C(R')═C(R')—, —C≡C—, —N(R')—, —O—, —S—, —S(O)—, —$S(O)_2$—, —C(O)—, —C(O)O—, —C(O)N(R')—, —$S(O)_2N(R')$—, —OC(O)N(R')—, —N(R')C(O)—, —N(R')$SO_2$—, —N(R')C(O)O—, —NR'C(O)N(R')—, —N(R')$SO_2N(R')$—, —OC(O)—, or —C(O)N(R')—O— or wherein $T_2$ or a portion thereof optionally forms part of an optionally substituted 3-7 membered cycloaliphatic or heterocyclyl ring, and $R^6$ and $R^7$ are each independently hydrogen or $C_1$-$C_4$aliphatic;

provided that the compound of formula I is other than:
a) 2-amino-9-ethyl-9H-Pyrido[2,3-b]indole-3-carboxamide; or
b) 2-amino-1H-Pyrido[2,3-b]indole-3-carboxamide, or the monohydrochloride thereof.

2. Compounds and Definitions

Compounds of this invention include those described generally above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient. The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR$^o$, —S(O)R$^o$, —SO$_2$R$^o$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R$^o$, —NR$^+$CO$_2$R$^+$, —NR$^+$SO$_2$R$^o$, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R$^o$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R$^o$)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R$^o$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R$^o$=N—NHSO$_2$R$^o$ or =N—R* where R$^o$ is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of OR⁺

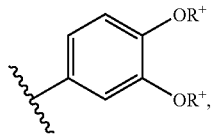

these two occurrences of R⁺ are taken together with the oxygen atoms to which they are bound to form a fused 6-membered oxygen containing ring:

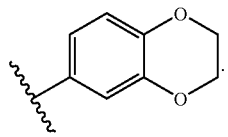

It will be appreciated that a variety of other rings (e.g., Spiro and bridged rings) can be formed when two independent occurrences of R⁺ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95% 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

In certain embodiments, for compounds of formula I or I-A, $R^5$ is —NR⁶R⁷, and $R^6$ and $R^7$ are each hydrogen. In other embodiments, $R^6$ and $R^7$ are each hydrogen, $R^1$ is hydrogen or —C(O)N(R$^{1a}$)$_2$ and $R^2$ is hydrogen. In still other embodiments, $R^1$, $R^2$, $R^6$ and $R^7$ are each hydrogen and compounds have the structure of formula I-B:

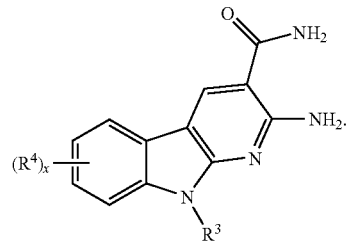

I-B

In other embodiments, $R^3$ is -T$_1$-R$^{3d}$, —V$_1$-T$_1$-R$^{3d}$, or —R$^{3e}$. In yet other embodiments, $R^3$ is -T$_1$-R$^{3d}$ or —V$_1$-T$_1$-R$^{3d}$. In still other embodiments, $R^3$ is -T$_1$-R$^{3d}$.

In some embodiments, T$_1$ is a C$_1$-C$_4$alkylene chain wherein the alkylene chain is optionally substituted by 1 or 2 independent occurrences of R$^{3b}$, and the alkylene chain is optionally interrupted by —C(R')═C(R')—, —N(R')—, —O—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')S(O)$_2$N(R')—, —OC(O)—, or —C(O)N(R')—O—, and wherein each occurrence of R$^{3b}$ is independently C$_1$-C$_3$aliphatic, —CN, —N(R$^{3a}$)$_2$, —OR$^{3a}$, —SR$^{3c}$, —S(O)$_2$R$^{3c}$, —C(O)R$^{3a}$, —C(O)OR$^{3a}$, —C(O)N(R$^{3a}$)$_2$, —S(O)$_2$N(R$^{3a}$)$_2$, —OC(O)N(R$^{3a}$)$_2$, —N(R')C(O)R$^{3a}$, —N(R')SO$_2$R$^{3c}$, —N(R')C(O)OR$^{3a}$, —N(R')C(O)N(R$^{3a}$)$_2$, or —N(R')SO$_2$N(R$^{3a}$)$_2$.

In other embodiments, T$_1$ is a C$_1$-C$_4$alkylene chain wherein the alkylene chain is optionally substituted by 1 or 2 independent occurrences of R$^{3b}$, and the alkylene chain is optionally interrupted by —C(R')═C(R')—, —N(R')—, —O—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')S (O)$_2$N(R')—, —OC(O)—, or —C(O)N(R')—O—, and wherein each occurrence of —R$^{3b}$ is independently C$_1$-C$_3$aliphatic, —N(R$^{3a}$)$_2$, —OR$^{3a}$, —C(O)OR$^{3a}$, —C(O)N(R$^{3a}$)$_2$, —S(O)$_2$N(R$^{3a}$)$_2$, —OC(O)N(R$^{3a}$)$_2$, —N(R')C(O)R$^{3a}$, —N(R')SO$_2$R$^{3c}$, —N(R')C(O)OR$^{3a}$, —N(R')C(O)N(R$^{3a}$)$_2$, or —N(R')SO$_2$N(R$^{3a}$)$_2$.

In some embodiments, R$^{3d}$ is hydrogen. In other embodiments, each occurrence of R$^{3b}$ is independently —N(R$^{3a}$)$_2$, C$_1$-C$_3$alkyl, or —OR$^{3a}$.

In other embodiments, x is 0, 1, or 2, and each occurrence of R$^4$ is independently halogen, CN, —NO$_2$, —R$^{4c}$, —N(R$^{4b}$)$_2$, —OR$^{4b}$, —S(O)$_2$R$^{4c}$, —C(O)R$^{4b}$, —C(O)OR$^{4b}$, —C(O)N(R$^{4b}$)$_2$, —S(O)$_2$N(R$^{4b}$)$_2$, —N(R')C(O)R$^{4b}$, or —N(R')SO$_2$R$^{4c}$. In other embodiments, each occurrence of R$^4$ is independently halogen, —R$^{4c}$, —N(R$^{4b}$)$_2$, —OR$^{4b}$, or —SR$^{4c}$. In still other embodiments, each occurrence of R$^4$ is independently halogen or C$_1$-C$_4$alkyl.

In still other embodiments, compounds have the structure of formula I-B:

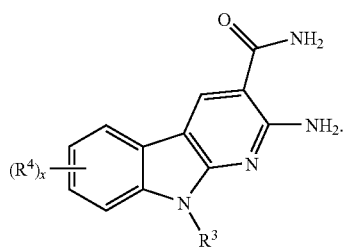

I-B wherein R$^3$ is -T$_1$-R$^{3d}$,

T$_1$ is a C$_1$-C$_4$alkylene chain wherein the alkylene chain is optionally substituted by 1 or 2 independent occurrences of R$^{3b}$, and the alkylene chain is optionally interrupted by —C(R')=C(R')—, —N(R')—, —O—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR' C(O)N(R')—, —N(R')S(O)$_2$N(R')—, —OC(O)—, or —C(O)N(R')—O—;

R$^{3d}$ is hydrogen;

each occurrence of R$^{3b}$ is independently C$_1$-C$_3$aliphatic, —N(R$^{3a}$)$_2$, —OR$^{3a}$, —C(O)OR$^{3a}$, —C(O)N(R$^{3a}$)$_2$, —S(O)$_2$N(R$^{3a}$)$_2$, —OC(O)N(R$^{3a}$)$_2$, —N(R')C(O)R$^{3a}$, —N(R')SO$_2$R$^{3c}$, —N(R')C(O)OR$^{3a}$, N(R')C(O)N(R$^{3a}$)$_2$, or —N(R')SO$_2$N(R$^{3a}$)$_2$;

x is 0, 1, or 2; and each occurrence of R$^4$ is independently halogen, —CN, —NO$_2$, —R$^{4c}$, —N(R$^{4b}$)$_2$, —OR$^{4b}$, —SR$^{4c}$, —S(O)$_2$R$^{4c}$, —C(O)R$^{4b}$, —C(O)OR$^{4b}$, —C(O)N(R$^{4b}$)$_2$, —S(O)$_2$N(R$^{4b}$)$_2$, —N(R')C(O)R$^{4b}$, or —N(R')SO$_2$R$^{4c}$.

In some embodiments, for compounds of formula I-B described directly above, T$_1$ is C$_1$-C$_4$alkyl substituted with 1 or 2 independent occurrences of —R$^{3b}$, wherein each occurrence of —R$^{3b}$ is independently —N(R$^{3a}$)$_2$, —OR$^{3a}$, or C$_1$-C$_3$alkyl.

Table 1 below depicts certain exemplary compounds of formula I.

TABLE 1

Examples of formula I compounds

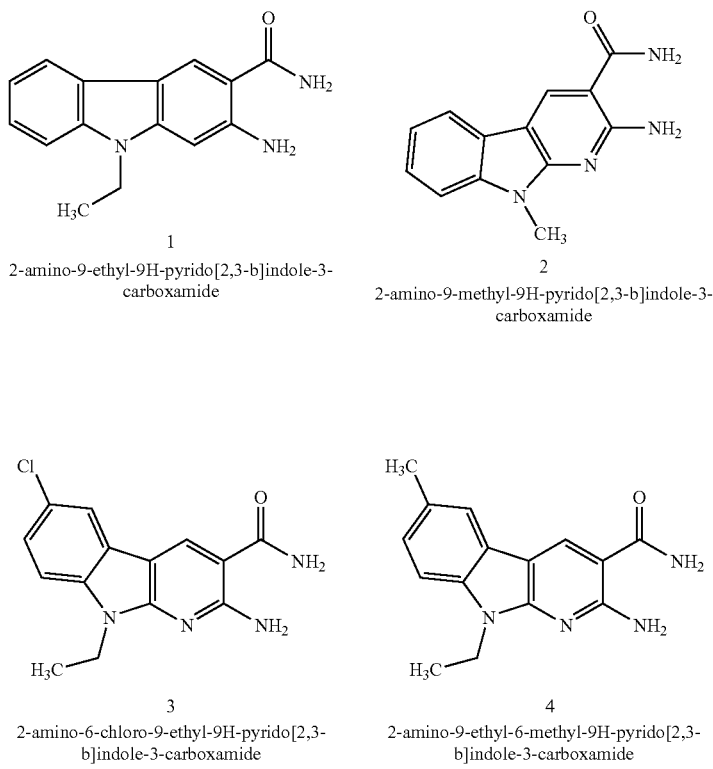

1
2-amino-9-ethyl-9H-pyrido[2,3-b]indole-3-carboxamide 2
2-amino-9-methyl-9H-pyrido[2,3-b]indole-3-carboxamide 3
2-amino-6-chloro-9-ethyl-9H-pyrido[2,3-b]indole-3-carboxamide 4
2-amino-9-ethyl-6-methyl-9H-pyrido[2,3-b]indole-3-carboxamide TABLE 1-continued

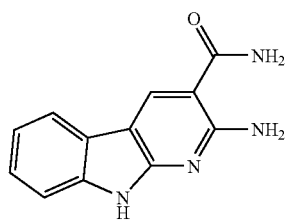

5
2-amino-9H-pyrido[2,3-b]indole-3-carboxamide

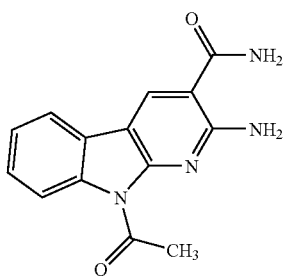

6
9-acetyl-2-amino-9H-pyrido[2,3-b]indole-3-carboxamide

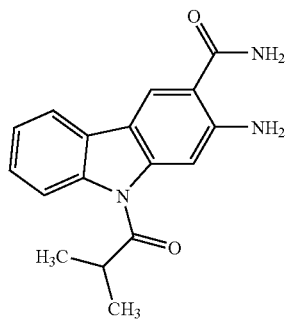

7
2-amino-9-isobutyryl-9H-pyrido[2,3-b]indole-3-carboxamide

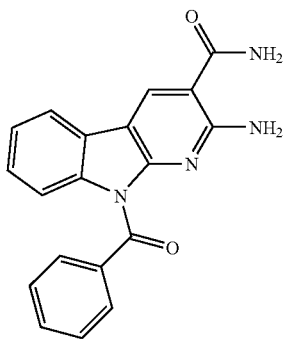

8
2-amino-9-benzoyl-9H-pyrido[2,3-b]indole-3-carboxamide

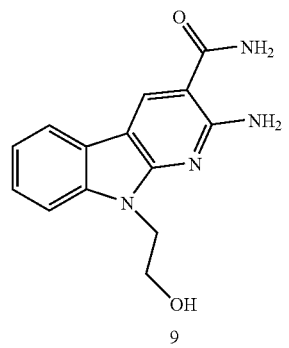

9
2-amino-9-(2-hydroxyethyl)-9H-pyrido[2,3-b]indole-3-carboxamide

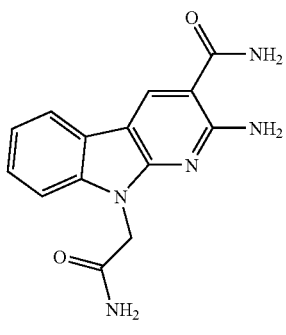

10
2-amino-9-(2-amino-2-oxoethyl)-9H-pyrido[2,3-b]indole-3-carboxamide

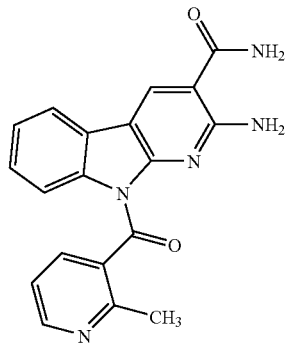

11
2-amino-9-[(2-methylpyridin-3-yl)-carbonyl]-9H-pyrido[2,3-b]indole-3-carboxamide

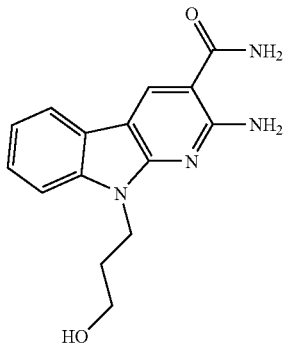

12
2-amino-9-(3-hydroxypropyl)-9H-pyrido[2,3-b]indole-3-carboxamide

TABLE 1-continued
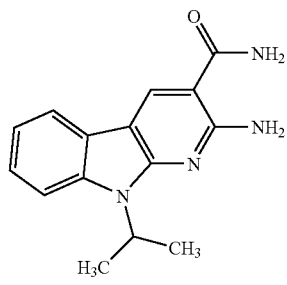
13
2-amino-9-isopropyl-9H-pyrido[2,3-b]indole-3-carboxamide
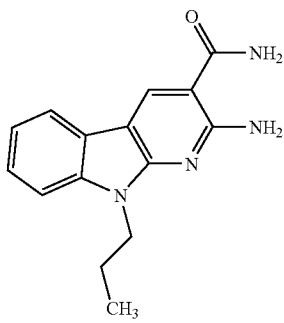
14
2-amino-9-propyl-9H-pyrido[2,3-b]indole-3-carboxamide
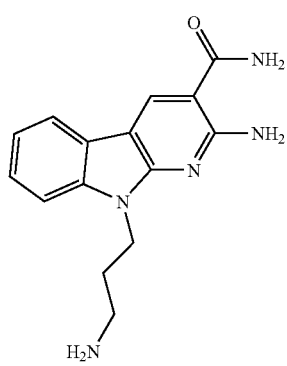
15
2-amino-9-(3-aminopropyl)-9H-pyrido[2,3-b]indole-3-carboxamide
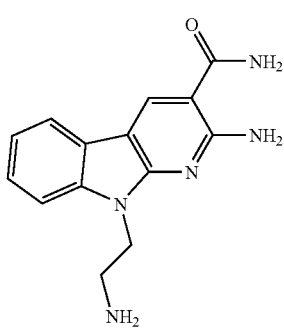
16
2-amino-9-(2-aminoethyl)-9H-pyrido[2,3-b]indole-3-carboxamide
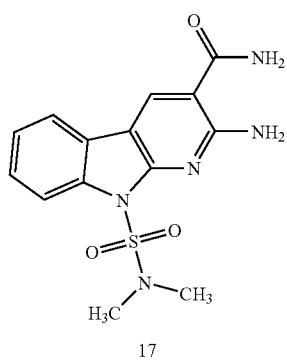
17
2-amino-9-[(dimethylamino)sulfonyl]-9H-pyrido[2,3-b]indole-3-carboxamide
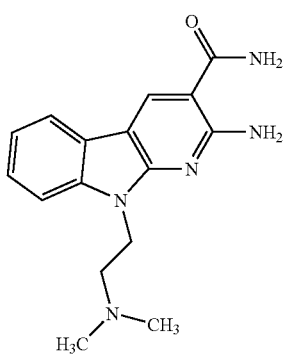
18
2-amino-9-[2-(dimethylamino)ethyl]-9H-pyrido[2,3-b]indole-3-carboxamide TABLE 1-continued

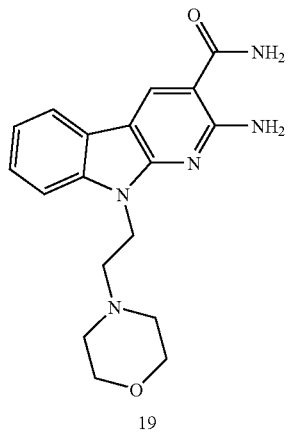

19
2-amino-9-(2-morpholin-4-ylethyl)-9H-pyrido[2,3-b]indole-3-carboxamide

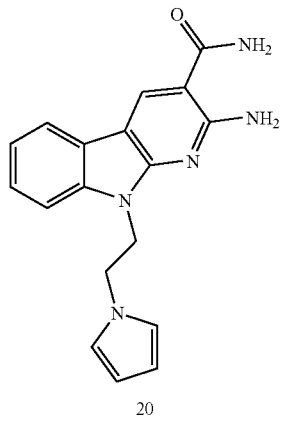

20
2-amino-9-[2-(1H-pyrrol-1-yl)ethyl]-9H-pyrido[2,3-b]indole-3-carboxamide

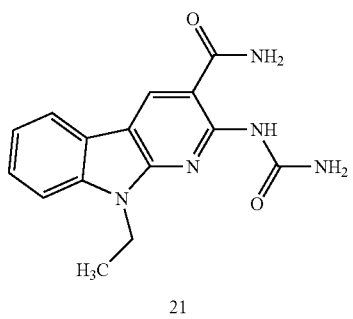

21
2-[(aminocarbonyl)amino]-9-ethyl-9H-pyrido[2,3-b]indole-3-carboxamide

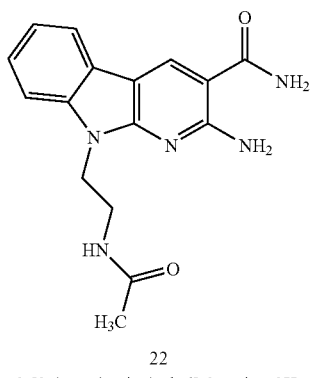

22
9-[2-(acetylamino)ethyl]-2-amino-9H-pyrido[2,3-b]indole-3-carboxamide

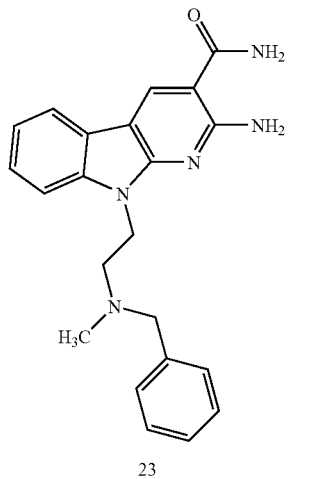

23
2-amino-9-{2-[benzyl(methyl)amino]ethyl}-9H-pyrido[2,3-b]indole-3-carboxamide

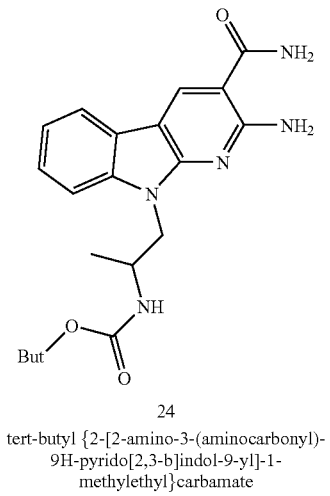

24
tert-butyl {2-[2-amino-3-(aminocarbonyl)-9H-pyrido[2,3-b]indol-9-yl]-1-methylethyl}carbamate TABLE 1-continued

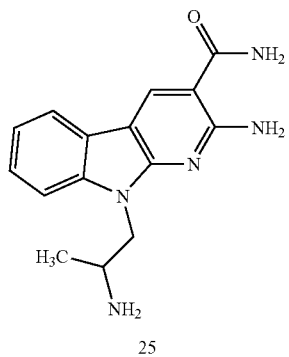

25
2-amino-9-(2-aminopropyl)-9H-pyrido[2,3-b]indole-3-carboxamide

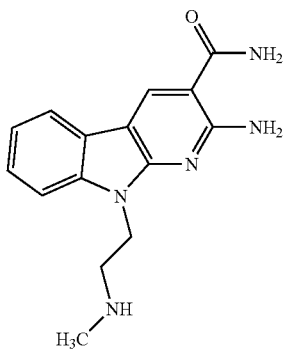

26
2-amino-9-[2-(methylamino)ethyl]-9H-pyrido[2,3-b]indole-3-carboxamide

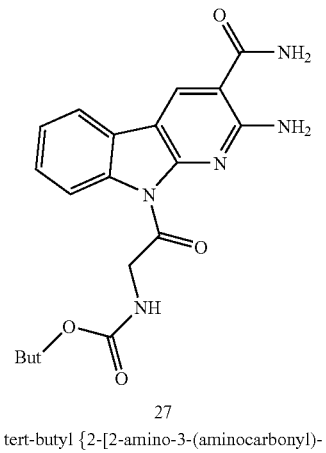

27
tert-butyl {2-[2-amino-3-(aminocarbonyl)-9H-pyrido[2,3-b]indol-9-yl]-2-oxoethyl}carbamate

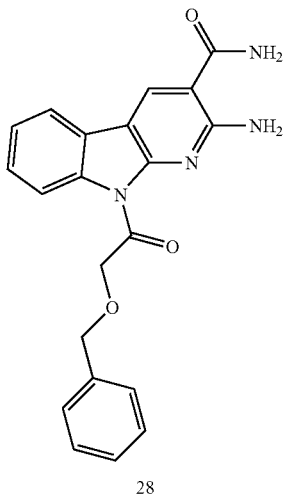

28
2-amino-9-[(benzyloxy)acetyl]-9H-pyrido[2,3-b]indole-3-carboxamide

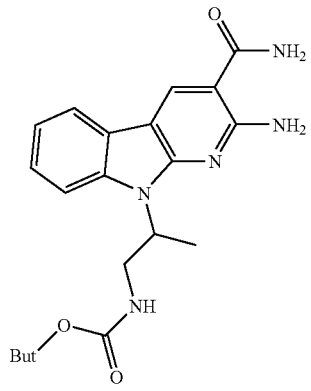

29
tert-butyl {2-[2-amino-3-(aminocarbonyl)-9H-pyrido[2,3-b]indol-9-yl]propyl}carbamate

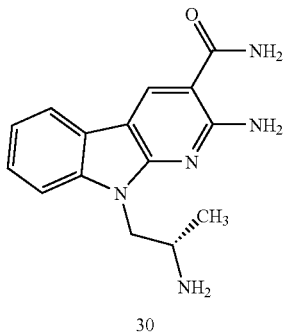

30
2-amino-9-[(2S)-2-aminopropyl]-9H-pyrido[2,3-b]indole-3-carboxamide

TABLE 1-continued

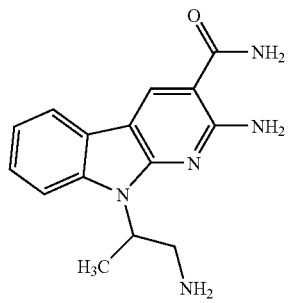

31
2-amino-9-(2-amino-1-methylethyl-9H-pyrido[2,3-b]indole-3-carboxamide

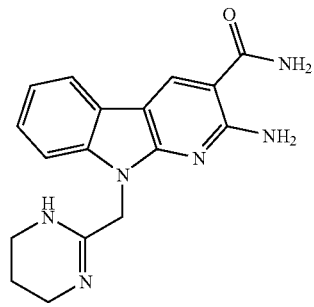

32
2-amino-9-(1,4,5,6-tetrahydropyrimidin-2-ylmethyl)-9H-pyrido[2,3-b]indole-3-carboxamide

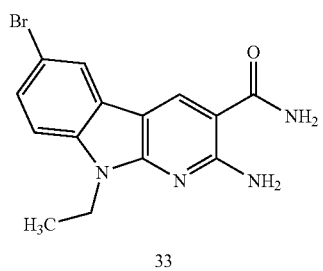

33
2-amino-6-bromo-9-ethyl-9H-pyrido[2,3-b]indole-3-carboxamide

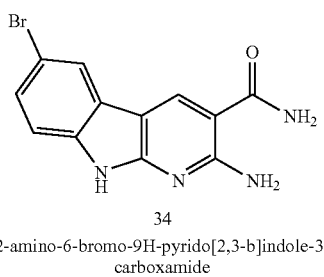

34
2-amino-6-bromo-9H-pyrido[2,3-b]indole-3-carboxamide

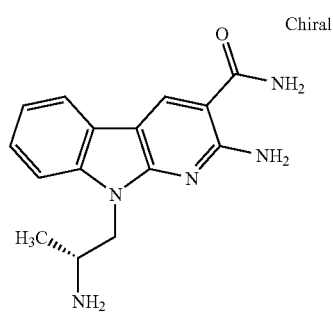

35
2-amino-9-[(2R)-2-aminopropyl]-9H-pyrido[2,3-b]indole-3-carboxamide

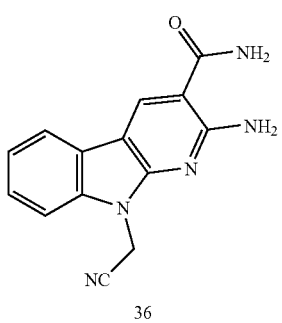

36
2-amino-9-(cyanomethyl)-9H-pyrido[2,3-b]indole-3-carboxamide

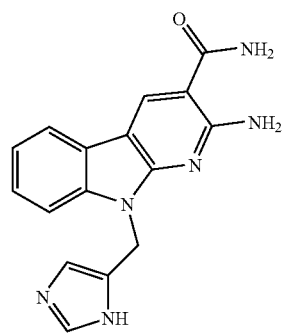

37
2-amino-9-(1H-imidazol-5-ylmethyl))-9H-pyrido[2,3-b]indole-3-carboxamide

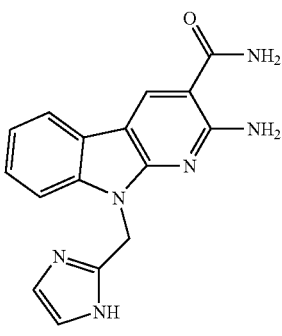

38
2-amino-9-(1H-imidazol-2-ylmethyl)-9H-pyrido[2,3-b]indole-3-carboxamide

TABLE 1-continued

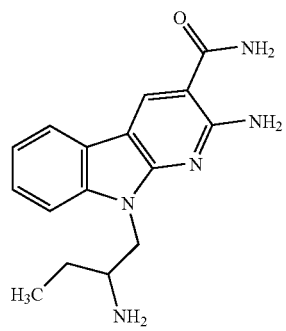

39
2-amino-9-(2-aminobutyl)-9H-pyrido[2,3-b]indole-3-carboxamide

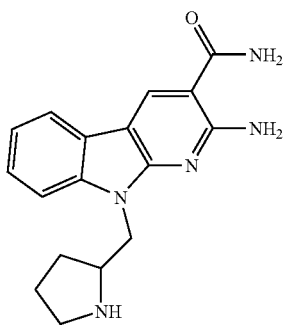

40
2-amino-9-(pyrrolidin-2-ylmethyl)-9H-pyrido[2,3-b]indole-3-carboxamide

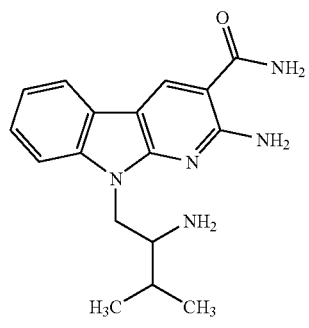

41
2-amino-9-(2-amino-3-methylbutyl)-9H-pyrido[2,3-b]indole-3-carboxamide

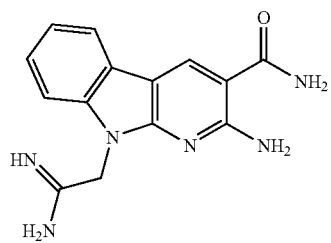

42
2-amino-9-(2-amino-2-iminoethyl)-9H-pyrido[2,3-b]indole-3-carboxamide

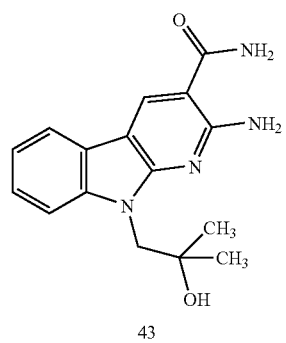

43
2-amino-9-(2-hydroxy-2-methylpropyl)-9H-pyrido[2,3-b]indole-3-carboxamide

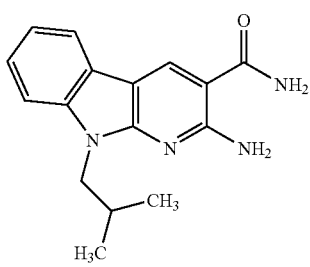

44
2-amino-9-isobutyl-9H-pyrido[2,3-b]indole-3-carboxamide

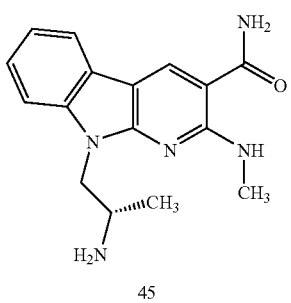

45
9-[(2S)-2-aminopropyl]-2-(methylamino)-9H-pyrido[2,3-b]indole-3-carboxamide

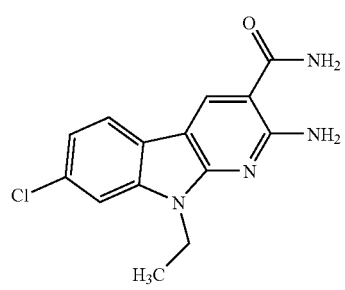

46
2-amino-7-chloro-9-ethyl-9H-pyrido[2,3-b]indole-3-carboxamide

TABLE 1-continued

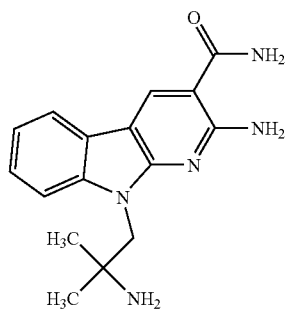

47
2-amino-9-(2-amino-2-methylpropyl)-9H-pyrido[2,3-b]indole-3-carboxamide

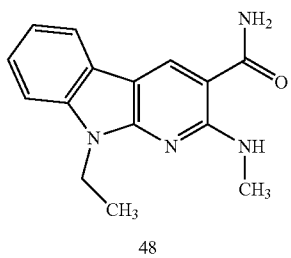

48
9-ethyl-2-(methylamino)-9H-pyrido[2,3-b]indole-3-carboxamide

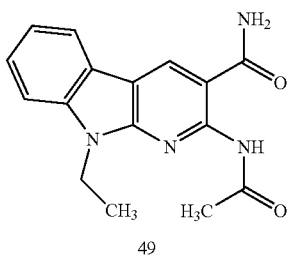

49
2-(acetylamino)-9-ethyl-9H-pyrido[2,3-b]indole-3-carboxamide

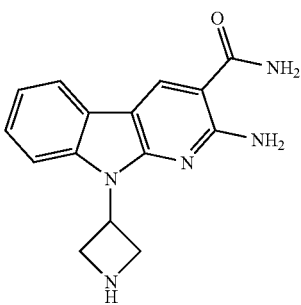

50
2-amino-9-azetidin-3-yl-9H-pyrido[2,3-b]indole-3-carboxamide

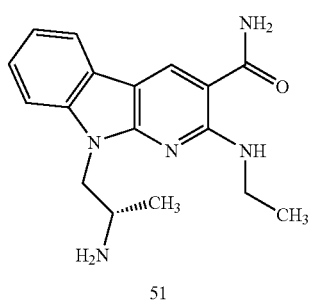

51
9-[(2S)-2-aminopropyl]-2-(ethylamino)-9H-pyrido[2,3-b]indole-3-carboxamide

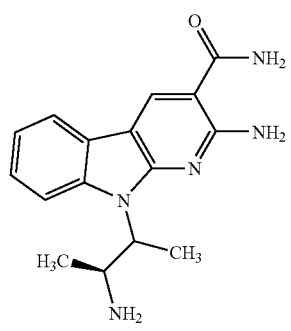

52
2-amino-9-[(2S)-2-amino-1-methylpropyl]-9H-pyrido[2,3-b]indole-3-carboxamide

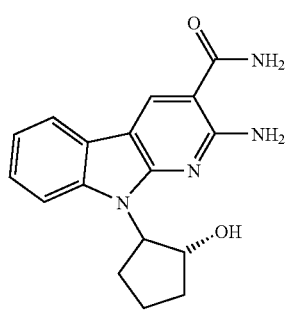

53
2-amino-9-[(2R)-2-hydroxycyclopentyl]-9H-pyrido[2,3-b]indole-3-carboxamide

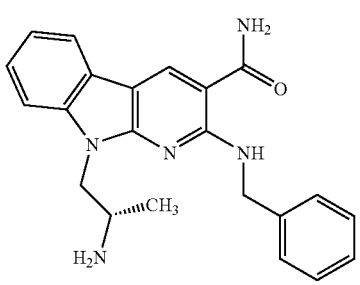

54
9-[(2S)-2-aminopropyl]-2-(benzylamino)-9H-pyrido[2,3-b]indole-3-carboxamide

TABLE 1-continued

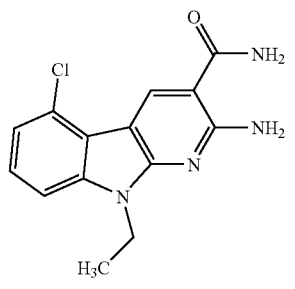

55
2-amino-5-chloro-9-ethyl-9H-pyrido[2,3-b]indole-3-carboxamide

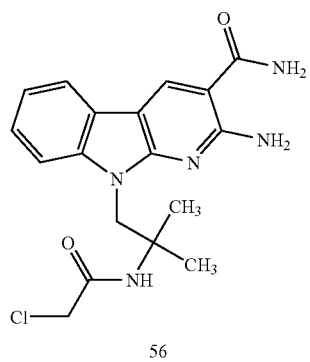

56
2-amino-9-{2-[(chloroacetyl)amino]-2-methylpropyl}-9H-pyrido[2,3-b]indole-3-carboxamide

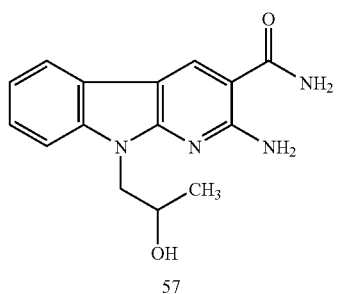

57
2-amino-9-(2-hydroxypropyl)-9H-pyrido[2,3-b]indole-3-carboxamide

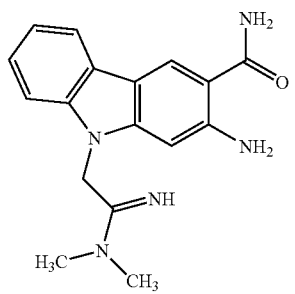

58
2-amino-9-[2-(dimethylamino)-2-iminoethyl]-9H-pyrido[2,3-b]indole-3-carboxamide

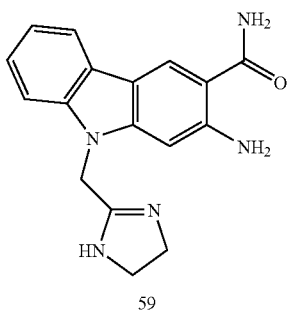

59
2-amino-9-(4,5-dihydro-1H-imidazol-2-ylmethyl)-9H-pyrido[2,3-b]indole-3-carboxamide

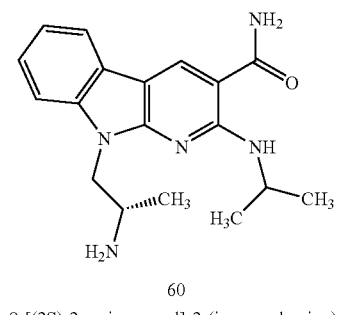

60
9-[(2S)-2-aminopropyl]-2-(isopropylamino)-9H-pyrido[2,3-b]indole-3-carboxamide TABLE 1-continued

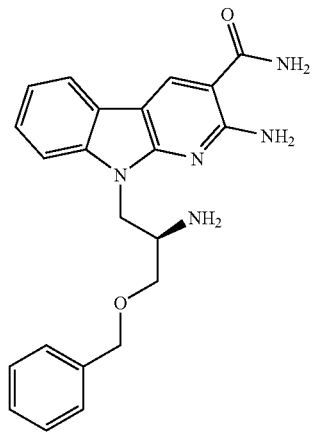

61
2-amino-9-[(2R)-2-amino-3-
(benzyloxy)propyl]-9H-pyrido[2,3-b]indole-
3-carboxamide

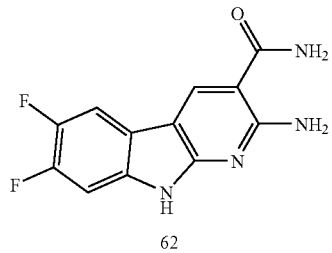

62
2-amino-6,7-difluoro-9H-pyrido[2,3-
b]indole-3-carboxamide

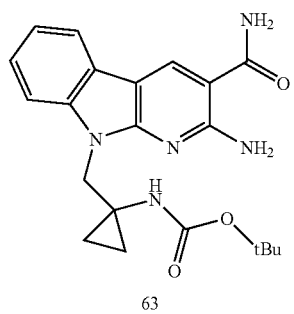

63
tert-butyl (1-{[2-amino-3-(aminocarbonyl)-
9H-pyrido[2,3-b]indol-9-
yl]methyl}cyclopropyl)carbamate

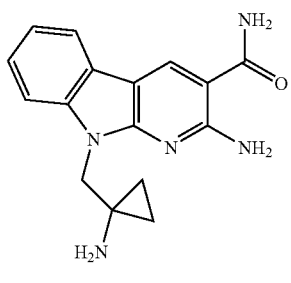

64
2-amino-9-[(1-aminocyclopropyl)methyl]-
9H-pyrido[2,3-b]indole-3-carboxamide

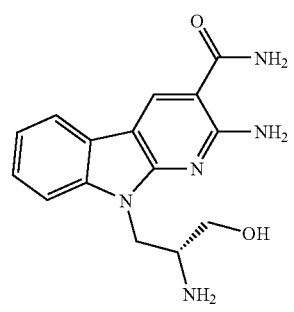

65
2-amino-9-[(2R)-2-amino-3-hydroxypropyl]-
9H-pyrido[2,3-b]indole-3-carboxamide

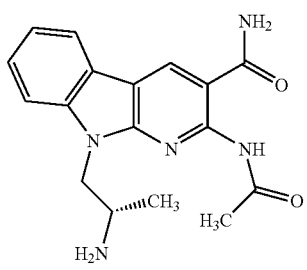

66
2-(acetylamino)-9-[(2S)-2-aminopropyl]-9H-
pyrido[2,3-b]indole-3-carboxamide

TABLE 1-continued

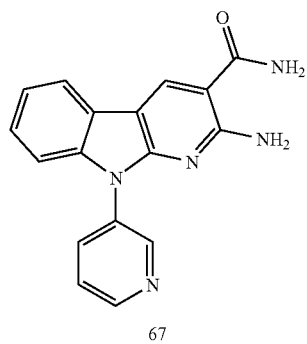

67
2-amino-9-pyridin-3-yl-9H-pyrido[2,3-b]indole-3-carboxamide

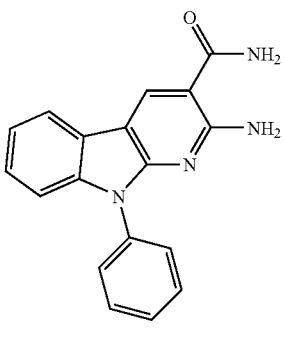

68
2-amino-9-phenyl-9H-pyrido[2,3-b]indole-3-carboxamide

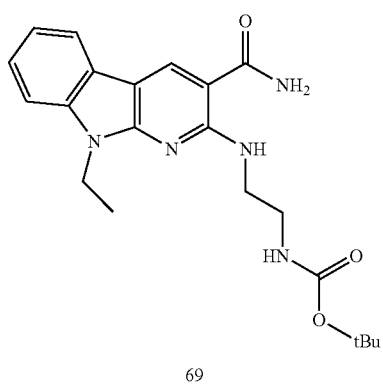

69
tert-butyl (2-{[3-(aminocarbonyl)-9-ethyl-9H-pyrido[2,3-b]indol-2-yl]amino}ethyl)carbamate

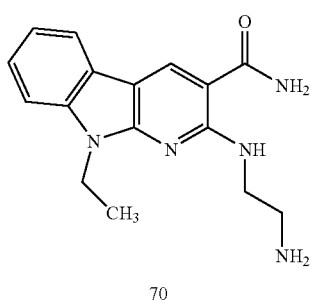

70
2-[(2-aminoethyl)amino]-9-ethyl-9H-pyrido[2,3-b]indole-3-carboxamide

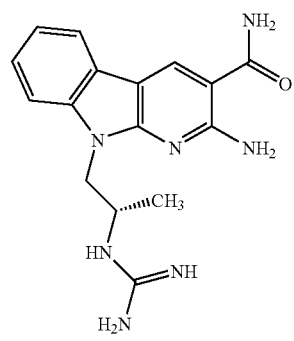

71
2-amino-9-((2S)-2-{[amino(imino)methyl]amino}propyl)-9H-pyrido[2,3-b]indole-3-carboxamide

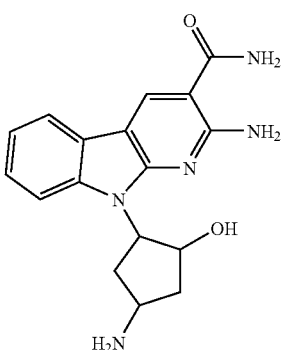

72
2-amino-9-(4-amino-2-hydroxycyclopentyl)-9H-pyrido[2,3-b]indole-3carboxamide

TABLE 1-continued

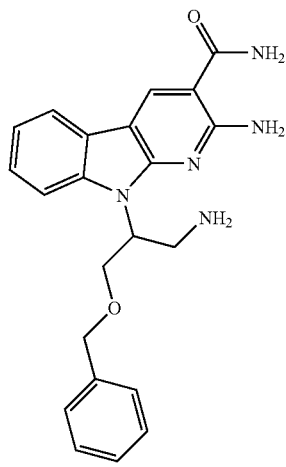

73
2-amino-9-{2-amino-1-[(benzyloxy)methyl]ethyl}-9H-pyrido[2,3-b]indole-3-carboxamide

4. General Synthetic Methods and Intermediates

The compounds of this invention may be prepared in general by methods illustrated by the general schemes and by the preparative examples that are described in the Experimental Procedures herein. Scheme I, as shown in the Experimental Procedures, depicts the general synthesis of compounds of formula I from the 2-cyanoacrylamide intermediate. Schemes II-VI more particularly depict the synthesis of certain exemplary compounds of the invention.

Accordingly, in another aspect of the invention, a process for the synthesis of compounds of formula I is provided:

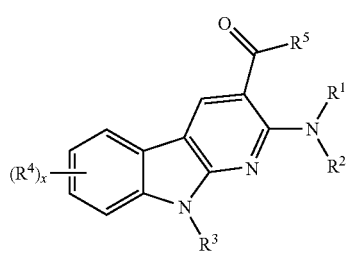

or a pharmaceutically acceptable salt thereof wherein,
$R^1$ is hydrogen, $C_1$-$C_4$aliphatic, —C(O)N($R^{1a}$)$_2$, —C(O)$R^{1b}$, or —(CH$_2$)$_n$$R^{1c}$,
wherein each occurrence of $R^{1a}$ is independently hydrogen, C(O)O$R^{1d}$, or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of $R^{1a}$ are taken together with a nitrogen atom to which they are bound to form an optionally substituted 3-7-membered heterocyclyl ring;
$R^{1b}$ is an optionally substituted group selected from $C_1$-$C_6$aliphatic or phenyl;

$R^{1c}$ is —N($R^{1a}$)$_2$, or an optionally substituted phenyl or pyridyl group;
$R^{1d}$ is $C_1$-$C_6$aliphatic; and
n is 1, 2 or 3;
$R^2$ is hydrogen or $C_1$-$C_4$aliphatic;
$R^3$ is —H, -$T_1$-$R^{3d}$, —$V_1$—$R^{3a}$, —$V_1$-$T_1$-$R^{3d}$, or —$R^{3e}$, wherein
$V_1$ is —C(O)—, —S(O)$_2$—, —C(O)N$R^{3a}$—, or —S(O)$_2$N$R^{3a}$—;
$T_1$ is a $C_1$-$C_6$alkylene chain optionally substituted with one or more independent occurrences of —$R^{3b}$, wherein the alkylene chain optionally is interrupted by —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')S(O)$_2$N(R')—, —OC(O)—, or —C(O)N(R')—O— or wherein $T_1$ or a portion thereof optionally forms part of an optionally substituted 3-7 membered cycloaliphatic or heterocyclyl ring;
each occurrence of $R^{3a}$ is independently hydrogen or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of $R^{3a}$ are taken together with a nitrogen atom to which they are bound to form an optionally substituted 3-7-membered heterocyclyl ring;
each occurrence of $R^{3b}$ is independently halogen, —CN, —NO$_2$, —$R^{3c}$, —N($R^{3a}$)$_2$, —O$R^{3a}$, —S$R^{3c}$, —S(O)$_2$$R^{3c}$, —C(O)$R^{3a}$, —C(O)O$R^{3a}$, —C(O)N($R^{3a}$)$_2$, —S(O)$_2$N($R^{3a}$)$_2$, —OC(O)N($R^{3a}$)$_2$, —N(R')C(O)$R^{3a}$, —N(R')SO$_2$$R^{3c}$, —N(R')C(O)O$R^{3a}$, —N(R')C(O)N($R^{3a}$)$_2$, —N(R')SO$_2$N($R^{3a}$)$_2$, —N$R^{3a}$(C=N$R^{3a}$)N($R^{3a}$)$_2$, =N$R^{3a}$, =N—N($R^{3a}$)$_2$, =N—O$R^{3a}$, =N—NHC(O)$R^{3a}$, =N—NHCO$_2$$R^{3a}$, =N—NHSO$_2$$R^{3a}$, or two occurrences of $R^{3a}$ or $R^{3c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur;

each occurrence of $R^{3c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3e}$ is independently an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur and each R' is independently hydrogen or optionally substituted $C_{1-6}$aliphatic;

x is 0-4;

each occurrence of $R^4$ is independently —$R^{4a}$, -$T_2$-$R^{4d}$, —$V_2$-$T_2$-$R^{4d}$, wherein:

each occurrence of $R^{4a}$ is independently halogen, —CN, —$NO_2$, —$R^{4c}$, —$N(R^{4b})_2$, —$OR^{4b}$, —$SR^{4c}$, —$S(O)_2R^{4c}$, —$C(O)R^{4b}$, —$C(O)OR^{4b}$, —$C(O)N(R^{4b})_2$, —$S(O)_2N(R^{4b})_2$, —$OC(O)N(R^{4b})_2$, —$N(R')C(O)R^{4b}$, —$N(R')SO_2R^{4c}$, —$N(R')C(O)OR^{4b}$, —$N(R')C(O)N(R^{4b})_2$, or —$N(R')SO_2N(R^{4b})_2$, or two occurrences of $R^{4b}$ or $R^{4c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur, or two occurrences of $R^{4b}$, taken together with a nitrogen atom to which they are bound, form an optionally substituted 3-7-membered heterocyclyl ring having 0-3 additional heteroatoms selected from nitrogen, oxygen, or sulfur;

each occurrence of $R^{4b}$ is independently hydrogen or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4c}$ is independently an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $V_2$ is independently —C(R')=C(R')—, —C≡C—, —N(R')—, —O—, —S—, —S(O)—, —$S(O)_2$—, —C(O)—, —C(O)O—, —C(O)N(R')—, —$S(O)_2$N(R')—, —OC(O)N(R')—, —N(R')C(O)—, —N(R')$SO_2$—, —N(R')C(O)O—, —NR'C(O)N(R')—, —N(R')$SO_2$N(R')—, —OC(O)—, or —C(O)N(R')—O—; and each occurrence of $T_2$ is independently a $C_1$-$C_6$alkylene chain optionally substituted with $R^{4a}$, wherein the alkylene chain optionally is interrupted by —C(R')=C(R')—, —C≡C—, —N(R')—, —O—, —S—, —S(O)—, —$S(O)_2$—, —C(O)—, —C(O)O—, —C(O)N(R')—, —$S(O)_2$N(R')—, —OC(O)N(R')—, —N(R')C(O)—, —N(R')$SO_2$—, —N(R')C(O)O—, —NR'C(O)N(R')—, —N(R')$SO_2$N(R')—, —OC(O)—, or —C(O)N(R')—O— or wherein $T_2$ or a portion thereof optionally forms part of an optionally substituted 3-7 membered cycloaliphatic or heterocyclyl ring, and $R^5$ is —$NR^6R^7$ or —OH, wherein:
$R^6$ and $R^7$ are each independently hydrogen or $C_1$-$C_4$aliphatic;

provided that the compound of formula I is other than:
a) 2-amino-9-ethyl-9H-Pyrido[2,3-b]indole-3-carboxamide;
b) 2-amino-1H-Pyrido[2,3-b]indole-3-carboxamide, or the monohydrochloride thereof,
c) 2-amino-1H-Pyrido[2,3-b]indole-3-carboxylic acid; or
d) 2-amino-9-(2,6-dichlorophenyl)-9H-Pyrido[2,3-b]indole-3-carboxamide, wherein the process comprises contacting an intermediate of formula II with an amine NHR$^1$R$^2$ under suitable reaction conditions, wherein:

$R^1$ is hydrogen, $C_1$-$C_4$aliphatic, —C(O)N(R$^{1a}$)$_2$, —C(O)R$^{1b}$, or —(CH$_2$)$_n$R$^{1c}$, wherein each occurrence of $R^{1a}$ is independently hydrogen, C(O)OR$^{1d}$, or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of $R^{1a}$ are taken together with a nitrogen atom to which they are bound to form an optionally substituted 3-7-membered heterocyclyl ring;

$R^{1b}$ is an optionally substituted group selected from $C_1$-$C_6$aliphatic or phenyl;

$R^{1c}$ is —N(R$^{1a}$)$_2$, or an optionally substituted phenyl or pyridyl group;

$R^{1d}$ it is $C_1$-$C_6$aliphatic; and n is 1, 2, or 3;

$R^2$ is hydrogen or $C_1$-$C_4$aliphatic; and the intermediate of formula II has the structure:

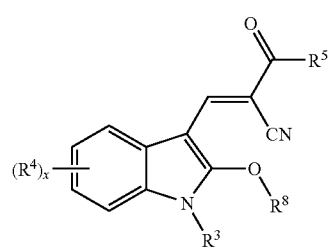

II wherein:
$R^3$ is —H, -$T_1$-$R^{3d}$, —$V_1$-$T_1$-$R^{3d}$, or —$R^{3c}$, wherein
$V_1$ is —C(O)—, —S(O)$_2$—, —C(O)NR$^{3a}$—, or —S(O)$_2$NR$^{3a}$—;
$T_1$ is a $C_1$-$C_6$alkylene chain optionally substituted with one or more independent occurrences of —$R^{3b}$, wherein the alkylene chain optionally is interrupted by —C(R')═C(R')—, —C≡C—, —N(R')—, —O—, —S—, —S(O)—, —S(O)₂—, —C(O)—, —C(O)O—, —C(O)N(R')—, —S(O)₂N(R')—, —OC(O)N(R')—, —N(R')C(O)—, —N(R')SO₂—, —N(R')C(O)O—, —NR'C(O)N(R')—, —N(R')S(O)₂N(R')—, —OC(O)—, or —C(O)N(R')—O— or wherein T₁ or a portion thereof optionally forms part of an optionally substituted 3-7 membered cycloaliphatic or heterocyclyl ring;

each occurrence of $R^{3a}$ is independently hydrogen or an optionally substituted group selected from $C_1$-$C_6$ aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of $R^{3a}$ are taken together with a nitrogen atom to which they are bound to form an optionally substituted 3-7-membered heterocyclyl ring;

each occurrence of $R^{3b}$ is independently halogen, —CN, —NO₂, —$R^{3c}$, —N($R^{3a}$)₂, —O$R^{3a}$, —S$R^{3c}$, —S(O)₂$R^{3c}$, —C(O)$R^{3a}$, —C(O)O$R^{3a}$, —C(O)N($R^{3a}$)₂, —S(O)₂N($R^{3a}$)₂, —OC(O)N($R^{3a}$)₂, —N(R')C(O)$R^{3a}$, —N(R')SO₂$R^{3c}$, —N(R')C(O)O$R^{3a}$, —N(R')C(O)N($R^{3a}$)₂, —N(R')SO₂N($R^{3a}$)₂, —NR$^{3a}$(C═NR$^{3a}$)N($R^{3a}$)₂, ═NR$^{3a}$, ═N—N($R^{3a}$)₂, ═N—O$R^{3a}$, ═N—NHC(O)$R^{3a}$, ═N—NHCO₂$R^{3a}$, ═N—NHSO₂$R^{3a}$, or two occurrences of $R^{3a}$ or $R^{3c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur;

each occurrence of $R^{3c}$ is independently an optionally substituted group selected from $C_{1-6}$ aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3e}$ is independently an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur and each R' is independently hydrogen or optionally substituted $C_{1-6}$ aliphatic;

x is 0-4;

each occurrence of $R^4$ is independently —$R^{4a}$, -$T_2$-$R^{4d}$, or —$V_2$-$T_2$-$R^{4d}$, wherein:

each occurrence of $R^{4a}$ is independently halogen, —CN, —NO₂, —$R^{4c}$, —N($R^{4b}$)₂, —O$R^{4b}$, —S$R^{4c}$, —S(O)₂$R^{4c}$, —C(O)$R^{4b}$, —C(O)O$R^{4b}$, —C(O)N($R^{4b}$)₂, —S(O)₂N($R^{4b}$)₂, —OC(O)N($R^{4b}$)₂, —N(R')C(O)$R^{4b}$, —N(R')SO₂$R^{4c}$, —N(R')C(O)O$R^{4b}$, —N(R')C(O)N($R^{4b}$)₂, or —N(R')SO₂N($R^{4b}$)₂, or two occurrences of $R^{4b}$ or $R^{4c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur, or two occurrences of $R^{4b}$, taken together with a nitrogen atom to which they are bound, form an optionally substituted 3-7-membered heterocyclyl ring having 0-3 additional heteroatoms selected from nitrogen, oxygen, or sulfur;

each occurrence of $R^{4b}$ is independently hydrogen or an optionally substituted group selected from $C_1$-$C_6$ aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4c}$ is independently an optionally substituted group selected from $C_1$-$C_6$ aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $V_2$ is independently —C(R')═C(R')—, —C≡C—, —N(R')—, —O—, —S—, —S(O)—, —S(O)₂—, —C(O)—, —C(O)O—, —C(O)N(R')—, —S(O)₂N(R')—, —OC(O)N(R')—, —N(R')C(O)—, —N(R')C(O)O—, —NR'C(O)N(R')—, —N(R')SO₂N(R')—, —OC(O)—, or —C(O)N(R')—O—;

each occurrence of $T_2$ is independently a $C_1$-$C_6$ alkylene chain optionally substituted with $R^{4a}$, wherein the alkylene chain optionally is interrupted by —C(R')═C(R')—, —C≡C—, —N(R')—, —O—, —S—, —S(O)—, —S(O)₂—, —C(O)—, —C(O)O—, —C(O)N(R')—, —S(O)₂N(R')—, —OC(O)N(R')—, —N(R')C(O)—, —N(R')SO₂—, —N(R')C(O)O—, —NR'C(O)N(R')—, —N(R')SO₂N(R')—, —OC(O)—, or —C(O)N(R')—O— or wherein $T_2$ or a portion thereof optionally forms part of an optionally substituted 3-7 membered cycloaliphatic or heterocyclyl ring;

$R^5$ is —NR$^6$R$^7$ or —OH, wherein:

$R^6$ and $R^7$ are each independently hydrogen or $C_1$-$C_4$ aliphatic; and $R^8$ is $C_1$-$C_4$ alkyl;

provided that the intermediate of formula II is other than:

a) 2-cyano-3-(2-ethoxy-1-ethyl-1H-indol-3-yl)-2-Propenamide, b) 2-cyano-3-(2-methoxy-1H-indol-3-yl)-2-Propenamide, or c) 2-cyano-3-[1-(2,6-dichlorophenyl)-2-ethoxy-1H-indol-3-yl]-2-Propenamide.

In yet another aspect of the invention, a process for the synthesis of compounds of formula I-A is provided:

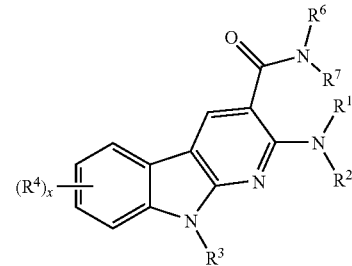

I-A wherein:

$R^1$ is hydrogen or $C_1$-$C_4$ aliphatic;

$R^2$ is hydrogen or $C_1$-$C_4$ aliphatic;

R³ is —H, -T₁-R³ᵈ, —V₁—R³ᵃ, —V₁-T₁-R³ᵈ, or —R³ᵉ, wherein

V₁ is —C(O)—, —S(O)₂—, —C(O)NR³ᵃ—, or —S(O)₂NR³ᵃ—;

T₁ is a C₁-C₆alkylene chain optionally substituted with one or more independent occurrences of —R³ᵇ, wherein the alkylene chain optionally is interrupted by —C(R')═C(R')—, —C≡C—, —N(R')—, —O—, —S—, —S(O)—, —S(O)₂—, —C(O)—, —C(O)O—, —C(O)N(R')—, —S(O)₂N(R')—, —OC(O)N(R')—, —N(R')C(O)—, —N(R')SO₂—, —N(R')C(O)O—, —NR'C(O)N(R')—, —N(R')S(O)₂N(R')—, —OC(O)—, or —C(O)N(R')—O— or wherein T₁ or a portion thereof optionally forms part of an optionally substituted 3-7 membered cycloaliphatic or heterocyclyl ring;

each occurrence of R³ᵃ is independently hydrogen or an optionally substituted group selected from C₁-C₆aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of R³ᵃ are taken together with a nitrogen atom to which they are bound to form an optionally substituted 3-7-membered heterocyclyl ring;

each occurrence of —R³ᵇ is independently halogen, —CN, —NO₂, —R³ᶜ, —N(R³ᵃ)₂, —OR³ᵃ, —SR³ᶜ, —S(O)₂R³ᶜ, —C(O)R³ᵃ, —C(O)OR³ᵃ, —C(O)N(R³ᵃ)₂, —S(O)₂N(R³ᵃ)₂, —OC(O)N(R³ᵃ)₂, —N(R')C(O)R³ᵃ, —N(R')SO₂R³ᶜ, —N(R')C(O)OR³ᵃ, —N(R')C(O)N(R³ᵃ)₂, or —N(R')SO₂N(R³ᵃ)₂, or two occurrences of R³ᵃ or R³ᶜ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur;

each occurrence of R³ᶜ is independently an optionally substituted group selected from C₁₋₆aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R³ᵈ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R³ᵉ is independently an optionally substituted group selected from 3-10-membered cycloaliphatic, or 3-10-membered heterocyclyl having 1-5 heteroatoms independently selected from nitrogen, oxygen, or sulfur; and each R' is independently hydrogen or optionally substituted C₁₋₆aliphatic;

x is 0-4;

each occurrence of R⁴ is independently —R⁴ᵃ, -T₂-R⁴ᵈ, or —V₂-T₂-R⁴ᵈ, wherein:

each occurrence of —R⁴ᵃ is independently halogen, —CN, —NO₂, —R⁴ᵉ, —N(R⁴ᵇ)₂, —OR⁴ᵇ, —SR⁴ᶜ, —S(O)₂R⁴ᶜ, —C(O)R⁴ᵇ, —C(O)OR⁴ᵇ, —C(O)N(R⁴ᵇ)₂, —S(O)₂N(R⁴ᵇ)₂, —OC(O)N(R⁴ᵇ)₂, —N(R')C(O)R⁴ᵇ, —N(R')SO₂R⁴ᶜ, —N(R')C(O)OR⁴ᵇ, —N(R')C(O)N(R⁴ᵇ)₂, or —N(R')SO²N(R⁴ᵇ)², or two occurrences of R⁴ᵇ or R⁴ᶜ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur, or two occurrences of R⁴ᵇ, taken together with a nitrogen atom to which they are bound, form an optionally substituted 3-7-membered heterocyclyl ring having 0-3 additional heteroatoms selected from nitrogen, oxygen, or sulfur;

each occurrence of R⁴ᵇ is independently hydrogen or an optionally substituted group selected from C₁-C₆aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R⁴ᶜ is independently an optionally substituted group selected from C₁-C₆aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R⁴ᵈ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of V₂ is independently —C(R')═C(R')—, —C≡C—, —N(R')—, —O—, —S—, —S(O)—, —S(O)₂—, —C(O)—, —C(O)O—, —C(O)N(R')—, —S(O)₂N(R')—, —OC(O)N(R')—, —N(R')C(O)—, —N(R')SO₂—, —N(R')C(O)O—, —NR'C(O)N(R')—, —N(R')SO₂N(R')—, —OC(O)—, or —C(O)N(R')—O—; and each occurrence of T₂ is independently a C₁-C₆alkylene chain optionally substituted with R⁴ᵃ, wherein the alkylene chain optionally is interrupted by —C(R')═C(R')—, —C≡C—, —N(R')—, —O—, —S—, —S(O)—, —S(O)₂—, —C(O)—, —C(O)O—, —C(O)N(R')—, —S(O)₂N(R')—, —OC(O)N(R')—, —N(R')C(O)—, —N(R')SO₂—, —N(R')C(O)O—, —NR'C(O)N(R')—, —N(R')SO₂N(R')—, —OC(O)—, or —C(O)N(R')—O— or wherein T₂ or a portion thereof optionally forms part of an optionally substituted 3-7 membered cycloaliphatic or heterocyclyl ring, and R⁶ and R⁷ are each independently hydrogen or C₁-C₄aliphatic;

provided that the compound of formula I is other than:
a) 2-amino-9-ethyl-9H-Pyrido[2,3-b]indole-3-carboxamide; or
b) 2-amino-1H-Pyrido[2,3-b]indole-3-carboxamide, or the monohydrochloride thereof, wherein the process comprises contacting an intermediate of formula II-A with an amine NHR¹R² under suitable reaction conditions, wherein:

R¹ is hydrogen, or C₁-C₄aliphatic, and each occurrence of Rʰ is independently hydrogen or C₁-C₄aliphatic;

R² is hydrogen or C₁-C₄aliphatic; and the intermediate of formula II-A has the structure:

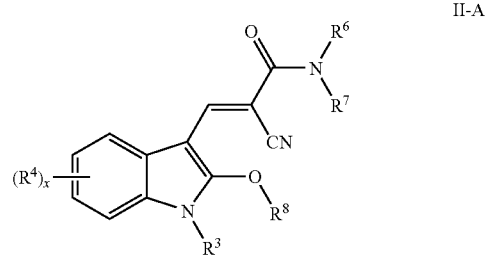

II-A wherein:
R³ is —H, -T₁-R³ᵈ, —V₁—R³ᵃ, —V₁-T₁-R³ᵈ, or —R³ᵉ, and $V_1$ is —C(O)—, —S(O)$_2$—, —C(O)NR$^{3a}$—, or —S(O)$_2$NR$^{3a}$—;

$T_1$ is a C$_1$-C$_6$alkylene chain optionally substituted with one or more independent occurrences of —R$^{3b}$, wherein the alkylene chain optionally is interrupted by —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')S(O)$_2$N(R')—, —OC(O)—, or —C(O)N(R')—O— or wherein $T_1$ or a portion thereof optionally forms part of an optionally substituted 3-7 membered cycloaliphatic or heterocyclyl ring;

each occurrence of R$^{3a}$ is independently hydrogen or an optionally substituted group selected from C$_1$-C$_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of R$^{3a}$ are taken together with a nitrogen atom to which they are bound to form an optionally substituted 3-7-membered heterocyclyl ring;

each occurrence of R$^{3b}$ is independently halogen, —CN, —NO$_2$, —R$^{3c}$, —N(R$^{3a}$)$_2$, —OR$^{3a}$, —SR$^{3c}$, —S(O)$_2$R$^{3c}$, —C(O)R$^{3a}$, —C(O)OR$^{3a}$, —C(O)N(R$^{3a}$)$_2$, —S(O)$_2$N(R$^{3a}$)$_2$, —OC(O)N(R$^{3a}$)$_2$, —N(R')C(O)R$^{3a}$, —N(R')SO$_2$R$^{3c}$, —N(R')C(O)OR$^{3a}$, —N(R')C(O)N(R$^{3a}$)$_2$, or —N(R')SO$_2$N(R$^{3a}$)$_2$, or two occurrences of R$^{1a}$ or R$^{3c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur;

each occurrence of R$^{3c}$ is independently an optionally substituted group selected from C$_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{3d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and each occurrence of R$^{3e}$ is independently an optionally substituted group selected from 3-10-membered cycloaliphatic, or 3-10-membered heterocyclyl having 1-5 heteroatoms independently selected from nitrogen, oxygen, or sulfur;

each —R' is independently hydrogen or optionally substituted C$_{1-6}$aliphatic;

x is 0-4;

each occurrence of R$^4$ is independently —R$^{4a}$, -T$_2$-R$^{4d}$, or —V$_2$-T$_2$R$^{4d}$, wherein:

each occurrence of R$^{4a}$ is independently halogen, —CN, —NO$_2$, —R$^{4c}$, —N(R$^{4b}$)$_2$, —OR$^{4b}$, —SR$^{4c}$, —S(O)$_2$R$^{4c}$, —C(O)R$^{4b}$, —C(O)OR$^{4b}$, —C(O)N(R$^{4b}$)$_2$, —S(O)$_2$N(R$^{4b}$)$_2$, —OC(O)N(R$^{4b}$)$_2$, —N(R')C(O)R$^{4b}$, —N(R')SO$_2$R$^{4c}$, —N(R')C(O)OR$^{4b}$, —N(R')C(O)N(R$^{4b}$)$_2$, or —N(R')SO$_2$N(R$^{4b}$)$_2$, or two occurrences of R$^{4b}$ or R$^{4c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur, or two occurrences of R$^{4b}$, taken together with a nitrogen atom to which they are bound, form an optionally substituted 3-7-membered heterocyclyl ring having 0-3 additional heteroatoms selected from nitrogen, oxygen, or sulfur;

each occurrence of R$^{4b}$ is independently hydrogen or an optionally substituted group selected from C$_1$-C$_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{4c}$ is independently an optionally substituted group selected from C$_1$-C$_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{4d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of V$_2$ is independently —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O—;

each occurrence of T$_2$ is independently a C$_1$-C$_6$alkylene chain optionally substituted with R$^{4a}$, wherein the alkylene chain optionally is interrupted by —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O— or wherein T$_2$ or a portion thereof optionally forms part of an optionally substituted 3-7 membered cycloaliphatic or heterocyclyl ring;

R$^6$ and R$^7$ are each independently hydrogen or C$_1$-C$_4$aliphatic; and

R$^8$ is C$_1$-C$_4$alkyl;

provided that the intermediate of formula II-A is other than:

a) 2-cyano-3-(2-ethoxy-1-ethyl-1H-indol-3-yl)-2-Propenamide, or b) 2-cyano-3-(2-methoxy-1H-indol-3-yl)-2-Propenamide.

In some embodiments for the process described directly above:

R$^1$ and R$^2$ are each hydrogen;

R$^3$ is -T$_1$-R$^{3d}$,

T$_1$ is a C$_1$-C$_4$alkylene chain wherein the alkylene chain is optionally substituted by 1 or 2 independent occurrences of —R$^{3b}$, and the alkylene chain is optionally interrupted by —C(R')=C(R')—, —N(R')—, —O—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')S(O)$_2$N(R')—, —OC(O)—, or —C(O)N(R')—O—;

R$^{3d}$ is hydrogen;

each occurrence of R$^{3b}$ is independently —C$_1$-C$_3$aliphatic, —N(R$^{3a}$)$_2$, —OR$^{3a}$, —C(O)OR$^{3a}$, —C(O)N(R$^{3a}$)$_2$, —S(O)$_2$N(R$^{3a}$)$_2$, —OC(O)N(R$^{3a}$)$_2$, —N(R')C(O)R$^{3a}$, —N(R')SO$_2$R$^{3c}$, —N(R')C(O)OR$^{3a}$, —N(R')C(O)N(R$^{3a}$)$_2$, or —N(R')SO$_2$N(R$^{3a}$)$_2$;

x is 0, 1, or 2; and each occurrence of $R^4$ is independently halogen, —CN, —$NO_2$, —$R^{4c}$, —$N(R^{4b})_2$, —$OR^{4b}$, —$SR^{4c}$, —$S(O)_2R^{4c}$, —$C(O)R^{4b}$, —$C(O)OR^{4b}$, —$C(O)N(R^{4b})_2$, —$S(O)_2N(R^{4b})_2$, —$N(R')C(O)R^{4b}$, or —$N(R')SO_2R^{4c}$.

In other embodiments for the process described above, $R^4$ is halogen or —$C_1$-$C_3$alkyl.

In still other embodiments for the process described above, $T_1$ is $C_1$-$C_4$alkyl substituted with 1 or 2 independent occurrences of —$R^{3b}$, wherein each occurrence of —$R^{3b}$ is independently —$N(R^{3a})_2$, —$OR^{3a}$, or —$C_1$-$C_3$alkyl.

In yet another aspect of the invention, an intermediate of formula II is provided:

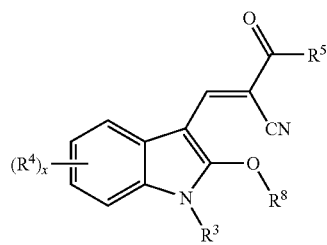

II wherein:

$R^3$ is —H, -$T_1$-$R^{3d}$, —$V_1$—$R^{3a}$, —$V_1$-$T_1$-$R^{3d}$, or —$R^{3e}$, wherein $V_1$ is —C(O)—, —$S(O)_2$—, —$C(O)NR^{3a}$—, or —$S(O)_2NR^{3a}$—;

$T_1$ is a $C_1$-$C_6$alkylene chain optionally substituted with one or more independent occurrences of —$R^{3b}$, wherein the alkylene chain optionally is interrupted by —C(R')=C(R')—, —C≡C—, —N(R')—, —O—, —S—, —S(O)—, —S(O)_2—, —C(O)—, —C(O)O—, —C(O)N(R')—, —$S(O)_2N(R')$—, —OC(O)N(R')—, —N(R')C(O)—, —$N(R')SO_2$—, —N(R')C(O)O—, —NR'C(O)N(R')—, —$N(R')S(O)_2N(R')$—, —OC(O)—, or —C(O)N(R')—O— or wherein $T_1$ or a portion thereof optionally forms part of an optionally substituted 3-7 membered cycloaliphatic or heterocyclyl ring;

each occurrence of $R^{3a}$ is independently hydrogen or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of $R^{3a}$ are taken together with a nitrogen atom to which they are bound to form an optionally substituted 3-7-membered heterocyclyl ring;

each occurrence of $R^{3b}$ is independently halogen, —CN, —$NO_2$, —$R^{3c}$, —$N(R^{3a})_2$, —$OR^{3a}$, —$SR^{3c}$, —$S(O)_2R^{3c}$, —$C(O)R^{3a}$, —$C(O)OR^{3a}$, —$C(O)N(R^{3a})_2$, —$S(O)_2N(R^{3a})_2$, —$OC(O)N(R^{3a})_2$, —$N(R')C(O)R^{3a}$, —$N(R')SO_2R^{3c}$, —$N(R')C(O)OR^{3a}$, —$N(R')C(O)N(R^{3a})_2$, —$N(R')SO_2N(R^{3a})_2$, —$NR^{3a}(C$=$NR^{3a})N(R^{3a})_2$, =$NR^{3a}$, =N—$N(R^{3a})_2$, =N—$OR^{3a}$, =N—$NHC(O)R^{3a}$, =N—$NHCO_2R^{3a}$, =N—$NHSO_2R^{3a}$, or two occurrences of $R^{3a}$ or $R^{3c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur;

heteroaryl having 1-3 heteroatoms independently selected from nitrogen, oxygen, or sulfur;

each occurrence of $R^{3c}$ is independently an optionally substituted group selected from $C_{1-6}$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{3e}$ is independently an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur and each R' is independently hydrogen or optionally substituted $C_{1-6}$aliphatic;

x is 0-4;

each occurrence of $R^4$ is independently —$R^{4a}$, -$T_2$-$R^{4d}$, or —$V_2$-$T_2$-$R^{4d}$, wherein:

each occurrence of $R^{4a}$ is independently halogen, —CN, —$NO_2$, —$R^{4c}$, —$N(R^{4b})_2$, —$OR^{4b}$, —$SR^{4c}$, —$S(O)_2R^{4c}$, —$C(O)R^{4b}$, —$C(O)OR^{4b}$, —$C(O)N(R^{4b})_2$, —$S(O)_2N(R^{4b})_2$, —$OC(O)N(R^{4b})_2$, —$N(R')C(O)R^{4b}$, —$N(R')SO_2R^{4c}$, —$N(R')C(O)OR^{4b}$, —$N(R')C(O)N(R^{4b})_2$, or —$N(R')SO_2N(R^{4b})_2$, or two occurrences of $R^{4b}$ or $R^{4c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur, or two occurrences of $R^{4b}$, taken together with a nitrogen atom to which they are bound, form an optionally substituted 3-7-membered heterocyclyl ring having 0-3 additional heteroatoms selected from nitrogen, oxygen, or sulfur;

each occurrence of $R^{4b}$ is independently hydrogen or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4c}$ is independently an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $V_2$ is independently —C(R')=C(R')—, —C≡C—, —N(R')—, —O—, —S—, —S(O)—, —$S(O)_2$—, —C(O)—, —C(O)O—, —C(O)N(R')—, —$S(O)_2N(R')$—, —OC(O)N(R')—, —N(R')C(O)—, —$N(R')SO_2$—, —N(R')C(O)O—, —NR'C(O)N(R')—, —$N(R')SO_2N(R')$—, —OC(O)—, or —C(O)N(R')—O—;

each occurrence of $T_2$ is independently a $C_1$-$C_6$alkylene chain optionally substituted with $R^{4a}$, wherein the alkylene chain optionally is interrupted by —C(R')═C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O— or wherein T$_2$ or a portion thereof optionally forms part of an optionally substituted 3-7 membered cycloaliphatic or heterocyclyl ring;

R$^5$ is —NR$^6$R$^7$ or —OH, wherein:

R$^6$ and R$^7$ are each independently hydrogen or C$_1$-C$_4$aliphatic; and

R$^8$ is C$_1$-C$_4$alkyl;

provided that the intermediate of formula II is other than:

a) 2-cyano-3-(2-ethoxy-1-ethyl-1H-indol-3-yl)-2-Propenamide, b) 2-cyano-3-(2-methoxy-1H-indol-3-yl)-2-Propenamide, or c) 2-cyano-3-[1-(2,6-dichlorophenyl)-2-ethoxy-1H-indol-3-yl]-2-Propenamide.

In still another aspect of the invention, an intermediate of formula II-A is provided:

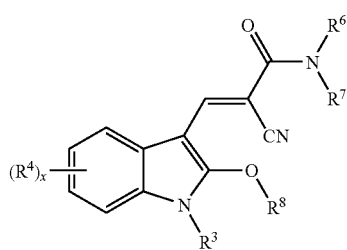

II-A wherein:

R$^3$ is —H, -T$_1$-R$^{3d}$, —V$_1$—R$^{3a}$, —V$_1$-T$_1$-R$^{3d}$, or —R$^{3e}$, and V$_1$ is —C(O)—, —S(O)$_2$—, —C(O)NR$^{3a}$—, or —S(O)$_2$NR$^{3a}$—;

T$_1$ is a C$_1$-C$_6$alkylene chain optionally substituted with one or more independent occurrences of —R$^{3b}$, wherein the alkylene chain optionally is interrupted by —C(R')═C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')S(O)$_2$N(R')—, —OC(O)—, or —C(O)N(R')—O— or wherein T$_1$ or a portion thereof optionally forms part of an optionally substituted 3-7 membered cycloaliphatic or heterocyclyl ring;

each occurrence of R$^{3a}$ is independently hydrogen or an optionally substituted group selected from C$_1$-C$_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of R$^{3a}$ are taken together with a nitrogen atom to which they are bound to form an optionally substituted 3-7-membered heterocyclyl ring;

each occurrence of R$^{3b}$ is independently halogen, —CN, —NO$_2$, —R$^{3c}$, —N(R$^{3a}$)$_2$, —OR$^{3a}$, —SR$^{3c}$, —S(O)$_2$R$^{3c}$, —C(O)R$^{3a}$, —C(O)OR$^{3a}$, —C(O)N(R$^{3a}$)$_2$, —S(O)$_2$N(R$^{3a}$)$_2$, —OC(O)N(R$^{3a}$)$_2$, —N(R')C(O)R$^{3a}$, —N(R')SO$_2$R$^{3c}$, —N(R')C(O)OR$^{3a}$, —N(R')C(O)N(R$^{3a}$)$_2$, or —N(R')SO$_2$N(R$^{3a}$)$_2$, or two occurrences of R$^{1a}$ or R$^{3c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur;

each occurrence of R$^{3c}$ is independently an optionally substituted group selected from C$_1$-$_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{3d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and each occurrence of R$^{3e}$ is independently an optionally substituted group selected from 3-10-membered cycloaliphatic, or 3-10-membered heterocyclyl having 1-5 heteroatoms independently selected from nitrogen, oxygen, or sulfur;

each —R' is independently hydrogen or optionally substituted C$_{1-6}$aliphatic;

x is 0-4;

each occurrence of R$^4$ is independently —R$^{4a}$, -T$_2$-R$^{4d}$, —V$_2$-T$_2$-R$^{4d}$, wherein:

each occurrence of R$^{4a}$ is independently halogen, —CN, —NO$_2$, —R$^{4c}$, —N(R$^{4b}$)$_2$, —OR$^{4b}$, —SR$^{4c}$, —S(O)$_2$R$^{4c}$, —C(O)R$^{4b}$, —C(O)OR$^{4b}$, —C(O)N(R$^{4b}$)$_2$, —S(O)$_2$N(R$^{4b}$)$_2$, —OC(O)N(R$^{4b}$)$_2$, —N(R')C(O)R$^{4b}$, —N(R')SO$_2$R$^{4c}$, —N(R')C(O)OR$^{4b}$, —N(R')C(O)N(R$^{4b}$)$_2$, or —N(R')SO$_2$N(R$^{4b}$)$_2$, or two occurrences of R$^{4b}$ or R$^{4c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur, or two occurrences of R$^{4b}$, taken together with a nitrogen atom to which they are bound, form an optionally substituted 3-7-membered heterocyclyl ring having 0-3 additional heteroatoms selected from nitrogen, oxygen, or sulfur;

each occurrence of R$^{4b}$ is independently hydrogen or an optionally substituted group selected from C$_1$-C$_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{4b}$ is independently an optionally substituted group selected from C$_1$-C$_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{4d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of V$_2$ is independently —C(R')═C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O—;

each occurrence of $T_2$ is independently a $C_1$-$C_6$alkylene chain optionally substituted with $R^{4a}$, wherein the alkylene chain optionally is interrupted by —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')SO$_2$N(R')—, —OC(O)—, or —C(O)N(R')—O— or wherein $T_2$ or a portion thereof optionally forms part of an optionally substituted 3-7 membered cycloaliphatic or heterocyclyl ring;

$R^6$ and $R^7$ are each independently hydrogen or $C_1$-$C_4$aliphatic; and $R^8$ is $C_1$-$C_4$alkyl;

provided that the intermediate of formula II-A is other than:

a) 2-cyano-3-(2-ethoxy-1-ethyl-1H-indol-3-yl)-2-Propenamide, or b) 2-cyano-3-(2-methoxy-1H-indol-3-yl)-2-Propenamide.

In some embodiments, for the intermediate of formula II-A:

$R^3$ is -$T_1$-$R^{3d}$, $T_1$ is a $C_1$-$C_4$alkylene chain wherein the alkylene chain is optionally substituted by 1 or 2 independent occurrences of —$R^{3b}$, and the alkylene chain is optionally interrupted by —C(R')=C(R')—, —N(R')—, —O—, —S(O)$_2$—, —C(O)—, —C(O)O—, —C(O)N(R')—, —S(O)$_2$N(R')—, —OC(O)N(R')—, —N(R$^9$)C(O)—, —N(R')SO$_2$—, —N(R')C(O)O—, —NR'C(O)N(R')—, —N(R')S(O)$_2$N(R')—, —OC(O)—, or —C(O)N(R')—O—;

$R^{3d}$ is hydrogen;

each occurrence of —$R^{3b}$ is independently $C_1$-$C_3$aliphatic, —N($R^{3a}$)$_2$, —O$R^{3a}$, —C(O)O$R^{3a}$, —C(O)N($R^{3a}$)$_2$, —S(O)$_2$N($R^{3a}$)$_2$, —OC(O)N($R^{3a}$)$_2$, —N(R')C(O)$R^{3a}$, —N(R')SO$_2$$R^{3c}$, —N(R')C(O)O$R^{3a}$, —N(R')C(O)N($R^{3a}$)$_2$, or —N(R')SO$_2$N($R^{3a}$)$_2$;

x is 0, 1, or 2; and each occurrence of $R^4$ is independently halogen, —CN, —NO$_2$, —N($R^{4b}$)$_2$, —O$R^{4b}$, —S$R^{4c}$, —S(O)$_2$$R^{4c}$, —X(O)$R^{4b}$, —C(O)O$R^{4b}$, —C(O)N($R^{4b}$)$_2$, —S(O)$_2$N($R^{4b}$)$_2$, —N(R')C(O)$R^{4b}$, or —N(R')SO$_2$$R^{4c}$.

In yet other embodiments, for the intermediate of formula II-A, $T_1$ is $C_1$-$C_4$alkyl substituted with 1 or 2 independent occurrences of $R^{3b}$, wherein each occurrence of $R^{3b}$ is independently —N($R^{3a}$)$_2$, —O$R^{3a}$, or —$C_1$-$C_3$alkyl.

5. Uses, Formulation and Administration

As discussed above, the present invention provides compounds that are useful as inhibitors of IKK, and thus the present compounds are useful for treating or lessening the severity of cancer, an inflammatory disease, or an immune-related disease including, but not limited to, lymphoma, such as diffuse large B-cell, primary mediastinal B-cell, and mantle cell; multiple myeloma; osteolytic bone metastasis; head and neck squamous cell cancer; prostate cancer; pancreatic cancer, non-small cell lung cancer, joint inflammation (e.g., rheumatoid arthritis (RA), rheumatoid spondylitis, gouty arthritis, traumatic arthritis, rubella arthritis, psoriatic arthritis, osteoarthritis, and other arthritic conditions), acute synovitis, tuberculosis, atherosclerosis, muscle degeneration, cachexia, Reiter's syndrome, endotoxaemia, sepsis, septic shock, endotoxic shock, gram negative sepsis, gout, toxic shock syndrome, pulmonary inflammatory diseases (e.g., asthma, acute respiratory distress syndrome, chronic obstructive pulmonary disease, silicosis, pulmonary sarcoidosis, and the like), bone resorption diseases, reperfusion injuries, carcinoses, leukemia, sarcomas, lymph node tumors, skin carcinoses, lymphoma, apoptosis, graft versus host reaction, graft versus host disease (GVHD), allograft rejection, leprosy, viral infections (e.g., HIV, cytomegalovirus (CMV), influenza, adenovirus, the Herpes group of viruses, and the like), parasitic infections (e.g., malaria, such as cerebral malaria), yeast and fungal infections (e.g., fungal meningitis), fever and myalgias due to infection, acquired immune deficiency syndrome (AIDS), AIDS related complex (ARC), cachexia secondary to infection or malignancy, cachexia secondary to AIDS or cancer, keloid and scar tissue formation, pyresis, diabetes, inflammatory bowel diseases (IBD) (e.g., Crohn's disease and ulcerative colitis), multiple sclerosis (MS), ischemic brain injury, e.g. cerebral infarction (stroke), head trauma, psoriasis, Alzheimer's disease, carcinomatous disorders (potentiation of cytotoxic therapies), cardiac infarct, chronic obstructive pulmonary disease (COPD), and acute respiratory distress syndrome (ARDS).

It will also be appreciated that the present compounds are useful for treating diseases, disorders or symptoms related to the activity of NF-κB, TNF-α, and other enzymes in pathways where IKK is known to modulate activity.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of IKK.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating cancer is provided comprising administering an effective amount of a compound, or a pharmaceutical composition to a subject in need thereof. In yet another aspect, a method for treating an inflammatory disease or immune-related disease is provided comprising administering an effective amount of a compound, or a pharmaceutical composition to a subject in need thereof. In certain embodiments of the present invention an "effective amount" of the compound or pharmaceutical composition is that amount effective for treating cancer, or is that amount effective for treating an inflammatory disease or immune-related disease. In other embodiments, an "effective amount" of a compound is an amount which inhibits binding of IKK and thereby blocks the phosphorylation of IKB and its further downstream effects.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described above, compounds of the invention are inhibitors of IKK. Accordingly, compounds of the invention are suitable for the prophylaxis treatment and therapy of diseases, disorders and symptoms that involve increased activity of IkB kinase. These include, for example, joint inflammation (e.g., rheumatoid arthritis (RA), rheumatoid spondylitis, gouty arthritis, traumatic arthritis, rubella arthritis, psoriatic arthritis, osteoarthritis, and other arthritic conditions), acute synovitis, tuberculosis, atherosclerosis, muscle degeneration, cachexia, Reiter's syndrome, endotoxaemia, sepsis, septic shock, endotoxic shock, gram negative sepsis, gout, toxic shock syndrome, pulmonary inflammatory diseases (e.g., asthma, acute respiratory distress syndrome, chronic obstructive pulmonary disease, silicosis, pulmonary sarcoidosis, and the like), bone resorption diseases, reperfusion injuries, carcinoses, leukemia, sarcomas, lymph node tumors, skin carcinoses, lymphoma, apoptosis, graft versus host reaction, graft versus host disease (GVHD), allograft rejection and leprosy.

Furthermore, the inventive compounds may be used in the treatment of immune-related diseases, symptoms and disorders, for example, infections, such as viral infections (e.g., HIV, cytomegalovirus (CMV), influenza, adenovirus, the Herpes group of viruses, and the like), parasitic infections (e.g., malaria, such as cerebral malaria), and yeast and fungal infections (e.g., fungal meningitis). In addition, the inventive compounds can be useful for treating fever and myalgias due to infection, acquired immune deficiency syndrome (AIDS), AIDS related complex (ARC), cachexia secondary to infection or malignancy, cachexia secondary to AIDS or cancer, keloid and scar tissue formation, pyresis, diabetes, and inflammatory bowel diseases (IBD) (e.g., Crohn's disease and ulcerative colitis). The compounds of the invention are also useful in the treatment of diseases or injuries to the brain in which over-expression of TNF-α has been implicated, such as multiple sclerosis (MS), ischemic brain injury, e.g. cerebral infarction (stroke) and head trauma. The compounds of the invention are also useful in the treatment of psoriasis, Alzheimer's disease, carcinomatous disorders (potentiation of cytotoxic therapies), cardiac infarct, chronic obstructive pulmonary disease (COPD) and acute respiratory distress syndrome (ARDS).

In some embodiments, the compounds of formula (I) are useful for treating inflammatory and immune-related diseases, disorders and symptoms, more especially, inflammatory ones such as RA, asthma, IBD, psoriasis, COPD and MS.

In other embodiments, compounds of the invention are useful for treating cancer, especially for treating cancers where IKK activity is abnormally high. The cancer types that may be treated include lymphoma, such as diffuse large B-cell (Davis, et al., *J. Exp. Med.* 2001, 194, 1861-1874; Lam et al., *Clin. Cancer Res.* 2005, 11, 28-40; Feuerhake et al., *Blood,* 2005, 106, 1392-1399), primary mediastinal B-cell, and mantle cell; multiple myeloma (Berenson et al., *Clin. Adv. Hematol. Oncol.* 2004, 2, 162-166; Gunn et al., *Stem Cells,* 2005); osteolytic bone metastasis (Ruocco et al., *J. Exp. Med.* 2005, 201, 1677-1687; Morony, et al., *Endocrinology,* 2005, 146, 3235-3243; Gordon, et al., *Cancer Res.,* 2005, 65, 3209-3217; RoleSohara, et al., *Cancer Lett.,* 2005, 228, 203-209); head and neck squamous cell cancer (van Hogerlinden et al., *J. Invest. Dermatol.,* 2004, 123 101-108; Tamatani et al, *Int. J. Cancer.,* 2004, 108, 912-921; Loercher et al., *Cancer Res.* 2004, 64, 6511-6523; Van Waes et al., *Int. J. Radiat. Oncol. Biol. Phys.* 2005 63, 1400-1412); prostate cancer; pancreatic cancer and non-small cell lung cancer. In one embodiment, the compounds are useful for ABC lymphoma.

The compounds of this invention are also useful for treating a bone associated disease, symptom or disorder in which there is a deficit or deficiency of bone—either as a result of decreased new bone formation or an increase in bone resorption or a combination of both. Specific examples include osteoporosis, periodontal disease, osteomyelitis, rheumatoid arthritis, aseptic joint loosening and osteolytic lesions (typically cancer related). It is known that rheumatoid arthritis, which is characterized by inflammation of the joints, is also associated with destruction of cartilage and bone. Furthermore, it has been reported that an IKK inhibitor provided inhibition of cartilage and bone loss in a murine model of collagen-induced arthritis. See McIntyre et al., *Arthritis & Rheumatism* (2003), 48(9), 2652-2659.

Osteoporosis is a broad term applied to a number of distinct diseases in which there is decreased bone mass. These include primary osteoporosis (e.g., post-menopausal, senile osteoporosis and juvenile osteoporosis) and secondary osteoporosis. Examples of secondary osteoporosis would be those associated with chronic diseases (e.g., chronic renal disease, hepatic insufficiency, gastrointestinal malabsorption, chronic immobilization and chronic inflammatory diseases, including rheumatoid arthritis, osteoarthritis, periodontal disease and aseptic prosthetic joint loosening), endocrine dysfunction related diseases (e.g., diabetes, hyperthyroidism, hyperparathyroidism, hypogonadism and hypopituitarism), drug and substance related symptoms (e.g., corticosteroid, heparin, anticonvulsants, alcohol and immunosupressants), and hematological disorders (e.g., metastatic disease, myeloma, leukemia, gaucher's disease and anemia). Inhibition of either IkB directly or the NF-kB pathway indirectly has been reported to be useful for the treatment of osteoporosis and osteoarthritis. See, for example, PCT applications WO 2003104219, WO 2003103658, WO 2003029242, WO 2003065972, and WO 9965495. Accordingly, this invention also provides a method of treating or preventing bone loss in a patient in need thereof, comprising administering to the patient a compound of this invention. Also provided is a method of generating bone formation in a patient comprising administering a compound of this invention.

Another embodiment of the invention provides a method of inhibiting activation of NF-κB dependent gene expression associated with the inhibition of IKK catalytic activity and/or IκB phosphorylation, comprising administering to a patient in need thereof an amount of a compound of the invention or a pharmaceutically acceptable salt or solvate thereof, or a pharmaceutical composition thereof, which is effective to inhibit IKK catalytic activity and/or IκB phosphorylation, thereby inhibiting activation of NF-κB dependent gene expression.

In one embodiment of the invention, there is provided a method of treating an inflammatory or immune-related disease in a patient in need of such treatment, comprising administering to the patient an amount of at least one compound of the invention, or a pharmaceutically acceptable salt or solvate thereof, or a pharmaceutical composition thereof, which is effective to treat the inflammatory or immune-disease. Preferably, the inflammatory disease, disorder or symptom is rheumatoid arthritis, asthma, psoriasis, psoriatic arthritis, chronic obstructive pulmonary disease (COPD), inflammatory bowel disease or multiple sclerosis.

In another embodiment, there is provided a method of treating cancer comprising administering to the patient an amount of at least one compound of the invention, or a pharmaceutically acceptable salt or solvate thereof, or a pharmaceutical composition thereof, which is effective to treat the cancer. In certain embodiments, the cancer is a lymphoma (more preferably non-Hodgkin's lymphoma), multiple myeloma, or head and neck squamous cell carcinoma.

In yet another embodiment of the invention, there is provided a method of treating cystic fibrosis in a patient in need of such treatment, comprising administering to the patient an amount of at least one compound of the invention, or a pharmaceutically acceptable salt or solvate thereof, or a pharmaceutical composition thereof.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents, such as other inhibitors of IKK, other agents useful in treating NF-κB and TNF-α associated conditions, and agents useful for treating other disorders, symptoms and diseases. In particular, agents that induce apoptosis such as agents that disrupt cell cycle or mitochondrial function are useful in combination with the IKK inhibitors of this invention. Exemplary agents for combination with the IKK inhibitors include antiproliferative agents (e.g., methotrexate) and the agents disclosed in U.S. Pat. Application Publication No. US2003/0022898, p 14, para. [0173-0174], which is incorporated herein in its entirety. In some embodiments, a compound of the invention is administered in conjunction with a therapeutic agent selected from the group consisting of cytotoxic agents, radiotherapy, and immunotherapy. Non-limiting examples of cytotoxic agents suitable for use in combination with the IKK inhibitors of the invention include capecitibine; gemcitabine; irinotecan; fludarabine; 5-fluorouracil or 5-fluorouracil/leucovorin; taxanes, including, e.g., paclitaxel and docetaxel; platinum agents, including, e.g., cisplatin, carboplatin, and oxaliplatin; anthracyclins, including, e.g., doxorubicin and pegylated liposomal doxorubicin; mitoxantrone; dexamethasone; vincristine; etoposide; prednisone; thalidomide; herceptin; temozolomide; and alkylating agents such as melphalan, chlorambucil, and cyclophosphamide. It is understood that other combinations may be undertaken while remaining within the scope of the invention.

Another aspect of the invention relates to inhibiting IKK, activity in a biological sample or a patient, which method comprises administering to the patient, or contacting said biological sample with a compound of formula I or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where IkB kinase plays a role.

EXPERIMENTAL PROCEDURES

Unless otherwise stated, analytical LCMS conditions are as follows:

Standard Conditions Column type: Waters Symmetry C18 100×4.6 mm IC, 3.5 μm

Run time: 10.00 minute run

QC Conditions Column type: Waters symmetry C18 50×4.6 mm ID, 3.5 μm

Run time: 5.00 minute run

NH$_4$OAc (A) Standard Conditions:
Solvent A:

10 mM NH$_4$Oac
98% H$_2$O
2% Isopropyl alcohol
Solvent B:

10 mM NH$_4$Oac
25% Methanol
75% MeCN
HCOOH (FA) Standard and QC Conditions:
Solvent C:

0.1% HCOOH
99% H$_2$O
1% MeCN
Solvent D:

0.1% HCOOH
5% H$_2$O
95% MeCN
NH$_4$Oac (AA) QC conditions:
Solvent A:

10 mM NH$_4$Oac
99% H$_2$O
1% MeCN
Solvent B:

10 mM NH$_4$OAc
5% H2O
95% MeCN

| Time [min] | Solvent A % | Solvent B % | Flow rate [ml/min] |
|---|---|---|---|
| Standard gradient (ammonium acetate and formic acid conditions): | | | |
| 0.00 | 95.0 | 5.0 | 1.0 |
| 7.50 | 0.0 | 100.0 | 1.0 |
| 8.00 | 0.0 | 100.0 | 1.0 |
| 9.75 | 0.0 | 100.0 | 1.0 |
| 9.80 | 95.0 | 5.0 | 1.0 |
| 10.00 | 95.0 | 5.0 | 1.0 |
| QC gradient (ammonium acetate and formic acid conditions): | | | |
| 0.00 | 95.0 | 5.0 | 1.0 |
| 3.50 | 0.0 | 100.0 | 1.0 |
| 4.90 | 0.0 | 100.0 | 1.0 |
| 5.0 | 95.0 | 5.0 | 1.0 |

Example 1

Synthesis of
2-amino-9H-pyrido[2,3-b]indole-3-carboxamide (5)

The synthesis of 2-amino-9H-pyrido[2,3-b]indole-3-carboxamide (5) is exemplified generally in Scheme I and is described specifically below Scheme I

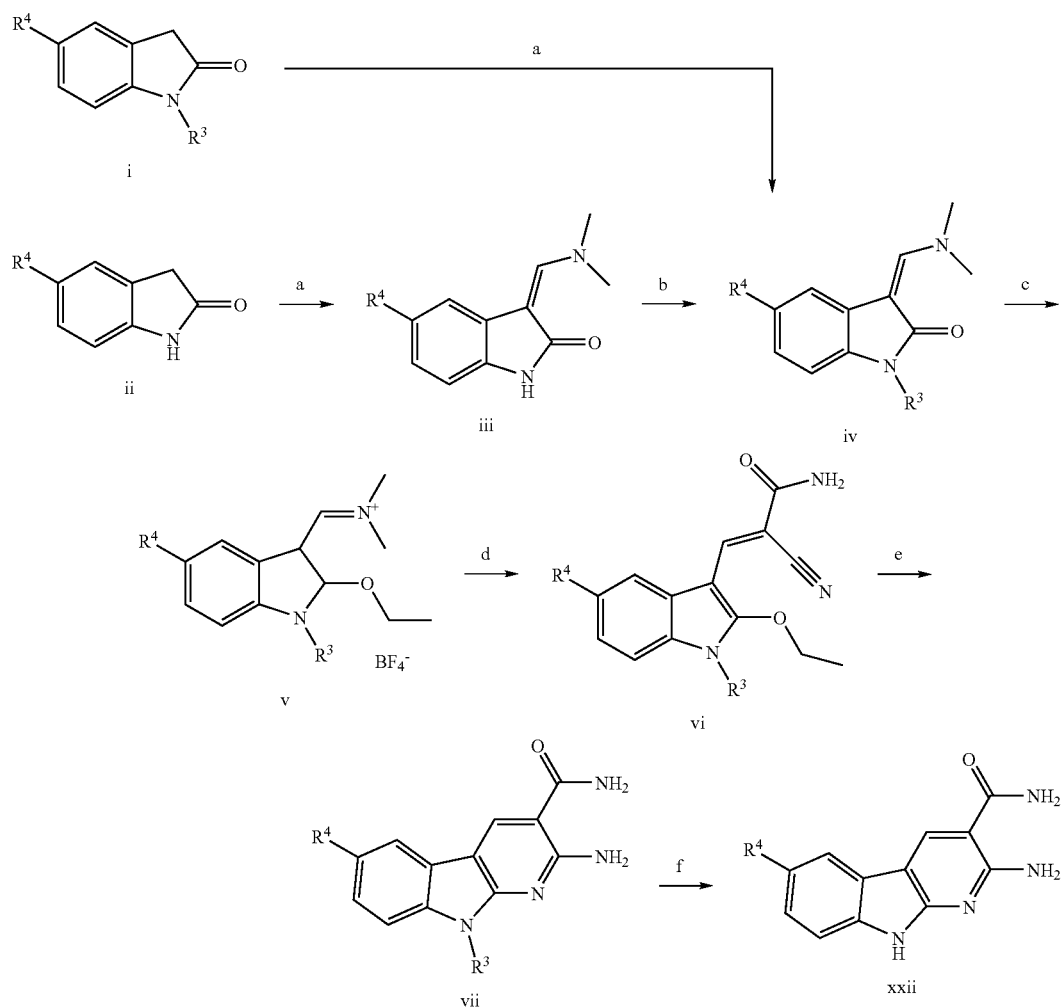

Step 1: (3Z)-3-[(dimethylamino)methylene]-1,3-dihydro-2H-indol-2-one (iii-a)

Step 2: (3Z)-1-benzyl-3-[(dimethylamino)methylene]-1,3-dihydro-2H-indol-2-one (iv-a)

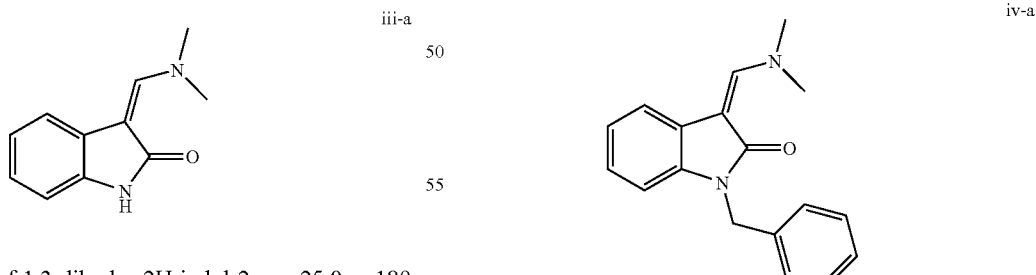

To a solution of 1,3-dihydro-2H-indol-2-one 25.0 g, 189 mmol) in CHCl₃ (150 mL) was added N,N-dimethylformamide dimethyl acetal (29.2 mL, 209 mmol) and the reaction was heated at 70° C. under an atmosphere of argon. After 4.5 h, the reaction was cooled to RT and was concentrated. The resulting solid was triturated with ether and filtered to give (3Z)-3-[(dimethylamino)methylene]-1,3-dihydro-2H-indol-2-one as a yellow solid (iii-a, 33.0 g, 93%). NH₄OAc QC conditions. DAD Retention Time=1.19 min. M+H=189.

To a solution of (3Z)-3-[(dimethylamino)methylene]-1,3-dihydro-2H-indol-2-one (iii-a, 626 mg, 3.33 mmol) in DMF (10 mL) was added NaH (151 mg, 6.29 mmol) and the reaction was stirred at RT. After 10 min, benzyl bromide (500 μL, 4.20 mmol) was added and the mixture was stirred under an atmosphere of Ar for 22 h. The reaction was quenched with a few drops of water and poured into a separatory funnel containing EtOAc (150 mL) and was washed with water (2×100 mL), followed by brine (100 mL). The organic layer was dried over sodium sulfate, filtered and concentrated. The crude product was purified by silica gel chromatography (EtOAc/Hexane) to yield (3Z)-1-benzyl-3-[(dimethylamino)methylene]-1,3-dihydro-2H-indol-2-one as a yellow solid (iv-a, 660 mg, 71%). N'H$_4$OAc QC conditions. DAD Retention Time=1.71 min. M+H=279.

Step 3: N-[(1-benzyl-2-ethoxy-1H-indol-3-yl)methylene]-N-methylmethanaminium tetrafluoroborate (v-a)

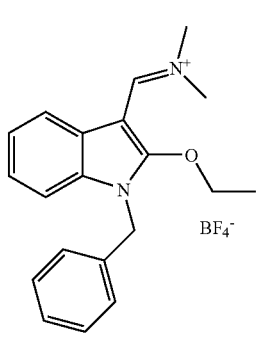

v-a

To a solution of (3Z)-1-benzyl-3-[(dimethylamino)methylene]-1,3-dihydro-2H-indol-2-one (iv-a, 7.69 g, 27.6 mmol) in dichloroethane (50 mL) was added triethyloxonium tetrafluoroborate (10.7 g, 56.4 mmol) and the reaction mixture was heated at 110° C. under an atmosphere of Ar. After 3 h, the reaction was cooled to RT and was concentrated. The crude material was stirred in ether (75 mL) and a solid was precipitated. The solid was filtered to yield N-[(1-benzyl-2-ethoxy-1H-indol-3-yOmethylene]-N-methylmethanaminium tetrafluoroborate (v-a, theoretical yield 27.6 mmol) as a brown solid which was used without further purification in the next step. NH$_4$OAc QC conditions. DAD Retention Time=1.28 min. M+H=308.

Step 4: (2E)-3-(1-benzyl-2-ethoxy-1H-indol-3-yl)-2-cyanoacrylamide (vi-a)

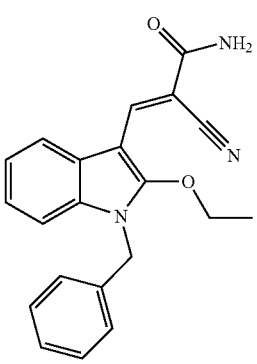

vi-a

To a mixture of cyanoacetamide (4.60 g, 54.7 mmol) and NaOMe (0.5 M solution in MeOH, 80 mL, 4 mmol) was added a solution of (N-[(1-benzyl-2-ethoxy-1H-indol-3-yl)methylene]-N-methylmethanaminium tetrafluoroborate (v-a, 27.6 mmol) in MeOH (120 mL). The reaction was stirred at RT under an atmosphere of Ar. After 15 h, the reaction was cooled to 0° C. and was quenched by the addition of water. The insoluble product was filtered, triturated in MeOH and refiltered to yield a yellow solid (2E)-3-(1-benzyl-2-ethoxy-1H-indol-3-yl)-2-cyanoacrylamide (vi-a, 5.68 g, 60%). NH$_4$OAc QC conditions. DAD Retention Time=1.78 min. M+H=346.

Step 5: 2-amino-9-benzyl-9H-pyrido[2,3-b]indole-3-carboxamide

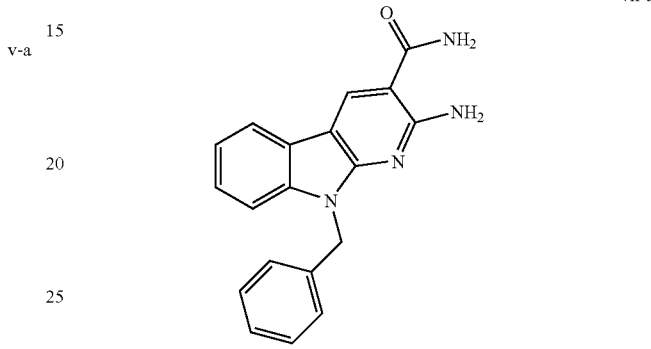

vii-a

To a solution of (2E)-3-(1-benzyl-2-ethoxy-1H-indol-3-yl)-2-cyanoacrylamide (vi-a, 2.00 g, 5.79 mmol) in MeOH (150 mL) was added NH$_4$OH (30% weight solution of NH$_3$ in water, 100 mL). The reaction was stirred at RT overnight. The reaction was concentrated under reduced pressure and the crude solid was triturated with H$_2$O. The solid was filtered and triturated again with ether. A yellow solid was collected by suction filtration to yield 2-amino-9-benzyl-9H-pyrido[2,3-b]indole-3-carboxamide 1.23 g, 63%). NH$_4$OAc standard conditions. DAD Retention time=7.25 min. M+H=317. $^1$H NMR (300 MHz, DMSO-d$_6$): δ 8.77 (s, 1H), 7.83 (d, J=7.8 Hz, 1H), 7.62 (br s, 2H), 7.40 (d, J=7.7 Hz, 1H), 7.31-7.16 (m, 9H), 5.52 (s, 2H).

2-amino-9H-pyrido[2,3-b]indole-3-carboxamide (5)

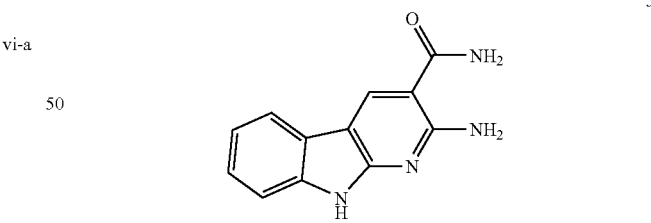

5

To a solution of 2-amino-9-benzyl-9H-pyrido[2,3-b]indole-3-carboxamide (vii-a, 1.01 g, 319 mmol) in benzene (30 mL) was added AlCl$_3$ (1.10 g, 8.25 mmol), and the reaction was heated to 95° C. under atmosphere of Ar. After 6 h, the reaction was cooled to 0° C., quenched with water (75 mL) and poured into a separatory funnel containing EtOAc (200 mL). The mixture was washed with 1N NaOH (2×200 mL) and the organic layer was dried over sodium sulfate, filtered and concentrated to yield 2-amino-9H-pyrido[2,3-b]indole-3-carboxamide as a light brown solid (5, 319 mg, 44%). NH$_4$OAc Standard conditions. DAD Retention Time=5.10 min. M+H=227. $^1$H NMR (300 MHz, DMSO-d$_6$): δ 11.33 (br s, 1H), 8.68 (s, 1H), 7.85 (br s, 1H), 7.76 (d, J=7.9 Hz, 1H), 7.44 (br s, 1H), 7.32 (d, J=7.3 Hz, 1H), 7.24 (dd, J=7.3, 7.3 Hz, 1H), 7.12 (dd, J=7.9, 7.9 Hz, 1H).

Compounds in the following table were prepared from the appropriate starting materials in a method analogous to that described in example 1.

| No. | LCMS Standard Method: (FA/AA) | ES+ | ES− | Retention Time (min) |
|---|---|---|---|---|
| 5 | AA | 375 | | 5.10 |
| 62 | AA (QC Conditions) | 263 | 261 | 1.63 (QC Conditions) |
| 1 | AA | 255 | 253 | 7.89 |
| 2 | AA | 241 | 239 | 6.35 |
| 3 | AA | 287 | 289 | 7.52 |
| 46 | AA | 289 | 287 | 7.24 |
| 55 | AA | 289 | 287 | 7.17 |

2-amino-6-bromo-9H-pyrido[2,3-b]indole-3-carboxamide (34)

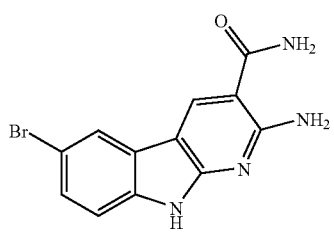

To a solution of 2-amino-9H-pyrido[2,3-b]indole-3-carboxamide (5, 35 mg, 0.15 mmol) in acetonitrile (1 mL) and N,N-dimethylformamide (1 mL), was added N-bromosuccinimide (37 mg, 0.209 mmol) in one portion at −10° C. The mixture was warmed to room temperature and stirred for one hour. Water was added and the mixture was extracted with methylene chloride (3×20 mL). Extracts were combined, dried over sodium sulfate, filtered and concetnrated to afford the crude product which was subsequently purified by HPLC (Phenomenex Luna 15 μm C18, aqueous HCOOH/CH$_3$CN) to yield 2-amino-6-bromo-9H-pyrido[2,3-b]indole-3-carboxamide (34, 20 mg, 40%) as yellow solid. NH$_4$OAc standard conditions. DAD Retention Time=6.12 min. M+H=307. $^1$H NMR (300 MHz, MeOD): δ 8.65 (d, J=6.9 Hz, 1H), 8.03 (d, J=4.9 Hz, 1H), 7.43-7.37 (m, 1H), 7.33-7.27 (m, 1H).

2-amino-9-ethyl-6-methyl-9H-pyrido[2,3-b]indole-3-carboxamide (4)

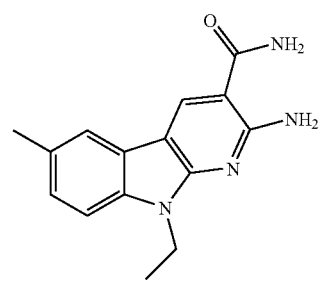

2-Amino-9-ethyl-6-methyl-9H-pyrido[2,3-b]indole-3-carboxamide was prepared from i-a (see Example 2 below) following the procedures detailed in example 1 as depicted in Scheme 1. NH$_4$OAc standard conditions. DAD R$_f$=7.33 min. M+H=268.

Example 2

Synthesis of 1-ethyl-5-methyl-1,3-dihydro-2H-indol-2-one (i-a)

Scheme II

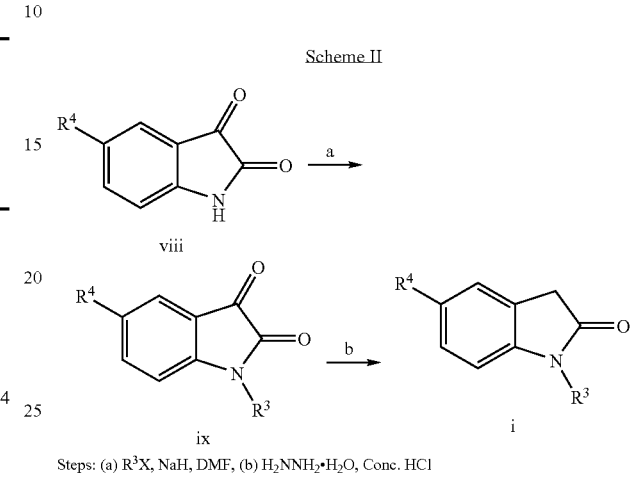

Steps: (a) R$^3$X, NaH, DMF, (b) H$_2$NNH$_2$·H$_2$O, Conc. HCl

Step 1: 1-ethyl-5-methyl-1H-indole-2,3-dione (ix-a)

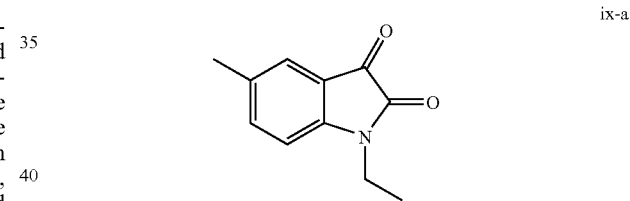

To a solution of 1-ethyl-5-methyl-1H-indole-2,3-dione (viii-a, 2.04 g, 12.4 mmol) in DMF (50 mL) was added NaH (601 mg, 15.0 mmol). After 15 min, C$_2$H$_5$I (1.20 mL, 15.0 mmol) was added. The reaction was stirred at RT for 3 h, quenched with water and poured into a reparatory funnel containing EtOAc (200 mL). The mixture was shaken and the layers were separated. The organic layer was washed with water (4×150 mL), dried, filtered and concentrated. The resulting solid was triturated in ether and was filtered to yield 1-ethyl-5-methyl-1H-indole-2,3-dione as a brick red solid (ix-a, 1.53 g, 66%). NH$_4$OAc QC conditions. DAD Retention Time=1.50 min. M+H=191.

Step 2: 1-ethyl-5-methyl-1,3-dihydro-2H-indol-2-one (i-a)

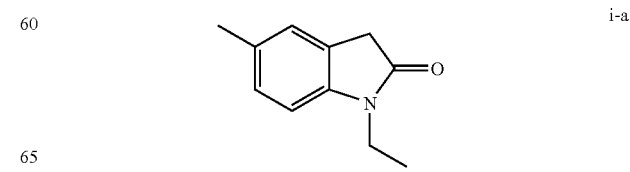

A mixture of 1-ethyl-5-methyl-1H-indole-2,3-dione (ix-a, 1.53 g, 8.09 mmol) and hydrazine monohydrate (30 mL, 618 mmol) was heated to 110° C. After 5 h, the reaction was cooled to RT and conc. HCl was added to adjust the reaction mixture to approximately pH 3. The mixture was stirred overnight, and poured into a separatory funnel containing EtOAc (150 mL). The mixture was shaken and the layers were separated. The aqueous layer was extracted with EtOAc (2×150 mL) and the combined organic layers were dried, filtered and concentrated to give 1-ethyl-5-methyl-1,3-dihydro-2H-indol-2-one (i-a, 1.03 g, 72.5%). NH$_4$OAc QC conditions. DAD Retention time=1.48 min. M+H=176.

Example 3

Synthesis of Exemplary N-Substituted Alpha Carbolines

The examples below depict the synthesis of a variety of N-substituted alpha carbolines from the general intermediate (xi).

Scheme III

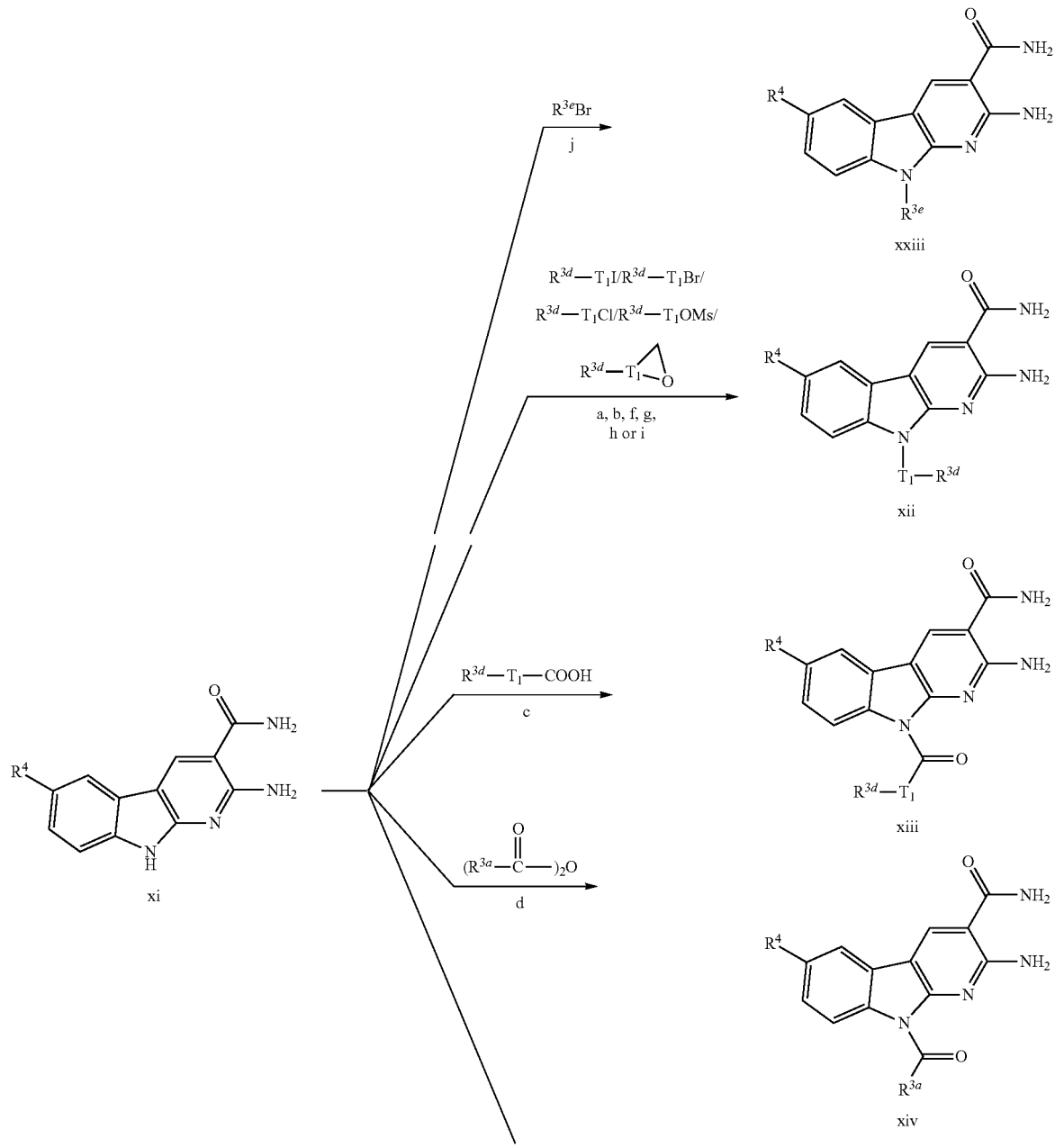

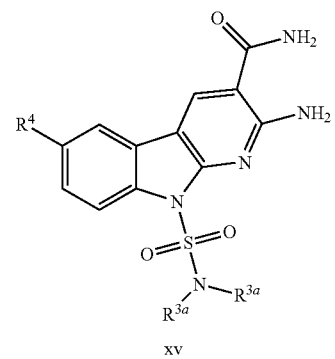

Steps: (a) NaH, DMF (b) t-BuOK, KI, DMF (c) EDC, DMAP, pyridine (d) DMAP, pyridine (e) NaH, THF (f) Cs₂CO₃, DMF, thermal (g) Cs₂CO₃, DMF, microwave (h) KOH, DMSO (i) NaOH, DMF, phase transfer catalyst (j) CuI, dioxane, diamine ligand 2-amino-9-isopropyl-9H-pyrido[2,3-b]indole-3-carboxamide (13)

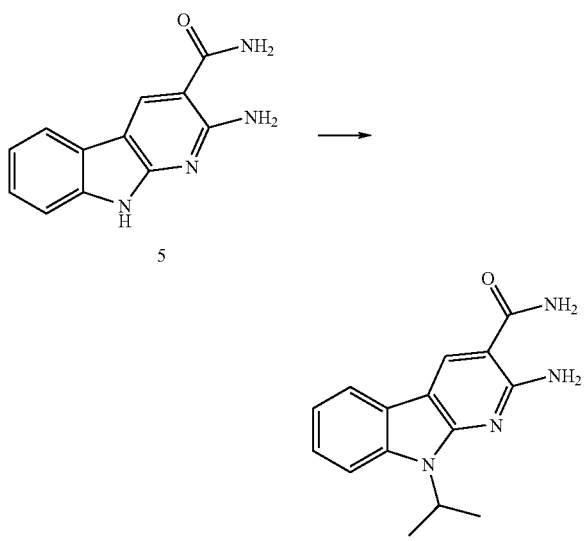

To a solution of 2-amino-9H-pyrido[2,3-b]indole-3-carboxamide (5, 122 mg, 0.540 mmol) in DMF (5 mL) was added NaH (110 mg, 2.75 mmol) and the reaction was stirred for 10 min. 2-Bromopropane (111 µL, 0.688 mmol) was added and the mixture was stirred at RT for another 2.5 h. The reaction was quenched with water (50 mL), poured into a separatory funnel containing EtOAc (150 mL), the mixture was shaken and the layers were separated. The organic layer was washed with brine (100 mL), dried, filtered and concentrated. The crude product was purified by silica gel chromatography (MeOH/CH₂Cl₂ gradient) to yield 2-amino-9-isopropyl-9H-pyrido[2,3-b]indole-3-carboxamide as a white powder (13, 30 mg, 21%). NH₄OAc standard conditions. DAD Retention time=6.95 min. M+H=269. ¹H NMR (300 MHz, DMSO-d₆): δ8.72 (s, 1H), 7.82 (d, J=7.8 Hz, 1H), 7.61 (d, J=8.1 Hz, 1H), 7.54 (br s, 2H), 7.29 (ddd, J=8.4, 8.4, 1.2 Hz, 1H), 7.17 (ddd, J=7.5, 7.5, 0.9 Hz, 1H), 5.23 (septet, J=6.9 Hz, 1H), 1.60 (d, J=6.9 Hz, 6H).

Compounds in the following table were prepared from the appropriate starting materials in a method analogous to that described in the preparation of 13.

| No. | LCMS Standard Method: (FA/AA) | ES+ | ES− | Retention Time (min) |
|---|---|---|---|---|
| 10 | AA | 284 | 282 | 4.51 |
| 13 | AA | 269 | | 6.95 |
| 14 | AA | 269 | 267 | 6.88 |
| 18 | FA | 298 | 296 | 3.54 |
| 33 | AA | 333 | | 7.36 |
| 36 | AA | 266 | 264 | 5.68 |
| 23 | AA | 374 | | 7.81 |
| 24 | FA | 384 | | 3.79 |
| 29 | AA | 384 | 382 | 6.97 |

2-amino-9-isobutyl-9H-pyrido[2,3-b]indole-3-carboxamide (44)

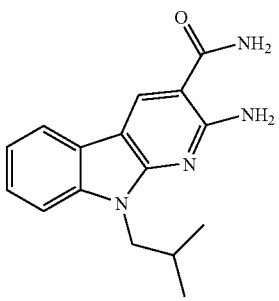

Step 1: 2-amino-9-(2-methylprop-2-en-1-yl)-9H-pyrido[2,3-b]indole-3-carboxamide (xii-a)

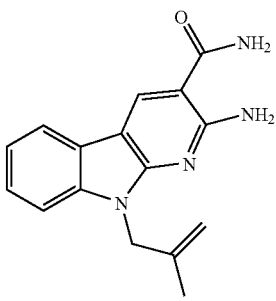

xii-a

2-Amino-9H-pyrido[2,3-b]indole-3-carboxamide (5, 196 mg, 0.866 mmol) was alkylated with methallyl bromide (0.131 mL, 1.30 mmol) according to the procedure detailed in the synthesis of 13 to afford 2-amino-9-(2-methylprop-2-en-1-yl)-9H-pyrido[2,3-b]indole-3-carboxamide (xii-a, 143 mg, 59%).

Step 2: 2-amino-9-isobutyl-9H-pyrido[2,3-b]indole-3-carboxamide (44)

2-Amino-9-(2-methylprop-2-en-1-yl)-9H-pyrido[2,3-b]indole-3-carboxamide (xii-a, 143 mg) was dissolved in ethanol (40 mL) and placed under an argon atmosphere. 10% Palladium on carbon (26 mg) was added and the reaction placed under an atmosphere of hydrogen by repeated evacuation followed by back-filling using a balloon filled with hydrogen gas. The reaction stirred for 16 h at room temperature then the catalyst was removed by filtration through Celite® and the filtrate concentrated in vacuo. The residue was purified by silica gel chromatography (5% methanol in methylene chloride) to afford the title compound (44, 44 mg, 65%). NH$_4$OAc standard conditions. DAD Retention time=7.45 min. M+H=283. $^1$H NMR (300 MHz, CDCl$_3$): δ8.22 (s, 1H), 7.83 (d, J=7.3 Hz, 1H), 7.30-7.36 (m, 3H), 7.21 (br s, 1H), 6.66 (br s, 1H), 5.67 (br s, 1H), 4.07 (d, J=7.3 Hz, 1H), 2.28-2.42 (m, 1H), 0.94 (d, J=6.7 Hz, 6H).

2-amino-9-(1,4,5,6-tetrahydropyrimidin-2-ylmethyl)-9H-pyrido[2,3-b]indole-3-carboxamide (32)

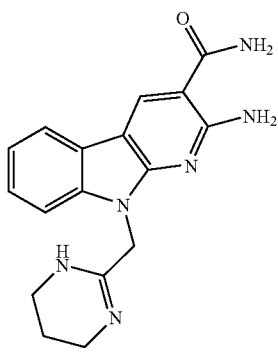

32

To a stirred solution of 2-amino-9H-pyrido[2,3-b]indole-3-carboxamide (5, 100 mg, 0.44 mmol) in dimethyl sulfoxide (1 mL) was added powdered potassium hydroxide (370 mg, 6.6 mmol), and the resulting mixture stirred at room temperature for 10 min. 2-(Chloromethyl)-1,4,5,6-tetrahydropyrimidine.HCl (Stillings, M. R., *J. Med. Chem.* 1986, 29, 2280-2284; 220 mg, 1.3 mmol) in dimethyl sulfoxide (1 mL) was added dropwise to the mixture over 0.5 h at 5-10° C. Upon completion of addition, the reaction was allowed to stir overnight at room temperature. The crude reaction mixture was concentrated under reduced pressure and purified by HPLC (Phenomenex Luna 15 μm C18, aqueous HCOOH/CH$_3$CN) to yield 2-amino-9-(1,4,5,6-tetrahydropyrimidin-2-ylmethyl)-9H-pyrido[2,3-b]indole-3-carboxamide (32, 14 mg, 10%). NH$_4$OAc standard conditions. DAD Retention time=4.42 min. M+H=323. $^1$H NMR (300 MHz, MeOD): δ 8.73 (s, 1H), 8.49 (s, 1H), 7.94 (d, J=6.9 Hz, 1H), 7.42-7.40 (m, 2H), 7.33-7.27 (m, 1H), 5.29 (s, 2H), 3.45 (t, J=5.7 Hz, 4H), 2.04 (t, J=5.7 Hz, 2H).

Compounds in the following table were prepared from the appropriate starting materials in a method analogous to that described in the preparation of 32.

| No. | LCMS Standard Method: (FA/AA) | ES+ | ES− | Retention Time (min) |
|---|---|---|---|---|
| 38 | AA | 307 | | 5.03 |
| 37 | AA | 307 | | 4.98 |
| 32 | AA | 323 | | 4.42 | tert-butyl (1-{[2-amino-3-(aminocarbonyl)-9H-pyrido[2,3-b]indol-9-yl]methyl}cyclopropyl)carbamate (63)

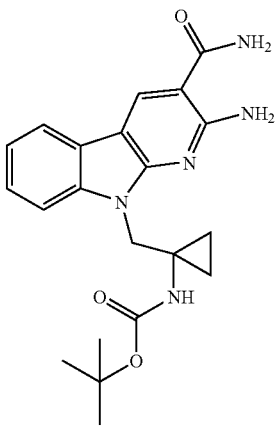

63

To a stirred solution of 2-amino-9H-pyrido[2,3-b]indole-3-carboxamide (5, 318 mg, 1.41 mmol) in N,N-dimethylformamide (17 mL) was added powdered cesium carbonate (2.29 g, 7.03 mmol), tert-butyl[1-(iodomethyl)cyclopropyl]carbamate (2.26 g, 7.61 mmol, prepared from the corresponding alcohol (*J. Med. Chem.* 1988, 31, 1694-7) following the procedure detailed in the preparation of xxvii below) was added. The mixture was heated at 100° C. under nitrogen for 2 h. The reaction was cooled to room temperature, diluted with ethyl acetate (150 mL) and washed thrice with water and twice with brine. The extracts were dried over magnesium sulfate, filtered and concentrated. The crude product was purified by silica gel chromatography (95/5 methylene chloride/methanol to 93/7 methylene chloride/methanol gradient) to afford the titled product (63, 75 mg, 13%). NH$_4$OAc Standard conditions. DAD Retention time=7.29 min. M+H=396. $^1$H NMR (300 MHz, DMSO-d$_6$): δ 8.72 (s, 1H), 7.79 (d, J=7.3 Hz, 1H), 7.54-7.41 (m, 2H), 7.26 (dd, J=7.3 Hz, 1H), 7.20-7.11 (m, 2H), 4.34 (s, 2H), 1.35 (s, 9H), 1.18-1.05 (m, 2H), 0.65-0.54 (m, 2H).

2-amino-9-pyridin-3-yl-9H-pyrido[2,3-b]indole-3-carboxamide (67)

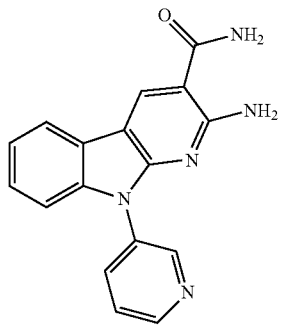

67

To a stirred mixture of 2-amino-9H-pyrido[2,3-b]indole-3-carboxamide (5, 100 mg, 0.44 mmol), Copper(I) iodide (8 mg, 0.045 mmol) and potassium phosphate (190 mg, 0.88 mmol) under dry nitrogen was added (±)-trans-1,2-diaminocyclohexane (5 μL, 0.04 m mol) and 3-bromopyridine (43 μL, 0.442 mmol), followed by 1,4-dioxane (2 mL). The mixture was heated at 110° C. for 2 days. The reaction mixture was cooled to room temperature, extracted with methylene chloride (3×30 ml) and washed with water. The extracts were combined, dried over sodium sulfate, filtered and concentrated. The crude product was purified by silica gel chromatography (12 g silica, methylene chloride to 90/10 methylene chloride/methanol gradient) to yield 2-amino-9-pyridin-3-yl-9H-pyrido[2,3-b]indole-3-carboxamide (67, 20 mg, 10%). NH$_4$OAc standard conditions. DAD Retention time=5.99 min. M+H=310. $^1$H NMR (300 MHz, MeOD): δ 8.86 (d, J=2.4 Hz, 1H), 8.74 (s, 1H), 8.66-8.63 (m, 1H), 8.14 (d, J=8.2 Hz, 1H), 7.96 (d, J=7.0 Hz, 1H), 7.70 (dd, J=4.7, 8.2 Hz, 1H), 7.36-7.28 (m, 4H).

Compounds in the following table were prepared from the appropriate starting materials in a method analogous to that described in the preparation of 67.

| No. | LCMS Standard Method: (FA/AA) | ES+ | ES− | Retention Time (min) |
|---|---|---|---|---|
| 67 | AA | 304 | | 5.99 |
| 68 | AA | 303 | 301 | 7.46 |

Example 22

2-amino-9-[2-(1H-pyrrol-1-yl)ethyl]-9H-pyrido[2,3-b]indole-3-carboxamide (20)

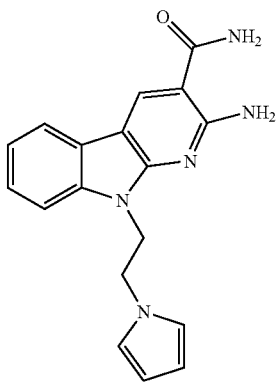

20

To a solution of 2-amino-9H-pyrido[2,3-b]indole-3-carboxamide (5, 70 mg, 0.310 mmol) in DMF (2 mL) was added potassium tert-butoxide (84 mg, 0.749 mmol). The reaction mixture was stirred at room temperature for 10 min, then 1-(2-bromoethyl)-1H-pyrrole (162 mg, 0.930 mmol) and potassium iodide (164 mg, 0.930 mmol) were added and the mixture was stirred at room temperature overnight. The reaction was quenched with water (50 mL) and extracted with ethyl acetate (150 mL). The layers were separated and the organic layer was washed with brine (100 mL), dried over magnesium sulfate, filtered and concentrated in vacuo. The crude product was purified by silica gel chromatography (0-3% methanol in methylene chloride gradient) to yield material which was subsequently triturated with ether to give pure 2-amino-9-[2-(1H-pyrrol-1-yl)ethyl]-9H-pyrido[2,3-b]indole-3-carboxamide as a white powder (20, 25 mg, 25%). NH$_4$OAc standard conditions. DAD Retention time=6.79 min. M+H=320. $^1$H NMR (300 MHz, DMSO-d$_6$): δ8.71 (s, 1H), 7.97-7.89 (m, 1H), 7.79-7.69 (m, 1H), 7.67-7.50 (m, 2H), 7.24-7.04 (m, 4H), 6.62-6.59 (m, 2H), 5.88-5.82 (m, 2H), 4.57-4.47 (m, 2H), 4.34-4.24 (m, 2H).

Compounds in the following table were prepared from the appropriate starting materials in a method analogous to that described in the synthesis of 20.

| No. | LCMS Standard Method: (FA/AA) | ES+ | ES− | Retention Time (min) |
|---|---|---|---|---|
| 19 | AA | 340 | 338 | 5.89 |
| 20 | AA | 320 | 318 | 6.79 |

2-amino-9-(2-hydroxy-2-methylpropyl)-9H-pyrido[2,3-b]indole-3-carboxamide (43)

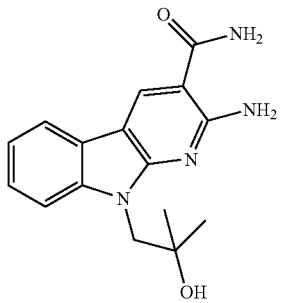

43

2-amino-9H-pyrido[2,3-b]indole-3-carboxamide (5, 200 mg, 0.884 mmol), isobutylene oxide (0.196 mL, 2.21 mmol) and cesium carbonate (460 mg, 1.40 mmol) in N,N-dimethylformamide (2.5 mL) were stirred at 100° C. under microwave irradiation for 10 min. The volatiles were removed in vacuo then the crude residue was adsorbed onto silica gel using methanol and purified by silica gel chromatography (5-10% methanol in methylene chloride gradient) to afford the title compound (43, 185 mg, 70%). $NH_4OAc$ standard conditions. DAD Retention time=5.93 min. M+H=299. $^1$H NMR (300 MHz, MeOD-$d_4$): δ8.64 (d, J=4.9 Hz, 1H), 7.88 (d, J=7.6 Hz, 1H), 7.55 (d, J=7.8 Hz, 1H), 7.34 (dd, J=7.6, 7.3 Hz, 1H), 7.20 (dd, J=7.8, 7.3 Hz, 1H), 5.49 (s, 2H), 1.28 (s, 6H).

Compounds in the following table were prepared from the appropriate starting materials in a method analogous to that described in the preparation of 43. In the case of 72, a TFA deprotection (following the procedure outlined in the preparation of 30) was utilized to generate the compound listed below.

| No. | LCMS Standard Method: (FA/AA) | ES+ | ES− | Retention Time (min) |
|---|---|---|---|---|
| 43 | AA | 299 | | 5.93 |
| 53 | AA | 311 | | 6.19 |
| 57 | AA | 285 | | 5.52 |
| 72 | AA | 326 | 324 | 4.43 |

2-amino-9-[(benzyloxy)acetyl]-9H-pyrido[2,3-b]indole-3-carboxamide (28)

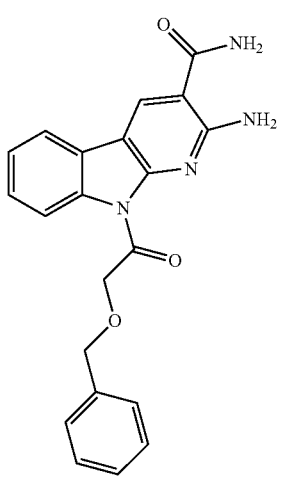

28

To a solution of 2-amino-9H-pyrido[2,3-b]indole-3-carboxamide (5, 150 mg, 0.663 mmol) in pyridine (7 mL) was added EDC (210 mg, 1.10 mmol), DMAP (85 mg, 0.693 mmol) and benzyloxyacetic acid (142 μL, 0.994 mmol) and the mixture was stirred at RT under an atmosphere of Ar. After 23 h, the reaction was quenched with water (20 mL), poured into a separatory funnel containing EtOAc (100 mL) and washed with water (75 mL). The organic layer was washed with brine (100 mL), dried over sodium sulfate, filtered and concentrated. The crude product was purified by HPLC (Phenomenex Luna 15 μm C18, aqueous $HCOOH/CH_3CN$) to yield 2-amino-9-[(benzyloxy)acetyl]-9H-pyrido[2,3-b]indole-3-carboxamide (28, 54 mg, 22%). $NH_4OAc$ standard conditions. DAD Retention time=7.6 min. M+H=375. $^1$H NMR (300 MHz, DMSO-$d_6$): δ 8.76 (s, 1H), 8.52-8.49 (m, 1H), 8.04 (br s, 1H), 7.83-7.77 (m, 3H), 7.47-7.29 (m, 8H), 5.30 (s, 2H), 4.72 (s, 2H).

Compounds in the following table were prepared from the appropriate starting materials in a method analogous to that described in the preparation of 28.

| No. | LCMS Standard Method: (FA/AA) | ES+ | ES− | Retention Time (min) |
|---|---|---|---|---|
| 27 | AA | 384 | 382 | 7.11 |
| 11 | AA | 346 | 344 | 6.3 |
| 28 | AA | 375 | | 7.6 |

2-amino-9-benzoyl-9H-pyrido[2,3-b]indole-3-carboxamide (8)

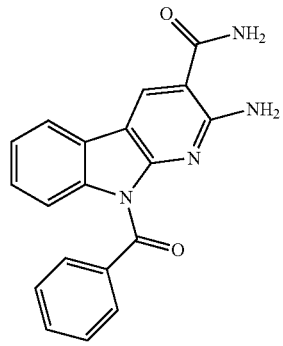

8

To a solution of 2-amino-9H-pyrido[2,3-b]indole-3-carboxamide (5, 42.0 mg, 0.186 mmol) in pyridine (1 mL) was added DMAP (57 mg, 0.467 mmol) and benzoyl peroxide (281 mg, 1.16 mmol). The mixture was stirred at RT. After 24 h, the reaction was concentrated, diluted with EtOAc (100 mL), poured into a separatory funnel and washed with water (2×75 mL). The organic layer was dried, filtered and concentrated. The crude was dissolved in EtOAc (100 mL) and washed with saturated aqueous $NaHCO_3$ (2×50 mL) and 1 N NaOH (50 mL). The organic layer was dried over sodium sulfate, filtered and concentrated to yield 2-amino-9-benzoyl-9H-pyrido[2,3-b]indole-3-carboxamide as a yellow solid (8, 34 mg, 56%). HCOOH standard conditions. DAD Retention time=6.65 min. M+H=331. $^1$H NMR (300 MHz, DMSO-$d_6$): δ8.78 (s, 1H), 8.04 (br s, 1H), 7.92-7.86 (m, 2H), 7.75-7.72 (m, 2H), 7.67 (d, J=7.5 Hz, 1H), 7.54-7.48 (m, 2H), 7.40-7.37 (m, 3H), 7.13 (br s, 2H).

Compounds in the following table were prepared from the appropriate starting materials in a method analogous to that described in the preparation of 8.

| No. | LCMS Standard Method: (FA/AA) | ES+ | ES− | Retention Time (min) |
|---|---|---|---|---|
| 6 | AA | 269 | 267 | 6.33 |
| 7 | FA | 297 | 295 | 6.97 |
| 8 | FA | 331 | | 6.65 |

2-amino-9-[(dimethylamino)sulfonyl]-9H-pyrido[2,3-b]indole-3-carboxamide (17)

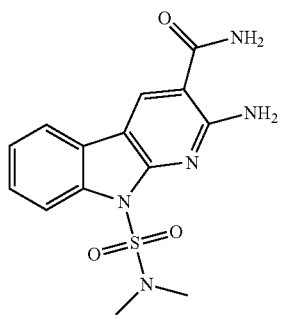

17

To a solution of 2-amino-9H-pyrido[2,3-b]indole-3-carboxamide (5, 138 mg, 0.610 mmol) in a 1:1 mixture of THF-DMF (4.5 mL) was added NaH (73.0 mg, 2.50 mmol). The mixture was stirred at RT. After 10-15 min, dimethylsulfamoyl chloride (212 mL, 1.10 mmol) was added and the reaction was stirred for another 2 h. The reaction was quenched with water (50 mL) and poured into a separatory funnel containing EtOAc (100 mL). The mixture was shaken and the layers were separated. The organic layer was washed with brine (50 mL), dried over sodium sulfate, filtered and concentrated. The crude product was purified by HPLC (Phenomenex Luna 15 μm C18, aqueous HCOOH/CH₃CN) to give 2-amino-9-[(dimethylamino)sulfonyl]-9H-pyrido[2,3-b]indole-3-carboxamide as a white powder (17, 24.9 mg, 12%). HCOOH standard conditions. DAD Retention time=3.68 min. M+H=334. $^1$H NMR (300 MHz, DMSO-$d_6$): δ 8.78 (s, 1H), 8.06 (s, 1H), 8.00-7.97 (m, 1H), 7.84-7.81 (m, 1H), 7.72 (br s, 2H), 7.40-7.32 (m, 3H), 3.02 (s, 6H).

Example 3

Deprotection of 9-N substituted α-carbolines

Scheme IV

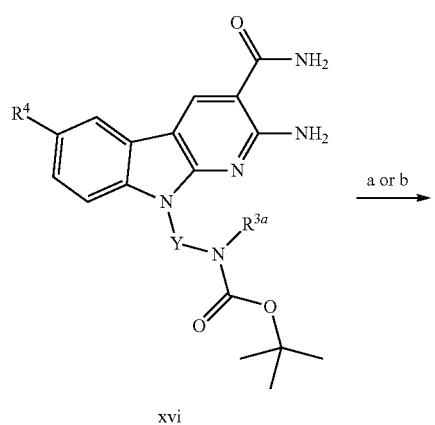

xvi

-continued

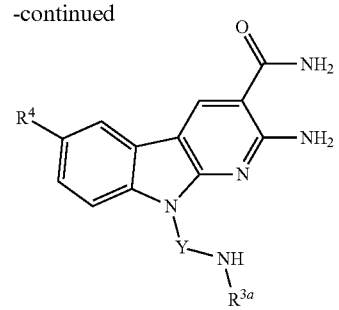

xvii

Y = —V₁—T₁— or —T₁— c →

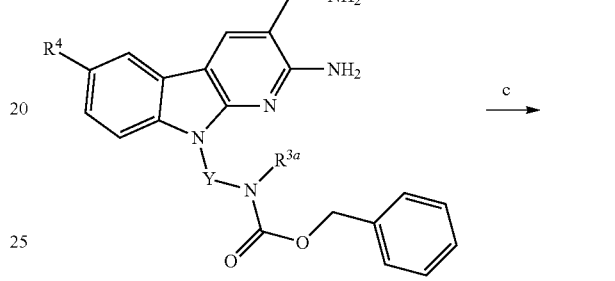

xxiv

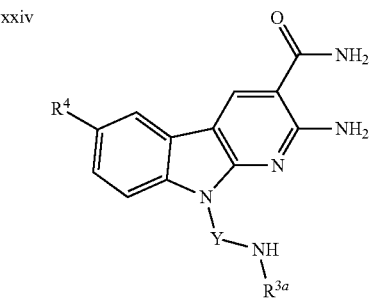

xvii

Y = —V₁—T₁— or —T₁—

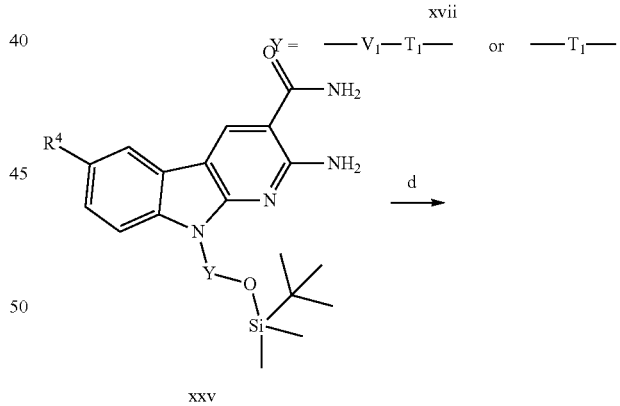

xxv d →

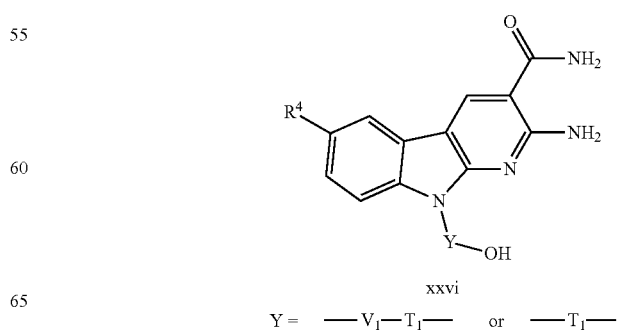

xxvi

Y = —V₁—T₁— or —T₁—

-continued

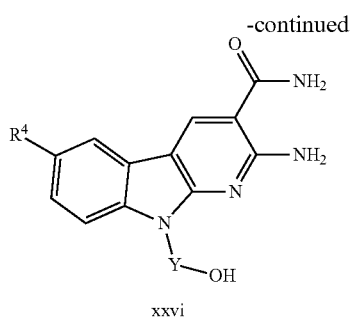

xxvi

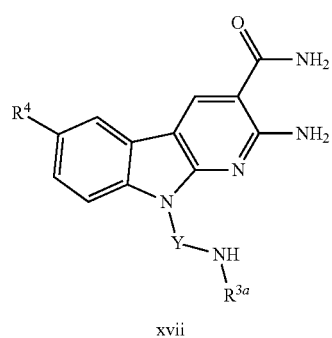

xvii $$Y = -V_1-T_1- \text{ or } -T_1-$$

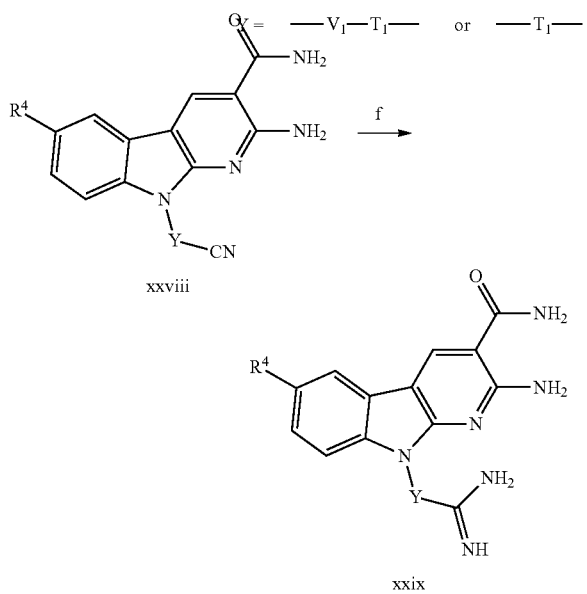

xxviii xxix

Steps: (a) Conc. HCl, MeOH (b) TFA, DCM (c) Pd/C, EtOH, H₂ (d) Br—V₁—T₁— TBAF, THF (e) i. ClCH₂CN, H₂SO₄, ii. (NH₂)₂C=S (f) i. HCl, EtOH ii. NH₃, MeOH 2-amino-9-(2-aminoethyl)-9H-pyrido[2,3-b]indole-3-carboxamide hydrochloride (16)

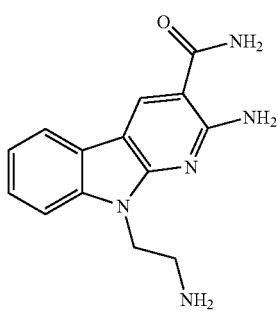

16

Step 1: tert-butyl {2-[2-amino-3-(aminocarbonyl)-9H-pyrido[2,3-b]indol-9-yl]ethyl}carbamate (xvi-a)

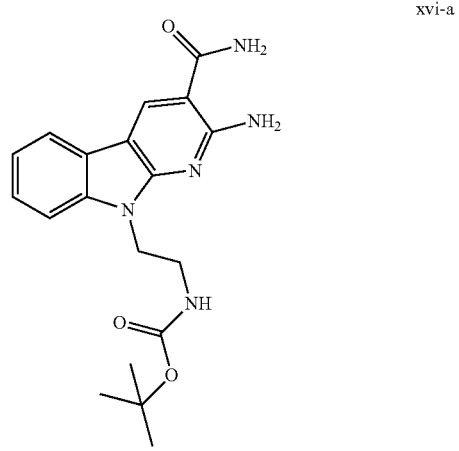

xvi-a tert-Butyl {2-[2-amino-3-(aminocarbonyl)-9H-pyrido[2,3-b]indol-9-yl]ethyl}carbamate was prepared following the procedure detailed in the synthesis of 13, substituting tert-butyl 2-bromoethylcarbamate for 2-bromopropane. NH₄OAc QC conditions M+H=370. ¹H NMR (300 MHz, DMSO-d₆): δ8.70 (s, 1H), 7.87 (br s, 1H), 7.77 (d, J=7.0 Hz, 1H), 7.56 (m, 2H), 7.44 (d, J=7.6 Hz, 1H), 7.29 (dd, J=7.0, 7.6 Hz, 1H), 7.15 (dd, J=7.6, 7.6 Hz, 1H), 6.96 (dd, J=5.9, 5.9 Hz, 1H), 4.32-4.21 (m, 2H), 3.34-3.20 (m, 2H), 1.28 (s, 9H).

Step 2: 2-amino-9-(2-aminoethyl)-9H-pyrido[2,3-b]indole-3-carboxamide hydrochloride (16)

To a solution of tert-butyl {2-[2-amino-3-(aminocarbonyl)-9H-pyrido[2,3-b]indol-9-yl]ethyl}carbamate (xvi-a, 35.0 mg, 0.095 mmol) in MeOH (2 mL) was added conc. HCl (1 mL). The reaction was stirred at RT. After 2 h, the reaction was concentrated and lyophilized to yield 2-amino-9-(2-aminoethyl)-9H-pyrido[2,3-b]indole-3-carboxamide hydrochloride as a white solid (16, 27 mg, 93%). NH₄OAc standard conditions. DAD Retention time=4.48 min. M+H=270. ¹H NMR (300 MHz, D₂O): δ8.16 (s, 1), 7.74 (d, J=7.6 Hz, 1H), 7.73-7.42 (m, 1H), 7.36-7.28 (m, 2H), 4.32 (t, J=5.7 Hz, 2H), 3.37 (t, J=5.7 Hz, 2H).

Compounds in the following table were prepared from the appropriate starting materials in a method analogous to that described in the preparation of 16.

| No. | LCMS Standard Method: (FA/AA) | ES+ | ES− | Retention Time (min) |
|---|---|---|---|---|
| 16 | Aa | 270 | | 4.48 |
| 15 | Aa | 284 | 282 | 4.68 |
| 25 | Aa | 284 | 282 | 5.22 |

2-amino-9-[(2S)-2-aminopropyl]-9H-pyrido[2,3-b]indole-3-carboxamide (30)

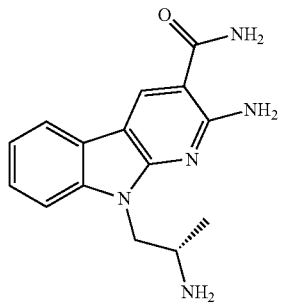

Step 1: tert-butyl[(1S)-2-iodo-1-methylethyl]carbamate (xxvii)

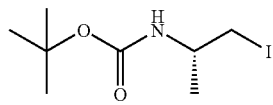

PS-triphenylphosphine (2.5 mmol/g, 1.3 g, 3.3 mmol) was suspended in methylene chloride (12 mL). Imidazole (225 mg, 3.3 mmol) was added and the mixture was cooled to 0° C. in an ice-water bath. To the cooled mixture was added iodine (838 mg, 3.3 mmol), and the resulting mixture was warmed to room temperature, stirred 10 minutes and recooled to 0° C. Boc-L-alaninol (463 mg, 2.64 mmol) in methylene chloride (3 mL) was added over several minutes. The resulting mixture was stirred at 0° C. for 1 hour, warmed to room temperature and stirred 2 h. The mixture was filtered. The solids collected were washed thoroughly with ethyl acetate. The filtrate was washed with dilute aqueous HCl (3%), sodium thiosulfate (1 M), saturated aqueous sodium bicarbonate and brine. The extracts were then dried over magnesium sulfate, filtered and concentrated under reduced pressure. The crude tert-butyl [(1S)-2-iodo-1-methylethyl]carbamate (xxvii) was obtained as a yellow oil and used without further purification. $^1$H NMR (300 MHz, CDCl$_3$): δ 3.34-3.56 (m, 2H), 3.27 (dd, J=3.7, 9.8 Hz, 1H), 1.43 (s, 9H), 1.18 (d, J=6.7 Hz, 3H).

Step 2: tert-butyl {(1S)-2-[2-amino-3-(aminocarbonyl)-9H-pyrido[2,3-b]indol-9-yl]-1-methylethyl}carbamate (xvi-b)

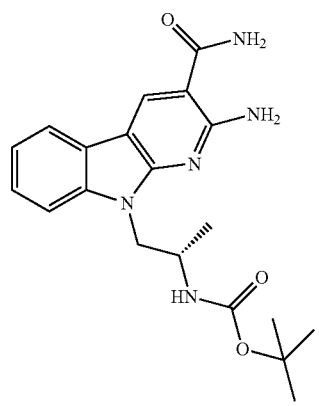

tert-butyl {(1S)-2-[2-amino-3-(aminocarbonyl)-9H-pyrido[2,3-b]indol-9-yl]-1-methylethyl}carbamate (xvi-b) was prepared following the procedure detailed in the synthesis of 13 substituting tert-butyl[(1S)-2-iodo-1-methylethyl]carbamate for 2-bromopropane. HCOOH Standard Conditions. M+H=384. $^1$H NMR (300 MHz, d$_6$-DMSO): δ 8.71 (s, 1H), 7.77 (d, J=7.3 Hz, 1H), 7.59 (d, J=7.9 Hz, 1H), 7.57-7.49 (br s, 2H), 7.31 (dd, J=7.9, 7.3 Hz, 1H), 7.16 (dd, J=7.9, 7.3 Hz, 1H), 6.90 (br d, 1H), 4.27 (dd, J=6.1, 13.4 Hz, 1H), 4.14-3.95 (m, 2H), 1.18 (s, 9H), 1.05 (d, J=6.1 Hz, 3H)

Step 3: 2-amino-9-[(2S)-2-aminopropyl]-9H-pyrido[2,3-b]indole-3-carboxamide (30)

tert-Butyl {(1S)-2-[2-amino-3-(aminocarbonyl)-9H-pyrido[2,3-b]indol-9-yl]-1-methylethyl}carbamate (xvi-b, 400. mg, 1.04 mmol), was dissolved in methylene chloride (10 mL) to which trifluoroacetic acid (2 mL) was subsequently added. The mixture was stirred at room temperature until consumption of starting material was complete. The reaction mixture was diluted with ethyl acetate (20 mL) and basified by addition of 6 N aqueous sodium hydroxide solution. The extracts were washed with brine, dried over sodium sulfate, filtered and concentrated. The crude material was dissolved in minimal methanol and then acidified by the addition of HCl in ether (1 M). The pure product was isolated as its hydrochloride salt by filtration (196 mg, 59%). NH$_4$OAc standard conditions. DAD Retention time=4.92 min. M+H=284. $^1$H NMR (300 MHz, CD$_3$OD): δ 8.77 (s, 1H), 7.95 (d, J=7.6 Hz, 1H), 7.53 (d, J=8.2 Hz, 1H), 7.43 (dd, J=8.2, 7.0 Hz, 1H), 7.28 (dd, J=7.6, 7.0 Hz, 1H), 4.62-4.47 (m, 2H), 4.01-3.89 (m, 1H), 1.40 (d, J=6.5 Hz, 3H).

Compounds in the following table were prepared from the appropriate starting materials in a method analogous to that described in the preparation of 30.

| No. | LCMS Standard Method: (FA/AA) | ES+ | ES– | Retention Time (min) |
| --- | --- | --- | --- | --- |
| 30 | AA | 284 | | 4.92 |
| 31 | AA | 284 | 282 | 4.8 |
| 39 | FA (QC conditions) | 298 | | 0.97 (QC conditions) |
| 41 | FA | 312 | | 3.99 |

2-amino-9-[(2R)-2-aminopropyl]-9H-pyrido[2,3-b]indole-3-carboxamide (35)

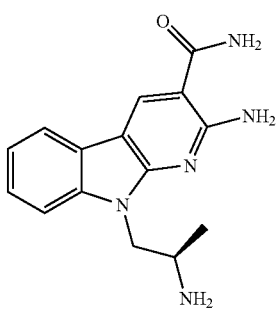

Step 1: benzyl {(1R)-2-[2-amino-3-(aminocarbonyl)-9H-pyrido[2,3-b]indol-9-yl]-1-methylethyl}carbamate (xxiv-a)

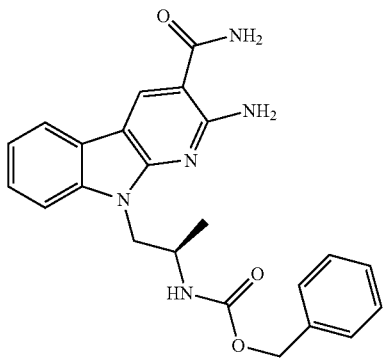

xxiv-a benzyl {(1R)-2-[2-amino-3-(aminocarbonyl)-9H-pyrido[2,3-b]indol-9-yl]-1-methylethyl}carbamate (xxiv-a) was prepared following the procedure detailed in the synthesis of 13, substituting benzyl[(1R)-2-iodo-1-methylethyl]carbamate (made from commercial N-benzyloxycarbonyl-D-alaninol) for 2-iodopropane.

Step 2: 2-amino-9-[(2R)-2-aminopropyl]-9H-pyrido[2,3-b]indole-3-carboxamide (35)

To a solution of benzyl {(1R)-2-[2-amino-3-(aminocarbonyl)-9H-pyrido[2,3-b]indol-9-yl]-1-methylethyl}carbamate (xxiv-a, 13 mg, 0.031 mmol) in ethanol (10 mL) was added palladium on carbon (10 mg, 0.094 mmol). The reaction mixture was stirred under a hydrogen atmosphere overnight. Solids were removed by filtration and the filtrate was concentrated in vacuo to afford 2-amino-9-[(2R)-2-aminopropyl]-9H-pyrido[2,3-b]indole-3-carboxamide (35, 7.6 mg, 86%). NH$_4$OAc standard conditions. DAD Retention time=4.90 min. M+H=284. $^1$H NMR (300 MHz, MeOD-d$_4$): $\delta$8.66 (s, 1H), 7.90 (d, J=7.7 Hz, 1H) 7.49 (d, J=8.1 Hz, 1H), 7.23 (ddd, J=7.4, 6.9, 1.2 Hz, 1H), 7.17 (ddd, J$_1$=7.8, 7.7, 1.2 Hz, 1H), 4.33 (d, J=6.1 Hz, 2H), 3.63-3.71 (m, 1H), 1.23 (d, J=6.5 Hz, 3H).

Compounds in the following table were prepared from the appropriate starting materials in a method analogous to that described in the preparation of 35.

| No. | LCMS Standard Method: (FA/AA) | ES+ | ES− | Retention Time (min) |
|---|---|---|---|---|
| 26 | AA | 284 | 282 | 5.2 |
| 35 | AA | 284 | | 4.9 |

2-amino-9-(2-hydroxyethyl)-9H-pyrido[2,3-b]indole-3-carboxamide (9)

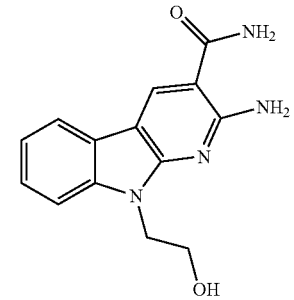

9

Step 1: 2-amino-9-(2-(tert-butyldimethylsilyloxy)ethyl)-9H-pyrido[2,3-b]indole-3-carboxamide (xxv-a)

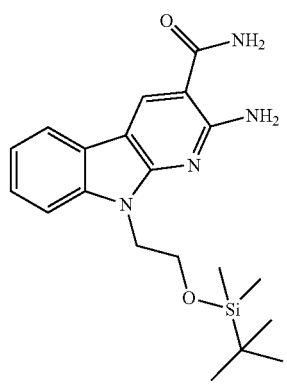

xxv-a

2-Amino-9-(2-(tert-butyldimethylsilyloxy)ethyl)-9H-pyrido[2,3-b]indole-3-carboxamide (xxv-a) was prepared following the procedure detailed in the synthesis of 13 substituting (2-bromoethoxy)(tert-butyl)dimethylsilane for 2-bromopropane. The crude silane was used in the following step without further purification. NH$_4$OAc QC conditions. M+H=385.

Step 2: 2-amino-9-(2-hydroxyethyl)-9H-pyrido[2,3-b]indole-3-carboxamide (9)

2-Amino-9-(2-(tert-butyldimethylsilyloxy)ethyl)-9H-pyrido[2,3-b]indole-3-carboxamide (xxv-a, 360 mg, 1.06 mmol) was dissolved in tetrahydrofuran (3 mL). A solution of tetrabutylammonium fluoride (1.0 M in THF, 1.3 mL, 1.4 mmol) was added. The resulting solution was stirred at room temperature 3 h. The solution was concentrated under reduced pressure. The residue was triturated with methylene chloride. The resulted solids were dissolved in tetrahydrofuran and washed with brine. The extracts were dried over sodium sulfate, filtered and concentrated under reduced pressure. The crude product was purified by silica gel chromatography (12 g silica, methylene chloride to 3% methanol in methylene chloride gradient). The product 9 was isolated as a yellow solid (30 mg, 10% for 2 steps). NH$_4$OAc standard conditions. DAD retention time=5.02 min. M+H=271. $^1$H NMR (300 MHz, DMSO-d$_6$): δ8.66 (s, 1H), 7.73 (d, J=7.6 Hz, 1H), 7.59-7.50 (br s, 1H), 7.46 (d, J=8.2 Hz, 1H), 7.25 (ddd, J=1.7, 7.0, 8.2 Hz, 1H), 7.11 (dd, J=7.0, 7.0 Hz, 1H), 4.30-4.23 (m, 2H), 3.72-3.66 (m, 2H).

Compounds in the following table were prepared from the appropriate starting materials in a method analogous to that described the preparation of 9.

| No. | LCMS Standard Method: (FA/AA) | ES+ | ES− | Retention Time (min) |
|---|---|---|---|---|
| 9 | AA | 271 | 269 | 5.02 |
| 12 | AA | 285 | 283 | 5.37 |

Example 16a 2-amino-9-{2-amino-1-[(benzyloxy)methyl]ethyl}-9H-pyrido[2,3-b]indole-3-carboxamide (73)

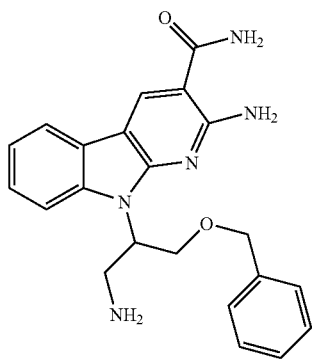

73

Step 1: tert-Butyl 3-[2-amino-3-(aminocarbonyl)-9H-pyrido[2,3-b]indol-9-yl]azetidine-1-carboxylate (xvi-c)

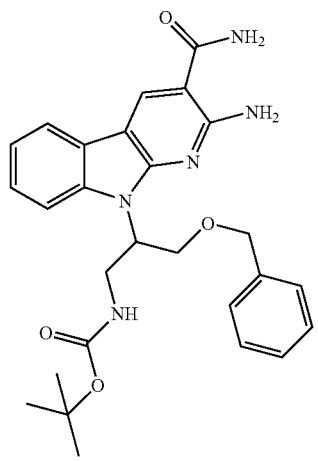

xvi-c tert-Butyl 3-[2-amino-3-(aminocarbonyl)-9H-pyrido[2,3-b]indol-9-yl]azetidine-1-carboxylate (xvi-c) was prepared following the procedure detailed in the synthesis of 63, substituting tert-butyl[3-(benzyloxy)-2-iodopropyl]carbamate (prepared from tert-butyl 3-(benzyloxy)-2-hydroxypropylcarbamate [Nagashima, N. Chem. Pharm. Bull. 1991, 39, 1972-1982] as detailed in the preparation of xxvii) for tert-butyl[1-(iodomethyl)cyclopropyl]carbamate. NH$_4$OAc QC conditions. M+H=382 tert-Butyl 3-[2-amino-3-(aminocarbonyl)-9H-pyrido[2,3-b]indol-9-yl]azetidine-1-carboxylate (xvi-c) was used directly in the following deprotection step.

Step 2: 2-Amino-9-{2-amino-1-[(benzyloxy)methyl]ethyl}-9H-pyrido[2,3-b]indole-3-carboxamide hydrochloride (73)

Deprotection of xvi-c following the HCl/methanol deprotection procedure detailed in the second step of the synthesis of 16 afforded 2-amino-9-{2-amino-1-[(benzyloxy)methyl]ethyl}-9H-pyrido[2,3-b]indole-3-carboxamide hydrochloride (73, 11 mg, 5%). NH$_4$OAc standard conditions. DAD Retention time=6.72 min. M+1=282. $^1$H NMR (300 MHz, MeOD): δ 8.88 (s, 1H), 7.96 (d, J=7.6 Hz, 1H), 7.54 (d, J=8.2 Hz, 1H), 7.44 (t, J=7.6 Hz, 1H), 7.35-7.22 (m, 7H), 4.70 (d, J=6.4 Hz, 2H), 4.52-4.50 (m, 2H), 4.10-3.96 (m, 1H), 3.75-3.38 (m, 1H), 3.60-3.50 (m, 1H).

2-amino-9-[(2R)-2-amino-3-(benzyloxy)propyl]-9H-pyrido[2,3-b]indole-3-carboxamide (61)

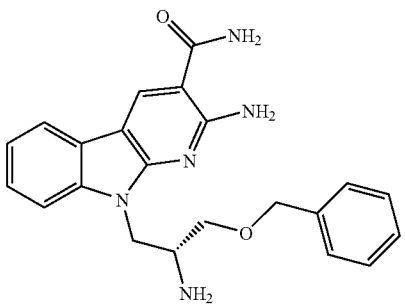

61

Step 1: (R)-tert-butyl 1-(2-amino-3-carbamoyl-9H-pyrido[2,3-b]indol-9-yl)-3-(benzyloxy)propan-2-ylcarbamate (xvi-d)

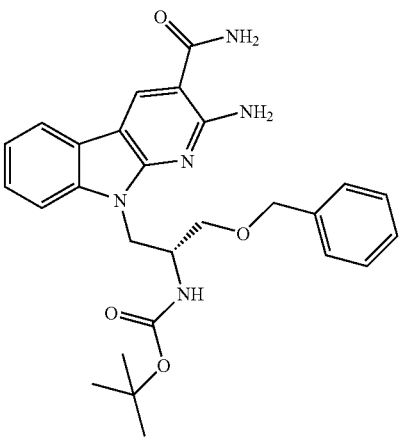

xvi-d (R)-tert-butyl 1-(2-amino-3-carbamoyl-9H-pyrido[2,3-b]indol-9-yl)-3-(benzyloxy)propan-2-ylcarbamate (xvi-d) was prepared following the procedure detailed in the preparation of 63, substituting (S)-tert-butyl 1-(benzyloxy)-3-iodopropan-2-ylcarbamate (prepared as detailed in the synthesis of xxvii from commercial N-Boc-L-Ser(Bzl)-ol) for tert-butyl [1-(iodomethyl)cyclopropyl]carbamate. NH$_4$OAc QC conditions. M+H=490.

Step 2: 2-Amino-9-[(2R)-2-amino-3-(benzyloxy)propyl]-9H-pyrido[2,3-b]indole-3-carboxamide hydrochloride (61)

2-Amino-9-[(2R)-2-amino-3-(benzyloxy)propyl]-9H-pyrido[2,3-b]indole-3-carboxamide hydrochloride (61) was obtained from xvi-d following the TFA deprotection procedure outlined in the preparation of 30 to yield the titled compound (61, 20 mg, 70%). NH$_4$OAc standard conditions. DAD Retention time=6.70 min. M+H=390. $^1$H NMR (300 MHz, DMSO-d$_6$): δ 8.78 (s, 1H), 7.82 (d, J=7.3 Hz, 1H), 7.61 (d, J=7.94 Hz, 1H), 7.36-7.20 (m, 8H), 4.62-4.42 (m, 2H), 4.48 (s, 2H), 3.88-3.80 (m, 1H), 3.64-3.44 (m, 2H).

Compounds in the following table were prepared from the appropriate starting materials in a method analogous to that described in the synthesis of 61.

| No. | LCMS Standard Method: (FA/AA) | ES+ | ES− | Retention Time (min) |
|-----|-------------------------------|-----|-----|----------------------|
| 61  | AA                            | 390 | 388 | 6.70                 |
| 64  | AA                            | 296 |     | 5.46                 |

2-Amino-9-[(2R)-2-amino-3-hydroxypropyl]-9H-pyrido[2,3-b]indole-3-carboxamide (65)

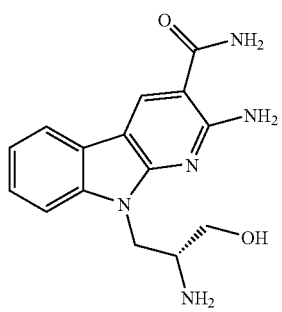

65

To a cooled (0° C.) solution of 2-amino-9-[(2R)-2-amino-3-(benzyloxy)propyl]-9H-pyrido[2,3-b]indole-3-carboxamide (61, 81 mg, 0.160 mmol) in chloroform (2 mL) was added iodotrimethylsilane (140 uL, 0.990 mmol). The reaction was stirred under argon, allowed to warm slowly to room temperature and then stirred an additional 16 h. The reaction mixture was filtered and concentrated in vacuo. The crude mixture was purified by reverse phase HPLC (Phenomenex Luna 15 μm C18, aqueous NH$_4$OAc/CH$_3$CN) to provide the product which was then converted to the hydrochloride salt by stirring with a solution of excess hydrochloric acid in methanol to afford 2-amino-9-[(2R)-2-amino-3-hydroxypropyl]-9H-pyrido[2,3-b]indole-3-carboxamide (65, 24 mg, 45%). NH$_4$OAc standard conditions. DAD Retention time=4.76 min. M+H=300. $^1$H NMR (300 MHz, MeOD-d$_4$): δ8.97 (s, 1H), 8.01 (d, J=7.0 Hz, 1H) 7.67 (d, J=7.4 Hz, 1H), 7.52 (t, J=6.9, 1H), 7.38 (t, J=6.9 Hz, 1H), 4.75-4.69 (m, 2H), 3.96-3.81 (m, 2H), 3.71-3.62 (m, 1H).

2-amino-9-(pyrrolidin-2-ylmethyl)-9H-pyrido[2,3-b]indole-3-carboxamide (40)

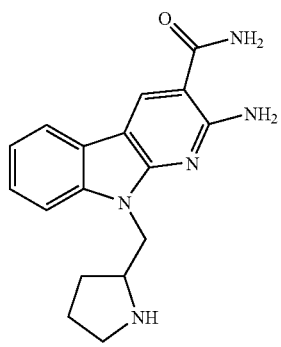

40

Step 1: tert-butyl 2-{[2-amino-3-(aminocarbonyl)-9H-pyrido[2,3-b]indol-9-yl]-methyl}pyrrolidine-1-carboxylate (xvi-e)

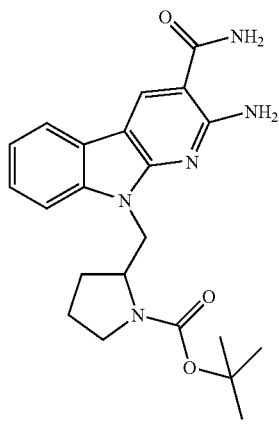

xvi-e

To a solution of 2-amino-9H-pyrido[2,3-b]indole-3-carboxamide (5, 50 mg, 0.2 mmol) in N,N-dimethylformamide (0.5 mL) was added powdered sodium hydroxide (12 mg, 0.31 mmol) and tetrabutylammonium hydrogen sulfate (3 mg, 0.009 mmol). The mixture was stirred at room temperature for 30 min then tert-butyl 2-(bromomethyl)pyrrolidine-1-carboxylate (67 mg, 0.25 mmol) was added. The resulting mixture was stirred at room temperature for 4 days. Water (5 ml) was added to the mixture, followed by HCl (3% aqueous, 1 mL). The mixture was extracted with ethyl acetate (3×30 ml). The extracts were combined, dried over sodium sulfate, filtered and concentrated under reduced pressure. The crude product was purified by silica gel chromatography (12 g silica, methylene chloride to 90/10 methylene chloride/methanol gradient) to yield tert-butyl 2-{[2-amino-3-(aminocarbonyl)-9H-pyrido[2,3-b]indol-9-yl]methyl}pyrrolidine-1-carboxylate (xvi-e, 20 mg, 20%). NH$_4$OAc QC conditions. M+1=410.

Step 2: 2-amino-9-(pyrrolidin-2-ylmethyl)-9H-pyrido[2,3-b]indole-3-carboxamide 2-Amino-9-(pyrrolidin-2-ylmethyl)-9H-pyrido[2,3-b]indole-3-carboxamide (40) was obtained following the TFA deprotection of xvi-e as detailed in the preparation of 30 to yield the title compound (40, 18 mg, 70%). NH$_4$OAc standard conditions. DAD Retention time=5.13 min. M+H=310. $^1$H NMR (300 MHz, MeOD): δ 8.82 (s, 1H), 7.95 (d, J=7.3 Hz, 1H), 7.61 (d, J=7.3 Hz, 1H), 7.45 (t, J=6.9 Hz, 1H), 7.31 (t, J=6.9 Hz, 1H), 4.78-4.70 (m, 2H), 4.20-4.05 (m, 1H), 3.55-3.44 (m, 1H), 2.37-2.22 (m, 1H), 2.12-1.97 (m, 3H), 1.93-1.78 (m, 1H).

2-amino-9-azetidin-3-yl-9H-pyrido[2,3-b]indole-3-carboxamide (50)

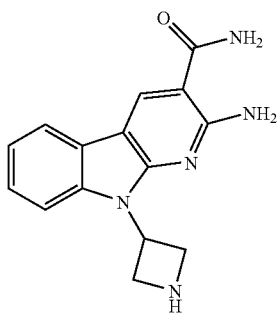

Step 1: tert-butyl 3-[2-amino-3-(aminocarbonyl)-9H-pyrido[2,3-b]indol-9-yl]azetidine-1-carboxylate (xvi-f)

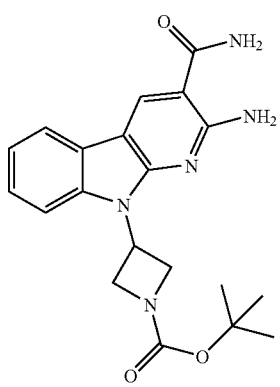

xvi-f

To a stirred solution of 2-amino-9H-pyrido[2,3-b]indole-3-carboxamide (5, 44 mg, 0.19 mmol) in N,N-dimethylformamide (4.4 mL) was added powdered cesium carbonate (130 mg, 0.39 mmol), and tert-butyl 3-iodoazetidine-1-carboxylate (Harris, L. J., et al. European Patent Application 1176142, 2002; 0.11 g, 0.39 mmol). The mixture was heated in a microwave at 150° C. for 30 min, concentrated and purified by silica gel chromatography (12 g silica, methylene chloride to 90/10 methylene chloride/methanol gradient) to yield tert-butyl 3-[2-amino-3-(aminocarbonyl)-9H-pyrido[2,3-b]indol-9-yl]azetidine-1-carboxylate (xvi-f, 50 mg, 70%).

NH$_4$OAc QC conditions. M+H=382. $^1$H NMR (300 MHz, CDCl$_3$): δ 8.24 (s, 1H), 7.83 (d, J=7.9 Hz, 1H), 7.60 (d, J=7.9 Hz, 1H), 7.42-7.34 (m, 1H), 7.30-7.22 (m, 1H), 4.75-4.60 (m, 1H), 4.48-4.39 (m, 2H), 4.17-4.07 (m, 2H), 1.51 (s, 9H).

Step 2: 2-amino-9-azetidin-3-yl-9H-pyrido[2,3-b]indole-3-carboxamide (50)

2-Amino-9-azetidin-3-yl-9H-pyrido[2,3-b]indole-3-carboxamide (50) was made following the trifluoroacetic acid deprotection procedure detailed in the preparation of 30 affording the titled compound (50, 20 mg, 40%). NH$_4$OAc standard conditions. DAD Retention time=4.97 min. M+H=282. $^1$H NMR (300 MHz, MeOD): δ 8.72 (s, 1H), 7.90 (d, J=6.9 Hz, 1H), 7.48-7.30 (m, 2H), 7.27-7.22 (m, 1H), 4.78-4.50 (m, 1H), 4.30-4.20 (m, 2H), 3.85-4.00 (m, 2H).

Compounds in the following table were prepared from the appropriate starting materials (mesylate or iodide) in a method analogous to that described in the preparation of 50.

| No. | LCMS Standard Method: (FA/AA) | ES+ | ES− | Retention Time (min) |
|---|---|---|---|---|
| 52 | AA | 298 | 296 | 5.28 |
| 50 | AA | 282 | | 4.97 |

2-amino-9-{2-[(chloroacetyl)amino]-2-methylpropyl}-9H-pyrido[2,3-b]indole-3-carboxamide (56)

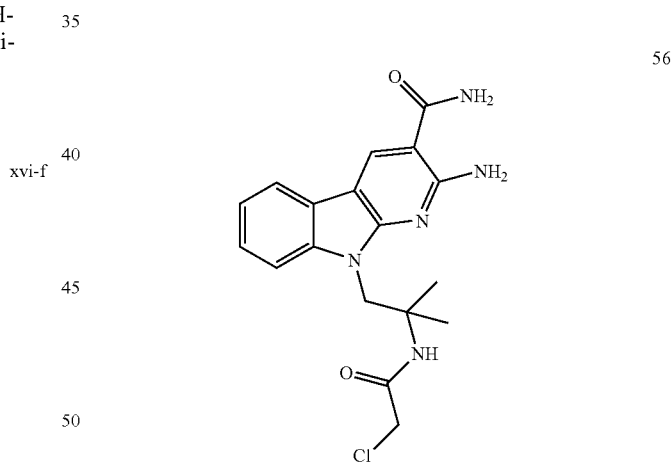

56

Concentrated sulfuric acid (1.0 mL) was added dropwise to a solution of 43 (120 mg, 0.102 mmol) in chloroacetonitrile (1.0 mL) at 0° C. Stirring continued at this temperature for 1 h, then the reaction was diluted with water (5 mL) and the pH adjusted to 8-9 with 1N sodium hydroxide then aqueous saturated sodium bicarbonate. The aqueous phase was extracted with ethyl acetate (50 mL×3) then the combined organic phases were dried over sodium sulfate and concentrated in vacuo. The residue was purified by silica gel chromatography (5-10% methanol in methylene chloride gradient) to afford the title compound (56, 120 mg, 80%). NH$_4$OAc standard conditions. DAD Retention time=6.59 min. M+H=374. $^1$H NMR (300 MHz, CDCl$_3$): δ8.39 (br s, 1H), 8.27 (s, 1H), 7.80 (d, J=7.3 Hz, 1H), 7.36-7.34 (m, 2H), 7.22

(dd, J=7.3, 7.3 Hz, 1H), 6.83 (br s, 2H), 5.80 (br s, 2H), 4.28 (s, 2H), 3.87 (s, 2H), 1.55 (s, 6H).

2-amino-9-{2-[(chloroacetyl)amino]-2-methylpropyl}-9H-pyrido[2,3-b]indole-3-carboxamide (47)

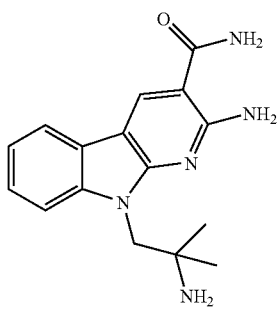

47

A solution of 56 (50 mg, 0.134 mmol) and thiourea (21 mg, 0.28 mmol) in ethanol (1.0 mL) was stirred under microwave irradiation for 15 min at 150° C. After cooling to room temperature the reaction was diluted with saturated aqueous sodium bicarbonate solution (10 mL) and extracted with ethyl acetate (3×20 mL). The combined organic phases were washed with brine, dried over sodium sulfate, filtered and concentrated in vacuo to afford the title compound (47, 24 mg, 60%). NH$_4$OAc standard conditions. DAD Retention time=5.24 min. M+H=298. $^1$H NMR (300 MHz, MeOD-d$_4$): δ8.70 (br s, 1H), 8.37 (s, 1H), 7.92 (d, J=7.7 Hz, 1H), 7.53 (d, J=8.1 Hz, 1H), 7.40 (dd, J=7.7, 7.3 Hz, 1H), 7.26 (dd, J=8.1, 7.3 Hz, 1H), 4.44 (s, 2H), 1.50 (s, 6H).

2-amino-9-(2-amino-2-iminoethyl)-9H-pyrido[2,3-b]indole-3-carboxamide (42)

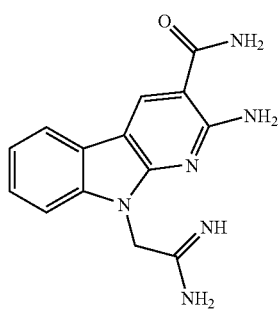

42

Hydrogen chloride gas was bubbled through ice-cooled absolute ethanol (15 mL) for 5 min to prepare a saturated solution. 2-Amino-9-(cyanomethyl)-9H-pyrido[2,3-b]indole-3-carboxamide (36, 29 mg, 0.107 mmol) in ethanol (1 mL) was added, the resulting solution stirred at room temperature for 90 min and then all volatiles were removed in vacuo. The resulting residue was diluted with ammonia in methanol (7.0 M, 10.0 mL) and stirred at room temperature for 16 h. The crude reaction mixture was concentrated in vacuo and the residue purified by reverse phase C-18 silica gel chromatography [0-70% acetonitrile in water (containing 0.1% TFA)] to afford the title compound (42, 28 mg, 91%) as the trifluoroacetate salt. NH$_4$OAc standard conditions. DAD Retention time=4.53 min. M+H=311. $^1$H NMR (300 MHz, DMSO-d$_6$): δ8.95 (br s, 1H), 8.91 (br s, 1H), 8.77 (s, 1H), 7.94 (br s, 1H), 7.83 (d, J=7.3 Hz, 1H), 7.65 (br s, 1H), 7.50 (d, J=7.9 Hz, 1H), 7.35 (dd, J=7.9, 7.3 Hz, 1H), 7.26 (dd, J=7.3, 7.3 Hz, 1H), 5.22 (s, 2H).

Compounds in the following table were prepared from the appropriate starting materials in a method analogous to that described in the preparation of 42.

| No. | LCMS Standard Method: (FA/AA) | ES+ | ES− | Retention Time (min) |
|---|---|---|---|---|
| 42 | AA | 283 | | 4.16 |
| 58 | AA | 311 | | 4.53 |
| 59 | AA | 309 | 307 | 4.49 |

Example 4

Synthesis of compounds where R$^3$ is T$_1$-R$^{3d}$ or —V$_1$-T$_1$-R$^{3d}$ and T$_1$ is substituted with —NR'C(O)R$^{3a}$ or NC(=N)NH$_2$ Scheme V

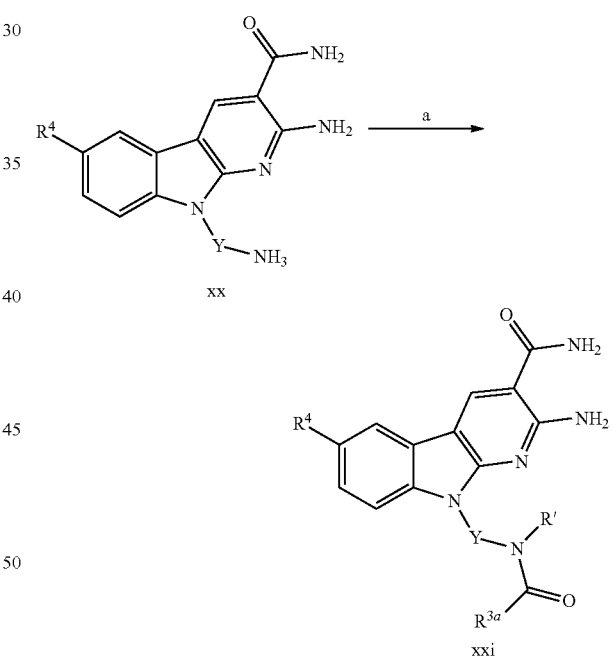

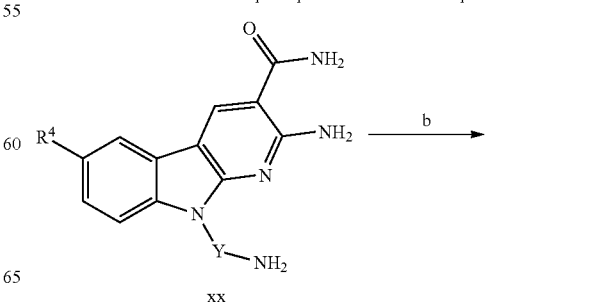

91
-continued

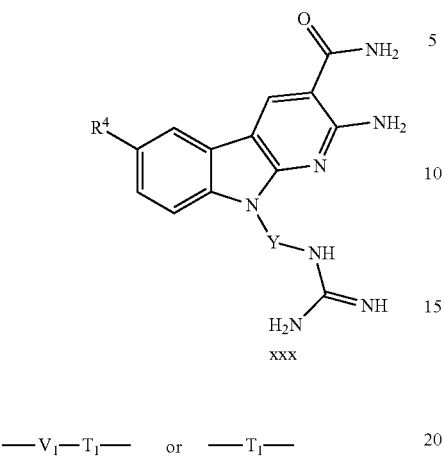

Y = —V₁—T₁— or —T₁—

Steps: (a) [R³ᵃC(O)]₂O, DMAP, pyridine (b) i. N,N'-bis-tert-butoxycarbonylthiourea, PL-DCC 9-[2-(acetylamino)ethyl]-2-amino-9H-pyrido[2,3-b]indole-3-carboxamide (22)

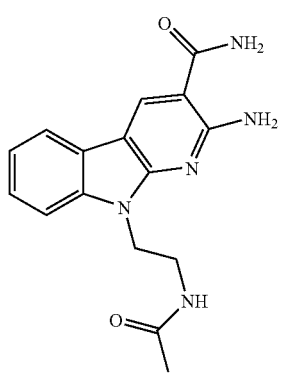

To a solution of 2-amino-9-(2-aminoethyl)-9H-pyrido[2,3-b]indole-3-carboxamide (16, 50.0 mg, 0.186 mmol) in pyridine (2 mL) was added DMAP (23.0 mg, 0.188 mmol) and acetic anhydride (23 μL, 0.243 mmol). The reaction was stirred at RT under an atmosphere of argon. After 1 h, the reaction was concentrated and the crude product was purified by HPLC (Phenomenex Luna 15 μm C18, aqueous NH₄OAc/CH₃CN) to yield 9-[2-(acetylamino)ethyl]-2-amino-9H-pyrido[2,3-b]indole-3-carboxamide (22, 11 mg, 19%). NH₄OAc standard conditions. DAD Retention time=5.18 min. M+H=312. ¹H NMR (300 MHz, DMSO-d₆): δ 8.73 (s, 1H), 8.01 (t, J=5.7 Hz, 1H), 7.80 (d, J=7.5 Hz, 1H), 7.58 (br s, 2H), 7.46 (d, J=8.1 Hz, 1H), 7.33 (t, J=8.1 Hz, 1H), 7.18 (t, J=7.5 Hz, 1H), 4.31 (t, J=6.0 Hz, 2H), 3.41 (q, J=6.0 Hz, 2H), 1.71 (s, 3H).

92

2-amino-9-((2S)-2-{[amino(imino)methyl]amino}propyl)-9H-pyrido[2,3-b]indole-3-carboxamide (71)

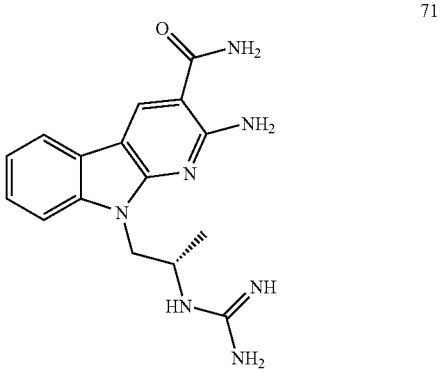

To a solution of 2-amino-9-[(2S)-2-aminopropyl]-9H-pyrido[2,3-b]indole-3-carboxamide (30, 100 mg, 0.350 mmol) in methylene chloride (3 mL) was added PL-DCC resin (394 mg, 0.575 mmol) and the mixture was stirred at room temperature for 15 min. N,N'-bis-tert-butoxycarbonylthiourea (112 mg, 0.406 mmol) was added and the reaction mixture was stirred at room temperature overnight. PS-trisamine resin (4.12 g, 3.6 mmol/g, 14.8 mmol) was subsequently added and the resulting mixture was stirred at room temperature overnight. The resins were removed by suction filtration and the filtrate was concentrated under reduced pressure. Purification of the crude material by reverse phase C-18 silica gel chromatography [0-70% acetonitrile in water (containing 0.1% TFA)] afforded 2-amino-9-((2S)-2-{[amino(imino)methyl]amino}propyl)-9H-pyrido[2,3-b]indole-3-carboxamide (71, 48 mg 26%). NH₄OAc standard conditions. DAD Retention time=4.98 min. M+H=326.

Example 5

Synthesis of 2-amino-substituted compounds
(R¹=R¹ᵃ, —C(O)R¹ᵃ, —C(O)N(R¹ᵃ)₂)

Scheme VI

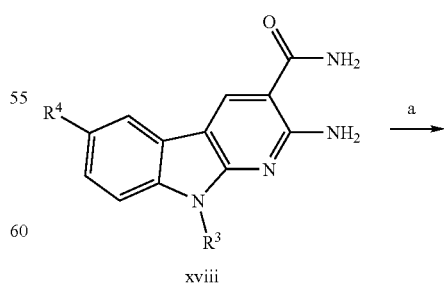

94

2-[(aminocarbonyl)amino]-9-ethyl-9H-pyrido[2,3-b]indole-3-carboxamide (21)

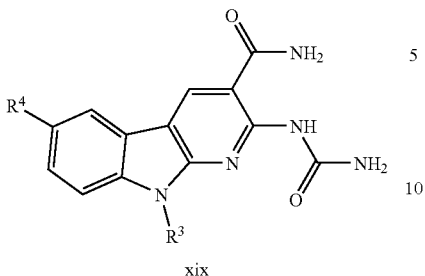

21

A solution of 2-amino-9-ethyl-9H-pyrido[2,3-b]indole-3-carboxamide (1, 71 mg, 0.28 mmol) in DCM (1 mL) was cooled to 0° C. and chlorosulfonyl isocyanate (27 µL, 0.31 mmol) was added. The mixture was stirred at 0° C. under an atmosphere of argon. After 2 h, the reaction was quenched with a few drops of water and concentrated under reduced pressure. The crude product was purified by HPLC (Phenomenex Luna 15 µm C18, aqueous $NH_4OAc/CH_3CN$) to yield 2-[(aminocarbonyl)amino]-9-ethyl-9H-pyrido[2,3-b]indole-3-carboxamide (21, 15 mg, 18%). $NH_4OAc$ standard conditions. DAD Retention time=6.40 min. M+H=298. $^1$H NMR (300 MHz, DMSO-$d_6$): δ 11.44 (s, 1H), 9.04 (s, 1H), 8.70 (br s, 1H), 8.30 (br s, 1H), 7.99 (d, J=7.6 Hz, 1H), 7.69 (d, J=8.1 Hz, 2H), 7.49 (t, J=8.1 Hz, 1H), 7.32 (t, J=7.6 Hz, 1H), 7.24 (br s, 1H), 4.42 (q, J=7.1 Hz, 2H), 1.35 (t, J=7.1 Hz, 3H).

2-(acetylamino)-9-[(2S)-2-aminopropyl]-9H-pyrido[2,3-b]indole-3-carboxamide (66)

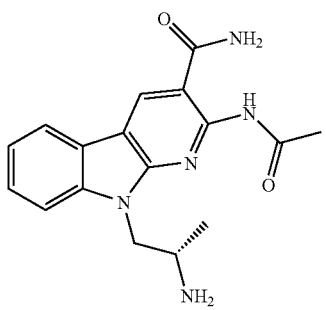

66

Step 1: tert-butyl {(1S)-2-[2-(acetylamino)-3-(aminocarbonyl)-9H-pyrido[2,3-b]indol-9-yl]-1methylethyl}carbamate (xxxi-a)

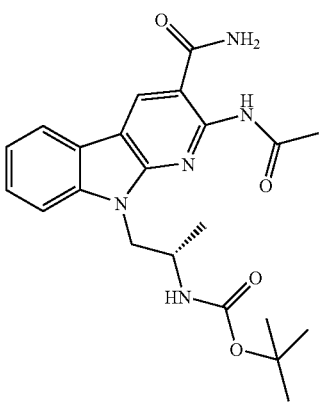

xxxi-a

93

-continued

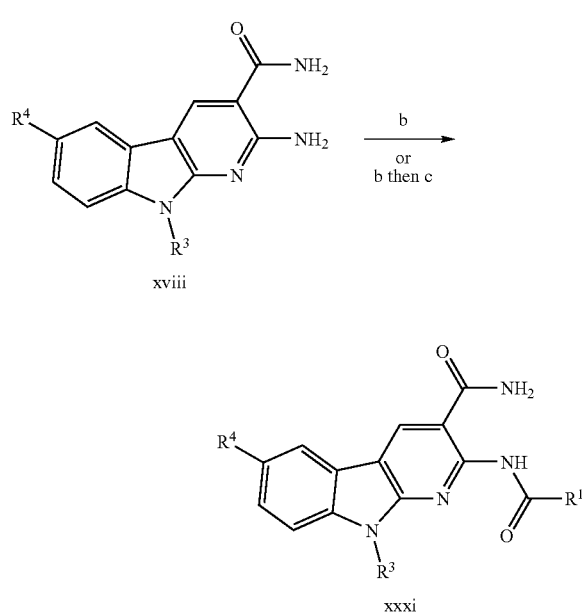

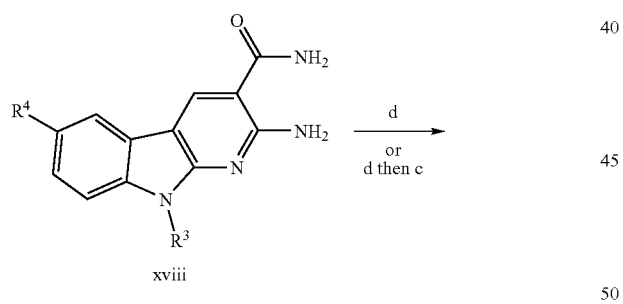

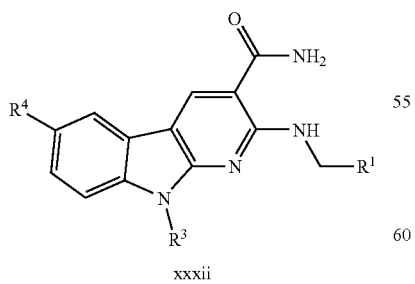

Steps (a) i) ClSO$_2$NCO, DCM ii) H$_2$O (b) R$^1$CO$_2$COR$^1$, DCM (c) TFA, DCM (d) R$^1$CHO, NaBH$_3$CN, MeOH Acetic anhydride (32.8 mL, 347 mmol) was added to a solution of 2-(acetylamino)-9-[(2S)-2-aminopropyl]-9H-pyrido[2,3-b]indole-3-carboxamide (xvi-b, 442 mg, 1.15 mmol) in methylene chloride (2.0 mL). The solution was stirred at room temperature for 16 h then diluted with ethyl acetate (100 mL) and washed with aqueous saturated sodium bicarbonate (50 mL) and brine (50 mL). The organic phase was dried over sodium sulfate and concentrated in vacuo to afford tert-butyl {(1S)-2-[2-(acetylamino)-3-(aminocarbonyl)-9H-pyrido[2,3-b]indol-9-yl]-1 methylethyl}carbamate (xxxi-a, 152 mg, 31%) which was used without further purification. NH₄OAc QC conditions. M+H=426.

Step 2: 2-(acetylamino)-9-[(2S)-2-aminopropyl]-9H-pyrido[2,3-b]indole-3-carboxamide (66)

xxxi-a (44 mg, 0.104 mmol) was deprotected using the TFA conditions detailed in the preparation of 30 to afford the title compound (66, 29 mg, 63%). NH₄OAc standard conditions. DAD Retention time=4.98 min. M+H=326. ¹H NMR (300 MHz, DMSO-d₆): δ 12.27 (br s, 1H), 9.05 (br s, 1H), 8.41 (br s, 1H), 8.31 (br s, 3H), 8.03 (d, J=7.6 Hz, 1H), 7.80 (br s, 1H), 7.75 (d, J=8.2 Hz, 1H), 7.51 (dd, J=7.6, 7.6 Hz, 1H), 7.32 (dd, J=7.0, 7.0 Hz, 1H), 4.53 (br s, 2H), 3.87-3.75 (br m, 1H), 2.32 (s, 3H), 1.16 (d, J=6.5 Hz, 3H).

Compounds in the following table were prepared from the appropriate starting materials in a method analogous to that described in the preparation of 44. Step 2 may be omitted for compounds lacking alkylamine substitutents.

| No. | LCMS Standard Method: (FA/AA) | ES+ | ES− | Retention Time (min) |
|---|---|---|---|---|
| 49 | AA | 297 | | 6.43 |
| 66 | AA | 326 | | 4.98 |

9-ethyl-2-(methylamino)-9H-pyrido[2,3-b]indole-3-carboxamide (48)

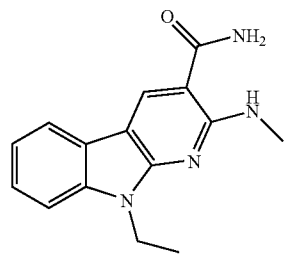

48

2-amino-9-ethyl-9H-pyrido[2,3-b]indole-3-carboxamide (1, 36 mg, 0.141 mmol), formaldehyde (37 wt % in water, 0.011 mL, 0.155 mmol) and acetic acid (0.0084 mL, 0.148 mmol) in methanol (2.6 mL) were stirred at room temperature for 1 h then sodium cyanoborohydride (13 mg, 0.212 mmol) was added. The reaction stirred at room temperature for 16 h, then was quenched with aqueous saturated sodium bicarbonate (2.6 mL). The resulting mixture was diluted with ethyl acetate (100 mL), washed with water (2×50 mL) and brine (50 mL), dried over magnesium sulfate, filtered and then concentrated in vacuo. The residue was adsorbed onto silica gel using methanol and purified by silica gel chromatography (5-10% methanol in methylene chloride gradient) to afford the title compound (48, 25 mg, 66%). NH₄OAc standard conditions. DAD Retention time=7.84 min. M+H=269. ¹H NMR (300 MHz, CDCl₃): δ 8.60 (br s, 1H), 8.19 (s, 1H), 7.79 (d, J=7.9 Hz, 1H), 7.36-7.32 (m, 2H), 7.21-7.17 (m, 1H), 5.65 (br s, 2H), 4.38 (q, J=7.3 Hz, 2H), 3.12 (s, 3H), 1.42 (t, J=7.3 Hz, 3H).

Compounds in the following table were prepared from the appropriate starting materials in a method analogous to that described in the preparation of 48.

| No. | LCMS Standard Method: (FA/AA) | ES+ | ES− | Retention Time (min) |
|---|---|---|---|---|
| 48 | AA | 269 | | 7.84 |
| 69 | AA | 398 | | 8.3 |

9-[(2S)-2-aminopropyl]-2-(methylamino)-9H-pyrido[2,3-b]indole-3-carboxamide (45)

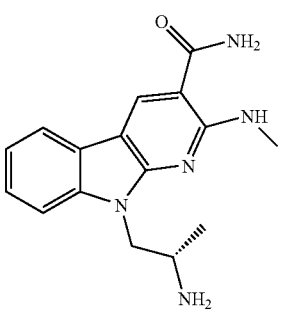

45

Step 1: tert-butyl {(1S)-2-[2-amino-3-(aminocarbonyl)-9H-pyrido[2,3-b]indol-9-yl]-1-methylethyl}carbamate (xxxii-a)

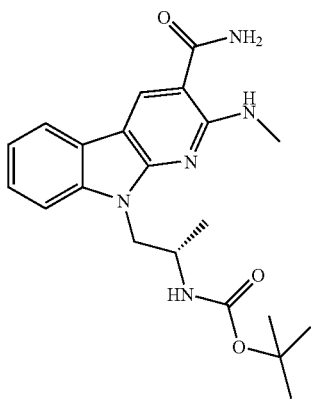

xxxii-a tert-butyl {(1S)-2-[2-amino-3-(aminocarbonyl)-9H-pyrido[2,3-b]indol-9-yl]-1-methylethyl}carbamate (xvi-b, 20 mg, 0.052 mmol) was alkylated according to procedure detailed in the preparation of 48, to afford tert-butyl {(1S)-2-[3-(aminocarbonyl)-2-(methylamino)-9H-pyrido[2,3-b]indol-9-yl]-1-methylethyl}carbamate (xxxii-a, 20 mg, 89%). NH$_4$OAc QC conditions. M+H=398.

Step 2: 9-[(2S)-2-aminopropyl]-2-(methylamino)-9H-pyrido[2,3-b]indole-3-carboxamide (45)

tert-butyl {(1S)-2-[3-(aminocarbonyl)-2-(methylamino)-9H-pyrido[2,3-b]indol-9-yl]-1-methylethyl}carbamate xxxii-a (20 mg, 0.051 mmol) was deprotected according to the TFA procedure detailed in the preparation of 30 to afford the title compound as the trifluoroacetate salt (45, 7 mg, 35%). NH$_4$OAc standard conditions. DAD Retention time=5.33 min. M+H=298. $^1$H NMR (300 MHz, CDCl$_3$): δ 9.04 (br s, 1H), 8.76 (s, 1H), 8.02 (br s, 4H), 7.82 (d, J=7.9 Hz, 1H), 7.57 (d, J=8.5 Hz, 1H), 7.35 (br dd, J=7.3, 7.3 Hz, 1H), 7.23 (br dd, J=7.3, 7.3 Hz, 1H), 4.48-4.44 (m, 1H), 3.04 (s, 3H), 3.57-3.52 (m, 2H), 1.21 (d, J=6.1 Hz, 3H).

Compounds in the following table were prepared from the appropriate starting materials in a method analogous to that described for the synthesis of 45.

| No. | LCMS Standard Method: (FA/AA) | ES+ | ES− | Retention Time (min) |
|---|---|---|---|---|
| 45 | AA | 298 | | 5.33 |
| 51 | AA | 312 | | 5.79 |
| 54 | AA | 374 | | 6.64 |
| 60 | AA | 326 | 324 | 6.22 |
| 70 | AA | 298 | | 5.92 |

Biological Testing

Compounds of this invention are effective inhibitors of IκB kinase (IKK), and therefore, are useful for treating conditions caused or aggravated by the activity of this kinase. The in vitro and in vivo IκB kinase inhibitory activities of the compounds of formula I may be determined by various procedures known in the art. The potent affinities for IκB kinase exhibited by the inventive compounds can be measured as an IC$_{50}$ value (in nM), which is the concentration (in nM) of compound required to provide 50% inhibition of IκB kinase.

Following are examples of assays that can be useful for evaluating and selecting a compound that modulates IKK.

Assay for Measuring IκB Kinase Enzyme Inhibition

An in vitro assay for detecting and measuring inhibition activity against IκB kinase complex by candidate pharmacological agents can employ a biotinylated GST fusion protein spanning residues 5-55 of IκBα (SwissProt Accession No. P25963, Swiss Institute of Bioinformatics, Geneva, Switzerland) and an agent for detection of the phosphorylated product, e.g. a specific antibody binding only to the phosphorylated form GS, being either monoclonal or polyclonal (e.g., commercially-available anti-phospho-serine[32] IκB antibodies). In the example of detecting the phosphorylated product by an anti-phosphoserines[32 and 36] IκB antibody, once the antibody-phospho-GST-IκBα complex is formed, the complex can be detected by a variety of analytical methods (e.g., radioactivity, luminescence, fluorescence, or optical absorbance). For the use of the time resolved fluorescence method the antibody is labeled with europium chelate and the antibody-phospho-GST-IκBα complex is bound to biotin binding protein conjugated to a fluorescence acceptor (e.g., Steptavidin Alexa647, Invitrogen, Carlsbad, Calif.). How to prepare materials for and conduct this assay are described in more detail below.

Isolation of the IκB Kinase Complex

An IκB-α kinase complex is prepared by first diluting 10 ml of HeLa S3 cell-extracts 5100 fraction (Lee et al. (1997) Cell 88:213-222) with 40 ml of 50 mM HEPES pH 7.5. Then, 40% ammonium sulfate is added and incubated on ice for 30 minutes. The resulting precipitated pellet is redissolved with 5 ml of SEC buffer (50 mM HEPES pH 7.5, 1 mM DTT, 0.5 mM EDTA, 10 mM 2-glycerophosphate), clarified by centrifugation at 20,000×g for 15 mM., and filtrated through a 0.22 μm filter unit. The sample is loaded onto a 320 ml SUPEROSE-6 gel filtration FPLC column (Amersham Biosciences AB, Uppsala, Sweden) equilibrated with a SEC buffer operated at 2 ml/min flow rate at 4° C. Fractions spanning the 670-kDa molecular-weight marker are pooled for activation. A kinase-containing pool is then activated by incubation with 100 nM MEKK1Δ (Lee et al. (1997) Cell 88:213-222), 250 μM MgATP, 10 mM MgCl$_2$, 5 mM DTT, 10 mM 2-glycerophosphate, 2.5 μM Microcystin-LR, for 45 minutes at 37° C. The activated enzyme is stored at −80° C. until further use.

Measurement of IκB Kinase Phospho-Transferase Activity

To each well of a 384 well plate, compounds of various concentrations in 1 μL if DMSO are incubated for 2 hours with 30 μL of assay buffer (50 mM Hepes pH 7.5, 5 mM DTT, 10 mM MgCl$_2$ 10 mM 2-glycerophosphate, 0.1% Bovine Serum Albumin) containing a 1:90 dilution of activated enzyme, 100 nM biotinylated-GST-IκBα 5-55, and 50 μM ATP. Reactions are quenched with the addition of 10 μL of 250 mM EDTA before the addition of 40 μL of detection buffer (50 mM Hepes pH 7.5, 0.1% Bovine Serum Albumin, 0.01% Tween20, Pierce, Rockford, Ill.) containing 2 nM europium labeled anti-IκBα phosphoserine[32 and 36] and 0.003 mg/mL Streptavidin Alexa647. Samples are allowed to incubate for 1 hour prior to reading on a Wallac Victor plate reader (Perkin Elmer Life and Analytical Sciences, Boston, Mass.). As the assay has been previously shown to be linear with respect to enzyme concentration and time at the enzyme dilution tested, levels of time resolved fluorescence energy transfer are used to determine the inhibition activity of candidate pharmacological agents.

The compounds of the invention are inhibitors of the IKK complex. It will be appreciated that compounds of this invention can exhibit IκB kinase inhibitor activities of varying degrees. Following assay procedures described herein, the IκB kinase inhibition average IC$_{50}$ values for the inventive compounds were generally below about 10 micromolar, preferably below about 1.0 micromolar, and more preferably below about 100 nanomolar.

Cellular Assays: A variety of cellular assays are also useful for evaluating compounds of the invention:

Multiple Myeloma (MM) Cell Lines and Patient-Derived MM Cells Isolation

RPMI 8226 and U266 human MM cells are obtained from American Type Culture Collection (Manassas, Va.). All MM cell lines are cultured in RPMI-1640 containing 10% fetal bovine serum (FBS, Sigma-Aldrich Co., St. Louis, Mo.), 2 mM L-glutamine, 100 U/mL penicillin (Pen) and 100 μg/mL streptomycin (Strep) (GIBCO brand cell culture products available from Invitrogen Life Technologies, Carlsbad, Calif.). Patient-derived MM cells are purified from patient bone marrow (BM) aspirates using ROSETTESEP (B cell enrichment kit) separation system (StemCell Technologies, Vancouver, Canada). The purity of MM cells are confirmed by flow cytometry using PE-conjugated anti-CD138 antibody (BD Biosciences, Bedford, Mass.).

Bone Marrow Stroma Cell Cultures

Bone marrow (BM) specimens are obtained from patients with MM. Mononuclear cells (MNCs) separated by Ficoll-Hipaque density sedimentation are used to established long-term BM cultures as previously described (Uchiyama et al., *Blood* 1993, 82:3712-3720). Cells are harvested in Hank's Buffered Saline Solution (HESS) containing 0.25% trypsin and 0.02% EDTA, washed, and collected by centrifugation.

Cell Proliferation Via Measurement of DNA-Synthesis Rate

Proliferation is measured as described (Hideshima et al., *Blood* 96:2943 (2000)). MM cells ($3\times10^4$ cells/well) are incubated in 96-well culture plates (Corning Life Sciences, Corning, N.Y.) in the presence of media or an IKK inhibitor of this invention for 48 h at 37° C. DNA synthesis is measured by [$^3$H]-thymidine ([$^3$H]-TdR, New England Nuclear division of Perkin Elmer Life and Analytical Sciences, Boston, Mass.) incorporation into dividing cells. Cells are pulsed with [$^3$H] TdR (0.5 µCi/well) during the last 8 h of 48 h cultures. All experiments are performed in triplicate.

MTT Cell Viability Assay

The inhibitory effect of the present compounds on MM growth is assessed by measuring the reduction of yellow tetrazolium MIT (3-(4,5-dimethylthiazolyl-2)-2,5-diphenyltetrazolium bromide) by metabolically active cells (J. Immunol. Methods 174: 311-320, 1994). Cells from 48 h cultures are pulsed with 10 µL of 5 mg/mL MTT to each well for the last 4 h of the 48 h cultures, followed by 100 µL isopropanol containing 0.04N HCl. Absorbance is measured at 570 nm using a spectrophotometer (Molecular Devices Corp., Sunnyvale Calif.).

NF-κB Activation Via Electrophoretic Mobility Shift Assay

Electrophoretic mobility shift analyses (EMSA) are carried out as described (Hideshima et al., *Oncogene* 2001, 20:4519). Briefly, MM cells are pre-incubated with an IKK inhibitor of this invention (10 µM for 90 min) before stimulation with TNF-α (5 ng/mL) for 10 to 20 min. Cells are then pelleted, resuspended in 400 µL of hypotonic lysis buffer (20 mM HEPES, pH 7.9, 10 mM KCl, 1 mM EDTA, 0.2% Triton X-100, 1 mM Na$_3$VO$_4$, 5 mM NaF, 1 mM PMSF, 5 µg/mL leupeptin, 5 µg/mL aprotinin), and kept on ice for 20 min. After centrifugation (14000 g for 5 min) at 4° C., the nuclear pellet is extracted with 100 µL hypertonic lysis buffer (20 mM HEPES, pH 7.9, 400 mM NaCl, 1 mM EDTA, 1 mM Na$_3$VO$_4$, 5 mM NaF, 1 mM PMSF, 5 µg/mL leupeptin, 5 µg/mL aprotinin) on ice for 20 min. After centrifugation (14000 g for 5 min) at 4° C., the supernatant is collected as nuclear extract. Double-stranded NF-κB consensus oligonucleotide probe (5'-GGGGACTTTCCC-3', Santa Cruz Biotechnology Inc., Santa Cruz Calif.) is end-labeled with [($^{32}$P]ATP (50 µCi at 222 TBq/mM; New England Nuclear division of Perkin Elmer Life and Analytical Sciences, Boston, Mass.). Binding reactions containing 1 ng of oligonucleotide and 5 µg of nuclear protein are conducted at room temperature for 20 min in a total volume of 10 µL of binding buffer (10 mM Tris-HCl, pH 7.5, 50 mM NaCl, 1 mM MgCl$_2$, 0.5 mM EDTA, 0.5 mM DTT, 4% glycerol (v/v), and 0.5 µg poly (dI-dC) (Amersham Biosciences AB, Uppsala, Sweden). For supershift analysis, 1 µg of anti-p65 NF-κB Ab is added 5 min before the reaction mixtures, immediately after addition of radiolabeled probe. The samples are loaded onto a 4% polyacrylamide gel, transferred to Whatman paper (Whatman International, Maidstone, U.K.), and visualized by autoradiography.

Diffuse Large B-Cell Lymphoma (DLBCL) Cell Proliferation Assay

ABC-like (LY3 and Ly10) and GCB-like (Ly7 and Ly19) DLBCL cell lines (Alizadeh et al (2000) Nature 403:503-511; Davis et al. (2001) J. Exp. Med. 194:1861-1874) are maintained in growth medium (GM, Iscove's DMEM+10% FBS) by passaging cells twice per week. Cells are starved overnight in Iscove's DMEM medium+0.5% FBS overnight before plated in proliferation assay. On the day of the assay, cells are counted and viability is checked using Trypan Blue staining. For the Ly3 and Ly10 cells, 5000 cell are plated in GM per well in a 96-well plate. The Ly7 and Ly19 cells are plated at 10,000 cells per well. IKK inhibitors are first dissolved in DMSO and then diluted in GM to reach the final concentrations of 80 µM-0.01 µM. Each concentration is plated in triplicate. Cell viability is determined using a standard WST-1 cell viability assay (Roche Applied Science, Indianapolis, Ind.).

Human Peripheral Blood Monocyte (PBMC) Cytokine Release Assay

Human PBMC is purified from normal donor whole blood by Ficoll gradient method. After a PBS wash, PBMC are re-suspended in AIM-V medium. Serially diluted IKK inhibitors of this invention in 100% DMSO are added at 1 µl to the bottom of a 96-well plate and mixed with 180 µl $4.5\times10^5$ PBMC in AIM-V media per well. After preincubating PBMC with inhibitor at 37° C. for 40 min, cells are stimulated with 20 µl of either with LPS (100 ng/ml) or with anti-CD3 (0.25 µg/ml) and anti-CD28 (0.25 µg/ml) (Pharmingen division of BD Biosciences, Bedford, Mass.) at 37° C. for 5 hours. The supernatants are collected and assessed for IL-1β or TNFα release using standard commercially available ELISA kits.

Human Chondrocyte Matrix Metalloproteases (MMPs) Release Assay

Human chondrocyte cell line SW1353 (ATCC, Manassas, Va.) is cultured containing 10% fetal bovine serum (Hyclone, Logan, Utah), 2 mM L-glutamine (GIBCO brand cell culture products available from Invitrogen Life Technologies, Carlsbad, Calif.) and 1% Pen/Strep (GIBCO). Cells are seeded in 96-well Poly-D-Lysine plate (BD BIOCOAT, Black/Clear bottom, BD Biosciences, Bedford, Mass.). Serially diluted IKK inhibitors at 1 µl are added to each well of 96-well plates and mixed with 180 µl $4.5\times10^5$ chondrocytes per well. After pre-incubating cells with compounds for 1 hr at 37° C., cells are stimulated with 20 µl IL-1β (10 ng/mL, R&D Systems Inc.) at 37° C. for 24 hrs. The supernatants are then collected and assessed for production of matrix metalloproteinases (MMPs) using commercially available ELISA kits.

Human Fibroblast Like Synoviocyte (HFLS) Assay

HFLS isolated from RA synovial tissues obtained at joint replacement surgery are provided by Cell Applications Inc. (San Diego, Calif.). IKK inhibitors of the invention are tested for their ability to block the TNF- or IL-1β-induced release of IL-6 or IL-8 from these cells using commercially available ELISA kits. Cell culture conditions and assay methods are described in Aupperle et al., *Journal of Immunology*, 163: 427-433 (1999).

Human Cord Blood Derived Mast Cell Assay

Human cord blood is obtained from Cambrex (Walkersville, Md.). Mast cells are differentiated and cultured in a manner similar to that described by Hsieh et al., *J. Exp. Med.*, 193:123-133 (2001). IKK inhibitors of the invention are tested for their ability to block the IgE- or LPS-induced TNFα release using commercially available ELISA kits.

Osteoclast Differentiation and Functional Assays

Human osteoclast precursors are obtained as cryopreserved form from Cambrex (Walkersville, Md.). The cells are differentiated in culture based on instructions from the manufacturer. IKK inhibitors of the invention are tested for their ability to block the differentiation, bone resorption and collagen degradation as described previously (see Khapli, S. M., *Journal of Immunol*, 171:142-151 (2003); Karsdal, M. A., *J Biol Chem*, 278:44975-44987 (2003); and Takami, M., *Journal of Immunol*, 169:1516-1523 (2002)).

Rat Models for Rheumatoid Arthritis

Such testing is known in the literature and include a standard rat LPS model as described in Conway et al., "Inhibition of Tumor Necrosis Factor-α (TNF-α) Production and Arthritis in the Rat by GW3333, a Dual Inhibitor of TNF—Converting Enzyme and Matrix Metalloproteinases", *J. Pharmacol. Exp. Ther.* 298(3), 900-908 (2001); a rat adjuvant induced arthritis model as described in Pharmacological Methods in the Control of Inflammation (1989) p 363-380 "Rat Adjuvant Arthritis: A Model of Chronic Inflammation" Barry M. Weichman author of book chapter {Alan R. Liss Inc Publisher}; and a rat collagen induced arthritis model as described in Pharmacological Methods in the Control of Inflammation (1989) p 395-413 "Type II Collagen Induced Arthritis in the Rat" D E Trentham and R A Dynesuis-Trentham authors of book chapter {Alan R. Liss Inc Publisher}. See also, "Animal Models of Arthritis: Relevance to Human Disease" (1999) by A. Bendele, J. McComb, T. Gould, T. McAbee, G. Sennello, E. Chlipala and M. Guy. Toxicologic Pathology Vol 27 (1) 134-142.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:

1. A method of treating cancer in a patient comprising administering to said patient a therapeutically effective amount of a compound of formula I,

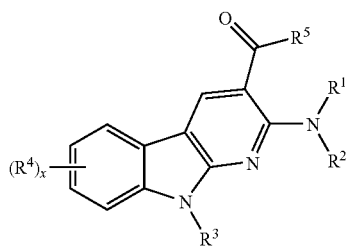

I or a pharmaceutically acceptable salt thereof wherein,
$R^1$ is hydrogen, $C_1$-$C_4$aliphatic, —C(O)N($R^{1a}$)$_2$, —C(O)$R^{1b}$, or —(CH$_2$)$_n$$R^{1c}$,
  wherein each occurrence of $R^{1a}$ is independently hydrogen, C(O)O$R^{1d}$, or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of $R^{1a}$ are taken together with a nitrogen atom to which they are bound to form an optionally substituted 3-7-membered heterocyclyl ring;

$R^{1b}$ is an optionally substituted group selected from $C_1$-$C_6$aliphatic or phenyl;
$R^{1c}$ is —N($R^{1a}$)$_2$, or an optionally substituted phenyl or pyridyl group;
$R^{1d}$ is $C_1$-$C_6$aliphatic; and
n is 1, 2 or 3;
$R^2$ is hydrogen or $C_1$-$C_4$aliphatic;
$R^3$ is —H, -T$_1$-$R^{3d}$, —V$_1$-T$_1$-$R^{3d}$, or —$R^{3e}$, wherein
  $V_1$ is —C(O)—, —S(O)$_2$—, —C(O)N$R^{3a}$—, or —S(O)$_2$N$R^{3a}$—;
  $T_1$ is a $C_1$-$C_6$alkylene chain optionally substituted with one or more independent occurrences of —$R^{3b}$, wherein the alkylene chain optionally is interrupted by —C(R')=C(R')—, —C≡C—, —N(R')—, —O—, —S—, —S(O)—, —S(O)$_2$—, —C(O)—, —C(O)O—, —C(O)N(R')—, —S(O)$_2$N(R')—, —OC(O)N(R')—, —N(R')C(O)—, —N(R')SO$_2$—, —N(R')C(O)O—, —NR'C(O)N(R')—, —N(R')S(O)$_2$N(R')—, —OC(O)—, or —C(O)N(R')—O— or wherein $T_1$ or a portion thereof optionally forms part of an optionally substituted 3-7 membered cycloaliphatic or heterocyclyl ring;
  each occurrence of $R^{3a}$ is independently hydrogen or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or wherein two occurrences of $R^{3a}$ are taken together with a nitrogen atom to which they are bound to form an optionally substituted 3-7-membered heterocyclyl ring;
  each occurrence of $R^{3b}$ is independently halogen, —CN, —NO$_2$, —$R^{3c}$, —N($R^{3a}$)$_2$, —O$R^{3a}$, —S$R^{3c}$, —S(O)$_2$$R^{3c}$, —C(O)$R^{3a}$, —C(O)O$R^{3a}$, —C(O)N($R^{3a}$)$_2$, —S(O)$_2$N($R^{3a}$)$_2$, —OC(O)N($R^{3a}$)$_2$, —N(R')C(O)$R^{3a}$, —N(R')SO$_2$$R^{3c}$, —N(R')C(O)O$R^{3a}$, —N(R')C(O)N($R^{3a}$)$_2$, —N(R')SO$_2$N($R^{3a}$)$_2$, —N$R^{3a}$(C=N$R^{3a}$)N($R^{3a}$)$_2$, =N$R^{3a}$, =N—N($R^{3a}$)$_2$, =N—O$R^{3a}$, =N—NHC(O)$R^{3a}$, =N—NHCO$_2$$R^{3a}$, =N—NHSO$_2$$R^{3a}$, or two occurrences of $R^{3a}$ or $R^{3c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur;
  each occurrence of $R^{3c}$ is independently an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{3d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{3e}$ is independently an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur and each R' is independently hydrogen or optionally substituted $C_{1-6}$aliphatic;

x is 0-4;

each occurrence of $R^4$ is independently —$R^{4a}$, -$T_2$-$R^{4d}$, or —$V_2$-$T_2$-$R^{4d}$, wherein:

each occurrence of $R^{4a}$ is independently halogen, —CN, —$NO_2$, —$R^{4c}$, —$N(R^{4b})_2$, —$OR^{4b}$, —$SR^{4c}$, —$S(O)_2R^{4c}$, —$C(O)R^{4b}$, —$C(O)OR^{4b}$, —$C(O)N(R^{4b})_2$, —$S(O)_2N(R^{4b})_2$, —$OC(O)N(R^{4b})_2$, —$N(R')C(O)R^{4b}$, —$N(R')SO_2R^{4c}$, —$N(R')C(O)OR^{4b}$, —$N(R')C(O)N(R^{4b})_2$, or —$N(R')SO_2N(R^{4b})_2$, or two occurrences of $R^{4b}$ or $R^{4c}$ are optionally taken together with their intervening atom(s) to form an optionally substituted fused ring selected from a 6-membered aryl, or a 5-6-membered heteroaryl having 1-3 heteroatoms independently selected from nitrogen, oxygen, or sulfur, or two occurrences of $R^{4b}$, taken together with a nitrogen atom to which they are bound, form an optionally substituted 3-7-membered heterocyclyl ring having 0-3 additional heteroatoms selected from nitrogen, oxygen, or sulfur;

each occurrence of $R^{4b}$ is independently hydrogen or an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4c}$ is independently an optionally substituted group selected from $C_1$-$C_6$aliphatic, 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4d}$ is independently hydrogen or an optionally substituted group selected from 3-10-membered cycloaliphatic, 3-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $V_2$ is independently —C(R')=C(R')—, —C≡C—, —N(R')—, —O—, —S—, —S(O)—, —$S(O)_2$—, —C(O)—, —C(O)O—, —C(O)N(R')—, —$S(O)_2N(R')$—, —OC(O)N(R')—, —N(R')C(O)—, —$N(R')SO_2$—, —N(R')C(O)O—, —NR'C(O)N(R')—, —$N(R')SO_2N(R')$—, —OC(O)—, or —C(O)N(R')—O—; and each occurrence of $T_2$ is independently a $C_1$-$C_6$alkylene chain optionally substituted with $R^{4a}$, wherein the alkylene chain optionally is interrupted by —C(R')=C(R')—, —C≡C—, —N(R')—, —O—, —S—, —S(O)—, —$S(O)_2$—, —C(O)—, —C(O)O—, —C(O)N(R')—, —$S(O)_2N(R')$—, —OC(O)N(R')—, —N(R')C(O)—, —$N(R')SO_2$—, —N(R')C(O)O—, —NR'C(O)N(R')—, —$N(R')SO_2N(R')$—, —OC(O)—, or —C(O)N(R')—O— or wherein $T_2$ or a portion thereof optionally forms part of an optionally substituted 3-7 membered cycloaliphatic or heterocyclyl ring, and $R^5$ is —$NR^6R^7$ or —OH, wherein:

$R^6$ and $R^7$ are each independently hydrogen or $C_1$-$C_4$aliphatic;

provided that the compound of formula I is other than:
a) 2-amino-9-ethyl-9H-Pyrido[2,3-b]indole-3-carboxamide;
b) 2-amino-1H-Pyrido[2,3-b]indole-3-carboxamide, or the monohydrochloride thereof,
c) 2-amino-1H-Pyrido[2,3-b]indole-3-carboxylic acid; or
d) 2-amino-9-(2,6,-dichlorophenyl)-9H-Pyrido[2,3-b]indole-3-carboxamide.

2. The method of claim 1 wherein the cancer is Non-Hodgkin's lymphoma, multiple myeloma, or head and neck squamous cell carcinoma.

3. A method of treating an inflammatory disease or immune-related disease in a patient comprising administering to said patient a therapeutically effective amount of a compound of claim 1.

4. The method of claim 2 wherein the disease is rheumatoid arthritis, asthma, psoriasis, psoriatic arthritis, chronic obstructive pulmonary disease, inflammatory bowel disease, or multiple sclerosis.

5. The method of claim 4, wherein the disease is rheumatoid arthritis, multiple sclerosis, asthma, or chronic obstructive pulmonary disease.

* * * * *